(12) United States Patent
Novak et al.

(10) Patent No.: US 6,331,407 B1
(45) Date of Patent: Dec. 18, 2001

(54) ANTIBIOTICS AND METHODS OF USING THE SAME

(75) Inventors: Rodger Novak, Memphis; Elaine I. Tuomanen, Germantown, both of TN (US)

(73) Assignee: St. Jude Children's Research Hospital, Memphis, TN (US)

( * ) Notice: Subject to any disclaimer, the term of this patent is extended or adjusted under 35 U.S.C. 154(b) by 0 days.

(21) Appl. No.: 09/305,984

(22) Filed: May 5, 1999

Related U.S. Application Data

(60) Provisional application No. 60/084,399, filed on May 6, 1998.

(51) Int. Cl.[7] ............................................. G01N 33/569
(52) U.S. Cl. .................... 435/7.34; 435/7.2; 435/7.32; 435/243; 435/252.1; 435/253.4; 514/12
(58) Field of Search ................................ 435/7.2, 7.32, 435/7.34, 243, 252.1, 253.4; 514/12

(56) References Cited

U.S. PATENT DOCUMENTS

| | | |
|---|---|---|
| 4,925,673 | 5/1990 | Steiner . |
| 5,013,556 | 5/1991 | Woddle . |

FOREIGN PATENT DOCUMENTS

| | | |
|---|---|---|
| 0885903 | 12/1998 | (EP) . |
| WO9117256 | 11/1997 | (WO) . |
| WO9741146 | 11/1997 | (WO) . |

OTHER PUBLICATIONS

Williamson et al. (J Bacteriology 114 (1): 105–13, 1980).*
Alberts et al, 1994, Molecular Biology of the Cell, 3rd ed, Garland Publishing Inc (NY), pp. 519–22.
Bassam et al., 1991, Anal Biochem, 196:80–3.
Bevins et al, 1990, Ann Rev Biochem, 59:395–414.
Cintas et a l, 1998, J Bad, 180:1988–94.
Field et al, 1990, Int J Pept Protein Res, 35:161–214.
Friedland et al., 1993, Pediatr Infec Dis J, 12:196–200.
Handwerger et al., 1985, Rev Infect Dis, 7:368–86.
Havarstein et al., 1995, Proc Natl Acad Sci USA, 92:11140–4.
Lacks et al., 1960, Biochem Biophys Acad, 39:508–17.
Langer, 1990, Science, 249:1527–33.
Levy et al, 1998, Scientific American, Mar.: 46–53.
Liu et al., 1985, J Infect Dis, 152:365–72.
Marshall, 1979, in Modern Pharmaceutics, Banker et al. Ed., Chapter 10.
Mayasaki et al, 1998, Int J Antimicrob Agents, 9:269–80.
Mizuno 1997, DNA Res, 4:161–8.
Nagai et al, 1985, Tetrahedron Lett, 26:647–50.
Stone et al., 1997, Science, 275:668–70.
Tiraby et al., 1973, Proc Natl Acad Sci USA, 70:3541–5.
Tomasz et al, 1970, Nature, 227:138–40.
Tuomanen et al, 1986, Rev Infect Dis, 3:S279–91.
Tuomanen et al, 1988, J Infect Dis, 158:36–43.
Weider et al., 1964, Enzymol, 26:193–232.
Kleerebezem et al., 1997, Mol. Microbiology, 24:895–904.
Desnottes, 1996, Trends in Biotechnology, 14:134–140.
Novak et al., 1998, Abstracts of the Interscience Conference on Antomicrobial Agents and Chemotherapy, 38:110.
Novak et al., 1999, Nature, 399:590–3.

* cited by examiner

Primary Examiner—Donna Wortman
Assistant Examiner—Robert A. Zeman
(74) Attorney, Agent, or Firm—Klauber & Jackson

(57) ABSTRACT

The present invention discloses novel antibiotic peptides, including naturally occurring peptides. The present invention also includes the nucleic acid sequences encoding such peptides and the corresponding amino acid sequences. Methods of identifying, making, and using the antibiotic peptides are also disclosed. The present invention further provides novel proteins involved in the regulation of bacterial autolysis.

8 Claims, 22 Drawing Sheets

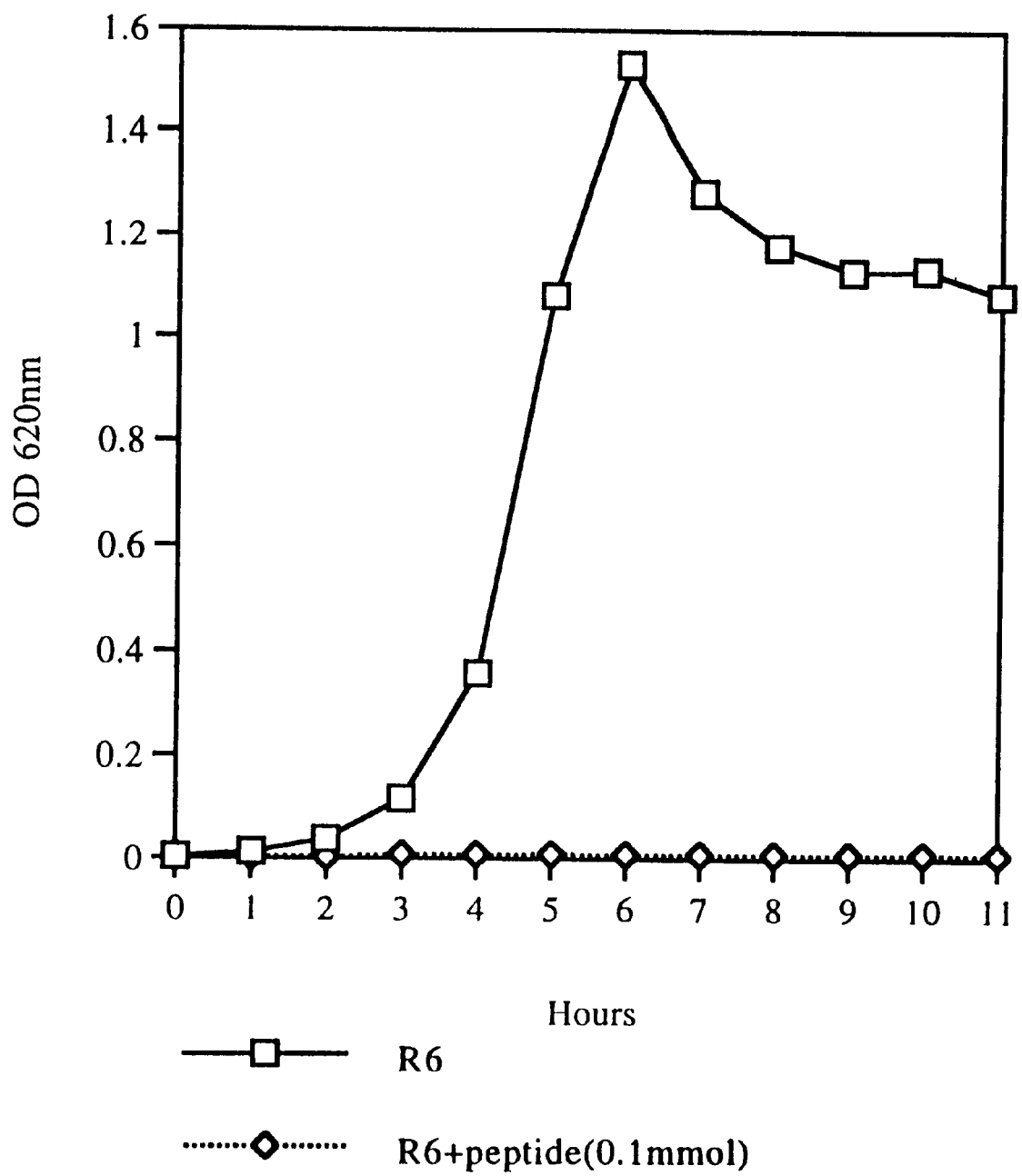

Titration of the 25aa peptide effect after 4 hours

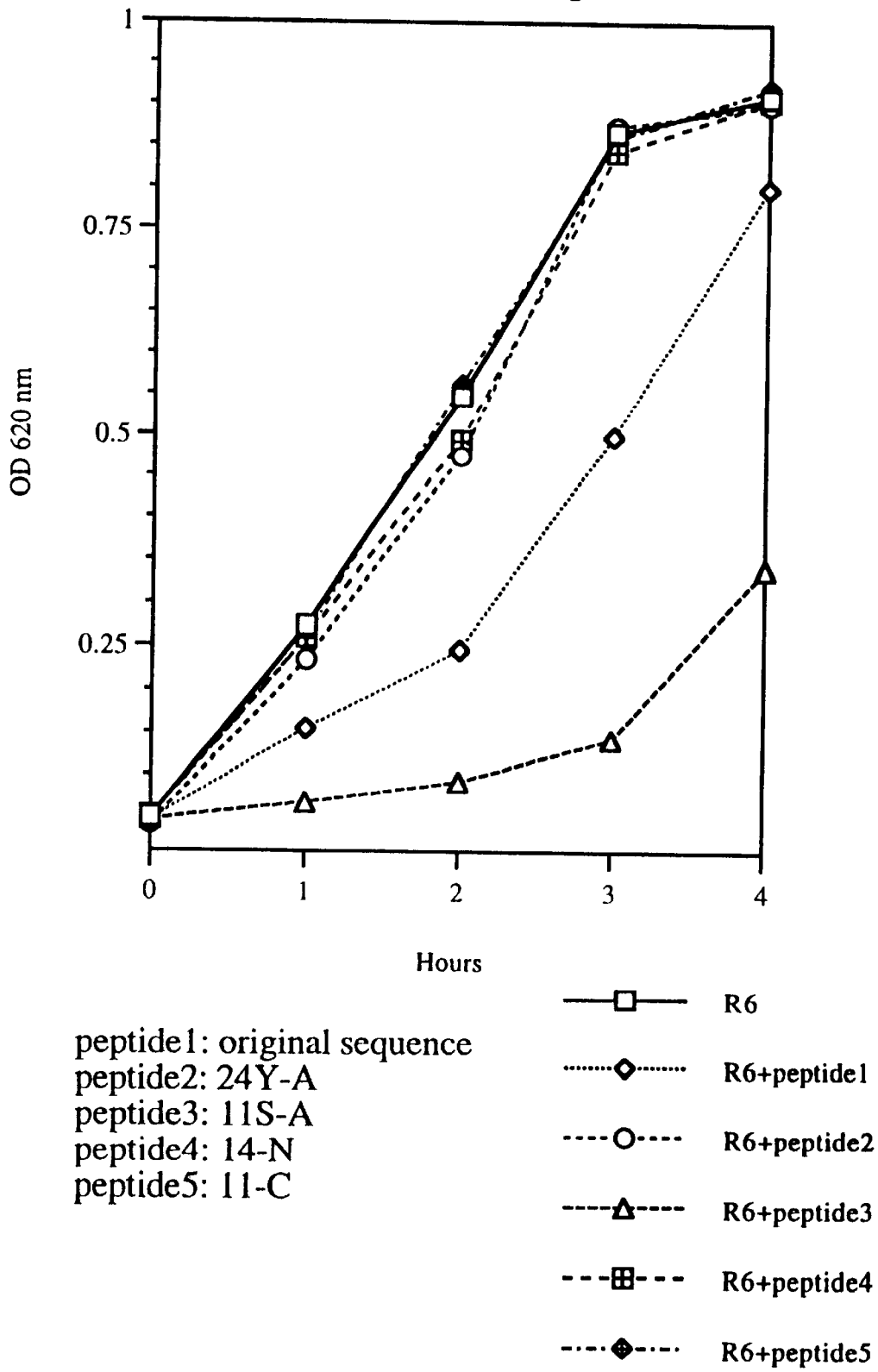

Northern blot analysis of intergenic region

Effect of penicillin (10 x MIC) and peptide (0.5 mmol) on lysis of R6 under starvation conditions Effect of penicillin (10 x MIC) and peptide (0.5 mmol) on lysis of F79

Effect of penicillin (10 x MIC) and peptide (0.5mmol) on lysis of VanS/HK

SSCP (single stranded conformational polymorphism) analysis of the gene VanS/HK (type 4 and F79) of S. pneumoniae

ANTIBIOTICS AND METHODS OF USING THE SAME

CROSS-REFERENCE TO RELATED APPLICATIONS

The present Application is a non-provisional application claiming the priority of copending provisional U.S. Ser. No. 60/084,399 filed May 6, 1998, the disclosure of which is hereby incorporated by reference in its entirety. Applicants claim the benefits of this Application under 35 U.S.C. §119(e).

RESEARCH SUPPORT

The research leading to the present invention was supported in part by Grant NOs: AI27913 and AI39482 from the National Institutes of Health. Accordingly, the Government may have certain rights in the present invention. Support for this invention was also provided by the AMERICAN LEBANESE SYRIAN ASSOCIATED CHARITIES.

FIELD OF THE INVENTION

The invention relates to the field of novel antibiotic peptides, including naturally occurring peptides. The nucleic acid sequence encoding the peptide and the corresponding amino acid sequence are included, together with methods of using the same.

BACKGROUND OF THE INVENTION

Bacterial infections remain among the most common and deadly causes of human disease. Unfortunately, the overuse of antibiotics has led to antibiotic resistant pathogenic strains of bacteria. Indeed, bacterial resistance to the new chemical analogs of these drugs appears to be out-pacing the development of such analogs. For example, life-threatening strains of three species of bacteria (*Enterococcus faecalis, Mycobacterium tuberculosis*, and *Pseudomonas aeruginosa*) have evolved to be resistant against all known antibiotics. [Stuart B. Levy, "The Challenge of Antibiotic Resistance", in *Scientific American*, pgs. 46–53 (March 1998)]

Classical penicillin-type antibiotics bind to cell wall synthetic enzymes and thereby deregulate the activity of a single class of proteins known as autolysins which leads to bacterial lysis and bacterial cell death. The development of new drugs which affect an alternative bacterial target protein would be desirable. Pneumococcus is a particularly relevant organism for such study because 1) it has only one autolysin (LytA rather than the multiple autolysins of other bacteria), 2) the autolysin has been cloned and sequenced and can therefore be easily manipulated genetically, and 3) pneumococcus has only one growth zone so that is possible to study activation of the enzyme in a fairly defined region of the cell.

Most bacteria are stabilized by a cell wall consisting of a glycopeptide polymeric murein (peptidoglycan) that completely enclosed the cell [Weidel & Pelzer et al., *Enzymol.*, 26:193–232 (1964)]. Expansion of the cell wall during bacterial growth and splitting of the septum for cell separation requires enzymes that can cleave this covalently closed network. In addition to acting as spacemaker enzymes for cell wall growth [Tomasz et al., *Walter de Gruyter*, 155–172 (1983)], certain murein hydrolases also act as autolysins, putative suicide enzymes. The life and death dichotomy of autolysin function demonstrates the need for efficient and strict regulation of murein hydrolase activity. Not surprisingly, the regulation of the autolysins is a highly sophisticated physiological task. For example, the enzymes must be controlled at their extracytoplasmic location. In addition, most bacteria possess multiple hydrolases which must be controlled in concert. Antibiotics such as penicillin induce bacteriolysis by interfering with the control of the endogenous autolytic enzymes, indicating the significant chemotherapeutic relevance of these enzymes. Although the binding of antibiotics to cell wall synthetic enzymes has been very well characterized, it is unknown how this event leads to deregulation of autolytic enzymes.

Antibiotic tolerance, a phenomenon distinct from antibiotic resistance, was first described in 1970 in pneumococci and provided a significant clue to the mechanism of action of penicillin [Tomasz et al., *Nature*, 227:138–140 (1970)]. Tolerance strains stop growing in the presence of conventional concentrations of antibiotic, but do not subsequently die. Tolerance arises when the bacterial autolytic enzymes, i.e., autolysins, fail to be triggered as the antibiotic inhibits the cell wall synthetic machinery. This explicitly implies that penicillin kills bacteria by activating a set of endogenous hydrolytic enzymes and that bacteria exhibit strategies to stop this activation resulting in survival of antibiotic therapy.

Tolerance is of clinical significance since it has been shown that the inability to eradicate tolerant bacteria leads to failure of antibiotic therapy in clinical infections [Handwerger and Tomasz, *Rev. Infect. Dis.*, 7:368–386 (1985); Tuomanen E., *Rev. Insect. Dis.*, 3:S279–S291 (1986); and Tuomanen et al., *J. Infect. Dis.*, 158:36–43 (1988)]. Furthermore, tolerance is thought to be a prerequisite to the development of antibiotic resistance since it creates survivors of antibiotic therapy. These survivors can then acquire new genetic elements of resistance which allow growth in the presence of antibiotics. Virtually all resistant strains also have been shown to be tolerant [Liu and Tomasz, *J. Infect. Dis.*, 152:365–372 (1985)]. Therefore, the identification of novel antibiotics which can lyse these "antibiotic-tolerant" bacteria is necessary.

Mechanistically speaking, tolerance arises in two settings: 1) all bacteria become phenotypically tolerant as growth rate decreases [Tuomanen E., *Revs. Infect. Dis.*, 3:S279–S291 (1986)] and 2) some bacteria are genotypically tolerant by virtue of acquisition of mutations. In both cases, the basic phenomenon is the down regulation of autolysin triggering. This down regulation is transient in phenotypic tolerance in response to environmental cues and is permanent in genotypic tolerance where mutation has changed the lysis control loop. Obviously, the simplest example of genotypic tolerance is the deletion of the autolytic enzymes. This artificial situation was the basis of the first tolerant mutant described in 1970 [Tomasz et al., *Nature*, 227:138–140 (1970)] but for reasons that are not clear, no clinical isolates have been found which are tolerant because of deletion of these suicidal enzymes. Rather, clinical tolerance arises at the level of regulation of autolysin activity [Tuomanen et al., *J. Infect. Dis.*, 158:36–43 (1988) and Tuomanen et al., *Escherichia coli. J. Bacteriol.*, 170:1373–1376 (1988)].

The most striking examples of powerful regulation of autolysis occur during bacterial response to stress: the stringent response to nutrient deprivation and the heat shock response. The existence of stress-induced global regulators of autolysis described are indicative of strong negative controls on hydrolase deregulation. Thus, bacteria control autolytic activity in order to prevent suicidal lysis. On the other hand, a striking beneficial clinical effect would accrue if one were able to prevent the generation of this protective response in bacteria, particularly in the case of recalcitrant infections involving bacteria sequestered in areas deficient in growth requirements, such as the cerebrospinal fluid, joint fluid, aqueous humor, cardiac vegetations, abscesses, and bone. It stands to reason that the course of therapy for all such infections is prolonged by the need to eradicate phenotypically tolerant bacteria to avoid the rapid relapse observed when antibiotic therapy is withdrawn and surviving bacteria begin to multiply once again. By identifying new antibiotics which can lyse these antibiotic-tolerant bacteria, it should be possible to subvert the protective effects on bacterial survival of slow growth rate or genotypic mutation to tolerance in vivo, thereby globally improving the outcome of antibiotic therapy. Bacteria have developed a complex signaling system that enables the cell to respond swiftly to environmental stress. The histidyl-aspartyl (His-Asp) phosphorelay signal transduction system plays a major role in this signal transduction. There are two key participants in the His-Asp phosphorelay signal transduction system: (1) a sensor histidine kinase, which is generally a transmembrane protein; and (2) a response regulator which mediates changes in gene expression and/or cellular locomotion. The sensor histidine kinase contains a periplasmic or extracellular receptor that detects the external signal, and the sensor histidine kinase then mediates the signal into the cell by activating its corresponding response regulator. The activated response regulator then carries the signal intracellularly to effect the cellular response to the external signal. To date, 23–28 open reading frames have been identified in the *Escherichia coli* genome as encoding putative sensory histidine kinases, whereas 32 open reading frames have been identified as encoding putative response regulators [Mizuno, *DNA Research*, 4:161–168 (1997)]. The sensory histidine kinase of the His-Asp phosphorelay signal transduction system contains a specific histidine that is autophosphorylated in the presence of ATP. The sensor histidine kinase transfers the phosphoryl group to a specific aspartyl residue of the response regulator. This phosphoryl transfer activates the response regulator and thereby transduces the signal, allowing the cell to rapidly respond to a particular environmental challenge.

Most bacteria also possess transport ATPases that use the energy derived from their enzymatic hydrolysis of ATP to transport compounds into the cell. In *E. coli*, for example, the transport ATPases are located in the bacterial inner membrane, and they transport compounds from the periplasmic space into the cell. Transport ATPases are members of a large family of transport proteins termed ABC transporters. The name is derived from a highly conserved ATP-binding cassette contained by all of the members. Generally, ABC transporters are specific for a particular type of molecule (e.g., an amino acid, a sugar, an inorganic ion, a peptide or even a protein). [See, Alberts et al., *Molecular Biology of the Cell*, 3rd edition, Garland Publishing Inc. (New York) Pages 519–522 (1994)]. Heretofore, the relationship between autolysins, His-Asp phosphorelay systems, and ABC transporters has remained obscure.

Bacteria produce peptides and small organic molecules that kill neighboring bacteria. These bacteriocins are of three varieties based on structure: 1) lantibiotics, 2) nonlantibiotics, and 3) others secreted by virtue of a signal peptide (see Cintas et al., *J. Bad.*, 180:1988–1994 (1998)]. Animals, including insects, also naturally produce peptide antibiotics [Bevins et al., *Ann. Rev. Biochem.*, 59:395–414 (1990)]. These antibiotics have been organized in three structural groups: (1) Cysteine-rich β-sheet peptides; (2) α-helical, ampliphatic molecules; and (3) proline-rich peptides [Mayasaki et al., *Int. J. of Antimicrob. Agents*, 9:269–280 (1998)]. However, the use of such antibiotics to combat resistant bacterial strains is only beginning to be exploited.

New approaches to drug development are necessary to combat the ever-increasing number of antibiotic-resistant pathogens. In addition, new antibiotics need to be identified which will act independently of autolysins such as the pneumococcal autolysin, LytA. Furthermore, there is a need to provide pharmaceutical compositions containing such new antibiotics in order to more effectively treat bacterial infections and inflammations.

The citation of any reference herein should not be construed as an admission that such reference is available as "Prior Art" to the instant application.

SUMMARY OF THE INVENTION

The present invention provides methods of identifying novel antibiotic peptides. In addition, the present invention provides the antibiotics themselves. In a particular embodiment, the peptides can act with another antibiotic, such as penicillin, to synergistically kill slow growing or non-growing bacteria. Included in the present invention are antibiotic peptides that can contain unnatural amino acids and/or are branched or cyclic in structure. In a particular embodiment, the peptide is neither hydrophobic nor cationic. The present invention further provides methods of using the antibiotics in the treatment and prevention of bacterial infections and inflammations.

A key aspect of the present invention are antibiotic peptides comprising a portion of the amino acid sequence of MEFMRKEFHNVLSSGQLLADKRPARDYNRK (SEQ ID NO:48) which is encoded by the nucleic acid sequence SEQ ID NO:45, and more particularly by the nucleic acid sequence SEQ ID NO:54. The present invention therefore provides an isolated nucleic acid encoding a peptide comprising the amino acid sequence of SEQ ID NO:2 with a conservative amino acid substitution. Preferably, the peptide is capable of inhibiting growth of both wild type pneumococci, and a strain of pneumococcus that is autolysin deficient (e.g., either lacking LytA or containing a defective LytA). More preferably, the peptide can inhibit the growth of a vanconycin tolerant bacterial cell. In a particular embodiment the peptide kills autolysis prone pneumococci without lysing the cell. In a preferred embodiment, the peptide acts together with penicillin (or analogues thereof) in a synergistic manner to kill bacterial cells.

In a particular embodiment of this type, the nucleic acid encodes a peptide containing no more than 100 amino acids. In a preferred embodiment of this type, the nucleic acid encodes a peptide that contains no more than 75 amino acids. In another embodiment the nucleic acid encodes a peptide that contains no more than 50 amino acids. In still another embodiment, the nucleic acid encodes a peptide that contains 25 to 35 amino acids. In a preferred embodiment, the nucleic acid encodes a peptide comprising the amino acid sequence of MRKEFHNVLSSGQLLADKRPARDYN (SEQ ID NO:2). In a more preferred embodiment, the nucleic acid comprises the nucleotide sequence of SEQ ID NO:1.

A related aspect of the present invention provides an isolated nucleic acid encoding a peptide comprising the amino acid sequence of SEQ ID NO:4 with a conservative amino acid substitution. Preferably, the peptide is capable of inhibiting the growth of or killing both wild type pneumococci, and a strain of pneumococcus that is autolysin deficient. More preferably, the peptide can inhibit the growth of or kill a vancomycin tolerant bacterial cell. In a particular embodiment the peptide kills autolysis prone pneumococci without lysing the cell. In a preferred embodiment, the peptide acts together with penicillin (or analogues thereof) in a synergistic manner to kill bacterial cells.

In a particular embodiment of this type, the nucleic acid encodes a peptide containing no more than 100 amino acids. In a preferred embodiment of this type, the nucleic acid encodes a peptide that contains no more than 75 amino acids. In another embodiment the nucleic acid encodes a peptide that contains no more than 50 amino acids. In still another embodiment, the nucleic acid encodes a peptide that contains 25 to 35 amino acids. In a preferred embodiment, the nucleic acid encodes a peptide comprising the amino acid sequence of MRKEFHNVLSAGQLLADKRPARDYN (SEQ ID NO:4). In a more preferred embodiment, the nucleic acid comprises the nucleotide sequence of SEQ ID NO:3.

A related aspect of the present invention provides an isolated nucleic acid encoding a peptide comprising the amino acid sequence of SEQ ID NO:44 with a conservative amino acid substitution. Preferably, the peptide is capable of inhibiting the growth of or killing both wild type pneumococci, and a strain of pneumococcus that is autolysin deficient. More preferably, the peptide can inhibit the growth of or kill a vancomycin tolerant bacterial cell. In a particular embodiment the peptide kills autolysis prone pneumococci without lysing the cell. In a preferred embodiment, the peptide acts together with penicillin (or analogues thereof) in a synergistic manner to kill bacterial cells.

In a particular embodiment of this type, the nucleic acid encodes a peptide containing no more than 100 amino acids. In a preferred embodiment of this type, the nucleic acid encodes a peptide that contains no more than 75 amino acids. In another embodiment the nucleic acid encodes a peptide that contains no more than 50 amino acids. In still another embodiment, the nucleic acid encodes a peptide that contains 27 to 40 amino acids. In a preferred embodiment, the nucleic acid encodes a peptide comprising the amino acid sequence of MRKEFHNVLSSGQLLADKRPARDYNRK (SEQ ID NO:44). In a more preferred embodiment, the nucleic acid comprises the nucleotide sequence of SEQ ID NO:53.

In another embodiment the nucleic acid encodes a peptide having the amino acid sequence of MRKEFHNVLSSGQLLADKRPARDXN (SEQ ID NO:36), (where X is any amino acid residue) with a conservative amino acid substitution. This peptide is capable of inhibiting the growth of or killing both wild type pneumococci, and a strain of pneumococcus that is autolysin deficient. Preferably, the peptide can inhibit the growth of or kill a vancomycin tolerant bacterial cell. In a particular embodiment the peptide kills autolysis prone pneumococci without lysing the cell. In a preferred embodiment, the peptide acts together with penicillin (or analogues thereof) in a synergistic manner to kill bacterial cells.

In a particular embodiment of this type, the nucleic acid encodes a peptide containing no more than 100 amino acids. In a preferred embodiment of this type, the nucleic acid encodes a peptide that contains no more than 75 amino acids. In another embodiment the nucleic acid encodes a peptide that contains no more than 50 amino acids. In still another embodiment, the nucleic acid encodes a peptide that contains 25 to 35 amino acids. In a preferred embodiment, the nucleic acid encodes a peptide comprising the amino acid sequence of MRKEFHNVLSSGQLLADKRPARDXN (SEQ ID NO:36).

The present invention also provides a nucleic acid encoding a peptide containing 7 to 100 amino acids that comprises three contiguous amino acids from the amino acid sequence of SEQ ID NO:2, wherein the peptide is capable of inhibiting the growth of or killing both wild type pneumococci, and a strain of pneumococcus that is autolysin deficient. Preferably, the peptide can inhibit the growth of or kill a vancomycin tolerant bacterial cell. In a particular embodiment the peptide kills autolysis prone pneumococci without lysing the cell. In a preferred embodiment, the peptide acts together with penicillin (or analogues thereof) in a synergistic manner to kill bacterial cells.

In one such embodiment the nucleic acid encodes a peptide that contains 12 to 50 amino acids. In another embodiment, the nucleic acid encodes a peptide that contains 17 to 35 amino acids. In a preferred embodiment of this type, the nucleic acid encodes a peptide having 20 to 30 amino acids. In a more preferred embodiment, the nucleic acid encodes a peptide having 25 amino acids.

The present invention further provides a nucleic acid encoding a peptide containing 7 to 100 amino acids that comprises five contiguous amino acids from the amino acid sequence of SEQ ID NO:2, wherein the peptide is capable of inhibiting the growth of or killing both wild type pneumococci, and a strain of pneumococcus that is autolysin deficient. Preferably, the peptide can inhibit the growth of or kill a vancomycin tolerant bacterial cell. In a particular embodiment the peptide kills autolysis prone pneumococci without lysing the cell. In a preferred embodiment, the peptide acts together with penicillin (or analogues thereof) in a synergistic manner to kill bacterial cells.

In one such embodiment the nucleic acid encodes a peptide that contains 12 to 50 amino acids. In another embodiment, the nucleic acid encodes a peptide that contains 17 to 35 amino acids. In a preferred embodiment of this type, the nucleic acid encodes a peptide having 20 to 30 amino acids. In a more preferred embodiment, the nucleic acid encodes a peptide having 25 amino acids.

The present invention further provides a nucleic acid encoding a peptide containing 7 to 100 amino acids that comprises seven contiguous amino acids from the amino acid sequence of SEQ ID NO:2, wherein the peptide is capable of inhibiting the growth of or killing both wild type pneumococci, and a strain of pneumococcus that is autolysin deficient. Preferably, the peptide can inhibit the growth of or kill a vancomycin tolerant bacterial cell. In a particular embodiment the peptide kills autolysis prone pneumococci without lysing the cell. In a preferred embodiment, the peptide acts together with penicillin (or analogues thereof) in a synergistic manner to kill bacterial cells.

In one such embodiment the nucleic acid encodes a peptide that contains 12 to 50 amino acids. In another embodiment, the nucleic acid encodes a peptide that contains 17 to 35 amino acids. In a preferred embodiment of this type, the nucleic acid encodes a peptide having 20 to 30 amino acids. In a more preferred embodiment, the nucleic acid encodes a peptide having 25 amino acids.

The present invention further provides a nucleic acid encoding a peptide containing 12 to 100 amino acids that comprises twelve contiguous amino acids from the amino acid sequence of SEQ ID NO:2, wherein the peptide is capable of inhibiting the growth of or killing both wild type pneumococci, and a strain of pneumococcus that is autolysin deficient. Preferably, the peptide can inhibit the growth of or kill a vancomycin tolerant bacterial cell. In a particular embodiment the peptide kills autolysis prone pneumococci without lysing the cell. In a preferred embodiment, the peptide acts together with penicillin (or analogues thereof) in a synergistic manner to kill bacterial cells.

In one such embodiment the nucleic acid encodes a peptide that contains 16 to 50 amino acids. In another embodiment, the nucleic acid encodes a peptide that contains 20 to 35 amino acids. In a preferred embodiment of this type, the nucleic acid encodes a peptide having 22 to 28 amino acids. In a more preferred embodiment, the nucleic acid encodes a peptide having 25 amino acids.

The present invention also provides a nucleic acid encoding a peptide containing 8 to 100 amino acids, and comprising the amino acid sequence of

DKRPARDY (SEQ ID NO:40)

or the amino acid sequence of DKRPARDY (SEQ ID NO:40) having a conservative amino acid substitution, wherein the peptide is capable of inhibiting the growth of or killing both wild type pneumococci, and a strain of pneumococcus that is autolysin deficient. Preferably, the peptide can inhibit the growth of or kill a vancomycin tolerant bacterial cell. In a particular embodiment the peptide kills autolysis prone pneumococci without lysing the cell. In a preferred embodiment, the peptide acts together with penicillin (or analogues thereof) in a synergistic manner to kill bacterial cells.

In one such embodiment the nucleic acid encodes a peptide that contains 12 to 50 amino acids. In another embodiment, the nucleic acid encodes a peptide that contains 17 to 35 amino acids. In a preferred embodiment of this type, the nucleic acid encodes a peptide having 20 to 30 amino acids. In a more preferred embodiment, the nucleic acid encodes a peptide having 25 amino acids.

The present invention also provides a nucleic acid encoding a peptide containing 7 to 100 amino acids and comprising the amino acid sequence of

RKEFHNV (SEQ ID NO:41)

or the amino acid sequence of RKEFHNV (SEQ ID NO:41) having a conservative amino acid substitution, wherein the peptide is capable of inhibiting the growth of or killing both wild type pneumococci, and a strain of pneumococcus that is autolysin deficient. Preferably, the peptide can inhibit the growth of or kill a vancomycin tolerant bacterial cell. In a particular embodiment the peptide kills autolysis prone pneumococci without lysing the cell. In a preferred embodiment, the peptide acts together with penicillin (or analogues thereof) in a synergistic manner to kill bacterial cells.

In one such embodiment the nucleic acid encodes a peptide that contains 12 to 50 amino acids. In another embodiment, the nucleic acid encodes a peptide that contains 17 to 35 amino acids. In a preferred embodiment of this type, the nucleic acid encodes a peptide having 20 to 30 amino acids. In a more preferred embodiment, the nucleic acid encodes a peptide having 25 amino acids.

The present invention also provides a nucleic acid encoding a peptide containing 7 to 100 amino acids and comprising the amino acid sequence of

LSSGQLL (SEQ ID NO:42)

or the amino acid sequence of LSSGQLL (SEQ ID NO:42) having a conservative amino acid substitution, wherein the peptide is capable of inhibiting the growth of or killing both wild type pneumococci, and a strain of pneumococcus that is autolysin deficient. Preferably, the peptide can inhibit the growth of or kill a vancomycin tolerant bacterial cell. In a particular embodiment the peptide kills autolysis prone pneumococci without lysing the cell. In a preferred embodiment, the peptide acts together with penicillin (or analogues thereof) in a synergistic manner to kill bacterial cells.

In one such embodiment the nucleic acid encodes a peptide that contains 12 to 50 amino acids. In another embodiment, the nucleic acid encodes a peptide that contains 17 to 35 amino acids. In a preferred embodiment of this type, the nucleic acid encodes a peptide having 20 to 30 amino acids. In a more preferred embodiment, the nucleic acid encodes a peptide having 25 amino acids.

The present invention also provides a nucleic acid encoding a peptide containing 23 to 100 amino acids and comprising the amino acid sequence of RKEFHXXXXXXQLLXDKRPXRDY, (SEQ ID NO:39) (where X can be any amino acid) or this amino acid sequence having a conservative amino acid substitution, wherein the peptide is capable of inhibiting the growth of or killing both wild type pneumococci, and a strain of pneumococcus that is autolysin deficient. Preferably, the peptide can inhibit the growth of or kill a vancomycin tolerant bacterial cell. In a particular embodiment the peptide kills autolysis prone pneumococci without lysing the cell. In a preferred embodiment, the peptide acts together with penicillin (or analogues thereof) in a synergistic manner to kill bacterial cells.

In a particular embodiment of this type, the nucleic acid encodes a peptide that contains no more than 75 amino acids. In another such embodiment the nucleic acid encodes a peptide that contains no more than 50 amino acids. In still another such embodiment, the nucleic acid encodes a peptide that contains 25 to 35 amino acids.

The present invention further provides a nucleic acid encoding a peptide containing 25 to 100 amino acids and comprising an amino acid sequence of

MXXXXXNVLSXGXXXAXXXXAXXXN (SEQ ID NO:43 or this amino acid sequence having a conservative amino acid substitution, wherein the peptide is capable of inhibiting the growth of or killing both wild type pneumococci, and a strain of pneumococcus that is autolysin deficient. Preferably, the peptide can inhibit the growth of or kill a vancomycin tolerant bacterial cell. In a particular embodiment the peptide kills autolysis prone pneumococci without lysing the cell. In a preferred embodiment, the peptide acts together with penicillin (or analogues thereof) in a synergistic manner to kill bacterial cells.

In a particular embodiment of this type, the nucleic acid encodes a peptide that contains no more than 75 amino acids. In another such embodiment the nucleic acid encodes a peptide that contains no more than 50 amino acids. In still another such embodiment, the nucleic acid encodes a peptide that contains 25 to 35 amino acids.

The present invention further provides nucleic acids encoding the components of the His-Asp phosphorelay pathway and ABC transporter system of the present invention. In one such embodiment, the nucleic acid encodes a histidine kinase having the amino acid sequence of SEQ ID NO:14. In another embodiment the nucleic acid encodes a homologue of that histidine kinase. In still another embodiment the nucleic acid encodes a histidine kinase having the amino acid sequence of SEQ ID NO:14 with a conservative amino acid substitution. In a particular embodiment the nucleic acid has the nucleotide sequence of SEQ ID NO:13. In another embodiment, the nucleic acid encodes a response regulator having the amino acid sequence of SEQ ID NO:16. In another embodiment the nucleic acid encodes a homologue of that response regulator. In yet another embodiment the nucleic acid encodes a response regulator having the amino acid sequence of SEQ ID NO:16 with a conservative amino acid substitution. In a particular embodiment, the nucleic acid has the nucleotide sequence of SEQ ID NO:15.

In a related embodiment, the present invention provides a nucleic acid encoding a component of an ABC transporter system. In one such embodiment the nucleic acid encodes a component having the amino acid sequence of SEQ ID NO:18. In another embodiment, the component is a homologue of that component. In still another embodiment the nucleic acid encodes a component having the amino acid sequence of SEQ ID NO:18 with a conservative amino acid substitution. In a particular embodiment, the nucleic acid has the nucleotide sequence of SEQ ID NO:17. In another embodiment, the nucleic acid encodes a component of the ABC transporter system having the amino acid sequence of SEQ ID NO:20. In another embodiment, the component is a homologue of that component. In yet another embodiment, the nucleic acid encodes a component having the amino acid sequence of SEQ ID NO:20 with a conservative amino acid substitution. In a particular embodiment, the nucleic acid has the nucleotide sequence of SEQ ID NO:19. In another embodiment, the nucleic acid encodes a component of the ABC transporter system having the amino acid sequence of SEQ ID NO:22. In still another embodiment, the component is a homologue of that component. In yet another embodiment, the nucleic acid encodes a component having the amino acid sequence of SEQ ID NO:22 with a conservative amino acid substitution. In a particular embodiment, the nucleic acid has the nucleotide sequence of SEQ ID NO:21. In another embodiment, the nucleic acid has the nucleotide sequence of SEQ ID NO:23. All of the nucleic acids of the present invention can also contain an heterologous nucleotide sequence.

The nucleic acids encoding the peptides and proteins of the present invention can be either RNA or DNA. Cloning vectors that comprise such DNAs are therefore also included.

Similarly, expression vectors which comprise DNA encoding the peptides or proteins of the present invention, and which are operatively associated with an expression control sequence, are also included. In addition, the present invention contains unicellular hosts that are transfected or transformed with the expression vectors of the present invention. In one such embodiment the unicellular host is a bacterium. The present invention also includes mammalian cells transfected or transformed with the expression vector of the present invention. The present invention further includes method of isolating the peptides and proteins of the present invention prepared by the recombinant methods described herein. Further included in the present invention are the recombinant peptides and proteins isolated by such procedures.

Another aspect of the present invention provides a peptide containing no more than 100 amino acids and comprising the amino acid sequence of SEQ ID NO:2 with a conservative amino acid substitution. Preferably, the peptide is capable of inhibiting the growth of or killing both wild type pneumococci, and a strain of pneumococcus that is autolysin deficient. More preferably, the peptide can inhibit the growth of or kill a vancomycin tolerant bacterial cell. In a particular embodiment the peptide kills autolysis prone pneumococci without lysing the cell. In a preferred embodiment, the peptide acts together with penicillin (or analogues thereof) in a synergistic manner to kill bacterial cells.

In a particular embodiment of this type, the peptide contains no more than 75 amino acids. In another embodiment the peptide contains no more than 50 amino acids. In still another embodiment, the peptide contains 25 to 35 amino acids. In preferred embodiment, the peptide comprises the amino acid sequence of SEQ ID NO:2.

A related aspect of the present invention provides a peptide comprising the amino acid sequence of SEQ ID NO:4 with a conservative amino acid substitution. Preferably, the peptide is capable of inhibiting the growth of or killing both wild type pneumococci, and a strain of pneumococcus that is autolysin deficient. More preferably, the peptide can inhibit the growth of or kill a vancomycin tolerant bacterial cell. In a particular embodiment the peptide kills autolysis prone pneumococci without lysing the cell. In a preferred embodiment, the peptide acts together with penicillin (or analogues thereof) in a synergistic manner to kill bacterial cells.

In a particular embodiment of this type, the peptide contains no more than 100 amino acids. In a preferred embodiment of this type, the peptide contains no more than 75 amino acids. In another embodiment the peptide contains no more than 50 amino acids. In still another embodiment, the peptide contains 25 to 35 amino acids. In a preferred embodiment, the peptide comprises the amino acid sequence of SEQ ID NO:4.

Another related aspect of the present invention provides a peptide comprising the amino acid sequence of SEQ ID NO:44 with a conservative amino acid substitution. Preferably, the peptide is capable of inhibiting the growth of or killing both wild type pneumococci, and a strain of pneumococcus that is autolysin deficient. More preferably, the peptide can inhibit the growth of or kill a vancomycin tolerant bacterial cell. In a particular embodiment the peptide kills autolysis prone pneumococci without lysing the cell. In a preferred embodiment, the peptide acts together with penicillin (or analogues thereof) in a synergistic manner to kill bacterial cells.

In a particular embodiment of this type, the peptide contains no more than 100 amino acids. In a preferred embodiment of this type, the peptide contains no more than 75 amino acids. In another embodiment the peptide contains no more than 50 amino acids. In still another embodiment, the peptide contains 27 to 40 amino acids. In a preferred embodiment, the peptide comprises the amino acid sequence of SEQ ID NO:44.

In another embodiment the present invention provides a peptide having the amino acid sequence of MRKEFHNVLSSGQLLADKRPARDXN (SEQ ID NO:36), (where X is any amino acid residue) with a conservative amino acid substitution. This peptide is capable of inhibiting the growth of or killing both wild type pneumococci, and a strain of pneumococcus that is autolysin deficient. Preferably, the peptide can inhibit the growth of or kill a vancomycin tolerant bacterial cell. In a particular embodiment the peptide kills autolysis prone pneumococci without lysing the cell. In a preferred embodiment, the peptide acts together with penicillin (or analogues thereof) in a synergistic manner to kill bacterial cells.

In a particular embodiment of this type, the peptide contains no more than 100 amino acids. In a preferred embodiment of this type, the peptide contains no more than 75 amino acids. In another embodiment the peptide contains no more than 50 amino acids. In still another embodiment, the peptide contains 25 to 35 amino acids. In a preferred embodiment, the peptide comprises the amino acid sequence of MRKEFHNVLSSGQLLADKRPARDXN (SEQ ID NO:36).

The present invention also provides a peptide containing 7 to 100 amino acids that comprises three contiguous amino acids from the amino acid sequence of SEQ ID NO:2, wherein the peptide is capable of inhibiting the growth of or killing both wild type pneumococci, and a strain of pneumococcus that is autolysin deficient. Preferably, the peptide can inhibit the growth of or kill a vancomycin tolerant bacterial cell. In a particular embodiment the peptide kills autolysis prone pneumococci without lysing the cell. In a preferred embodiment, the peptide acts together with penicillin (or analogues thereof) in a synergistic manner to kill bacterial cells.

In one such embodiment the peptide contains 12 to 50 amino acids. In another embodiment, the peptide contains 17 to 35 amino acids. In a preferred embodiment of this type, the peptide has 20 to 30 amino acids. In a more preferred embodiment, the peptide has 25 amino acids.

The present invention further provides a peptide containing 7 to 100 amino acids that comprises five contiguous amino acids from the amino acid sequence of SEQ ID NO:2, wherein the peptide is capable of inhibiting the growth of or killing both wild type pneumococci, and a strain of pneumococcus that is autolysin deficient. Preferably, the peptide can inhibit the growth of or kill a vancomycin tolerant bacterial cell. In a particular embodiment the peptide kills autolysis prone pneumococci without lysing the cell. In a preferred embodiment, the peptide acts together with penicillin (or analogues thereof) in a synergistic manner to kill bacterial cells.

In one such embodiment the peptide contains 12 to 50 amino acids. In another embodiment, the peptide contains 17 to 35 amino acids. In a preferred embodiment of this type, the peptide has 20 to 30 amino acids. In a more preferred embodiment, the peptide has 25 amino acids.

The present invention further provides a peptide containing 7 to 100 amino acids that comprises seven contiguous amino acids from the amino acid sequence of SEQ ID NO:2, wherein the peptide is capable of inhibiting the growth of or killing both wild type pneumococci, and a strain of pneumococcus that is autolysin deficient. Preferably, the peptide can inhibit the growth of or kill a vancomycin tolerant bacterial cell. In a particular embodiment the peptide kills autolysis prone pneumococci without lysing the cell. In a preferred embodiment, the peptide acts together with penicillin (or analogues thereof) in a synergistic manner to kill bacterial cells.

In one such embodiment the peptide contains 12 to 50 amino acids. In another embodiment, the peptide contains 17 to 35 amino acids. In a preferred embodiment of this type, the peptide has 20 to 30 amino acids. In a more preferred embodiment, the peptide has 25 amino acids.

The present invention further provides a peptide containing 12 to 100 amino acids that comprises twelve contiguous amino acids from the amino acid sequence of SEQ ID NO:2, wherein the peptide is capable of inhibiting the growth of or killing both wild type pneumococci, and a strain of pneumococcus that is autolysin deficient. Preferably, the peptide can inhibit the growth of or kill a vancomycin tolerant bacterial cell. In a particular embodiment the peptide kills autolysis prone pneumococci without lysing the cell. In a preferred embodiment, the peptide acts together with penicillin (or analogues thereof) in a synergistic manner to kill bacterial cells.

In one such embodiment the peptide contains 16 to 50 amino acids. In another embodiment, the peptide contains 20 to 35 amino acids. In a preferred embodiment of this type, the peptide has 22 to 28 amino acids. In a more preferred embodiment, the peptide has 25 amino acids.

The present invention also provides a peptide containing 8 to 100 amino acids, and comprising the amino acid sequence of

DKRPARDY (SEQ ID NO:40)

or the amino acid sequence of DKRPARDY (SEQ ID NO:40) having a conservative amino acid substitution, wherein the peptide is capable of inhibiting the growth of or killing both wild type pneumococci, and a strain of pneumococcus that is autolysin deficient. Preferably, the peptide can inhibit the growth of or kill a vancomycin tolerant bacterial cell. In a particular embodiment the peptide kills autolysis prone pneumococci without lysing the cell. In a preferred embodiment, the peptide acts together with penicillin (or analogues thereof) in a synergistic manner to kill bacterial cells.

In one such embodiment the peptide contains 12 to 50 amino acids. In another embodiment, the peptide contains 17 to 35 amino acids. In a preferred embodiment of this type, the peptide has 20 to 30 amino acids. In a more preferred embodiment, the peptide has 25 amino acids.

The present invention also provides a peptide containing 7 to 100 amino acids and comprises the amino acid sequence of

RKEFHNV (SEQ ID NO:41)

or the amino acid sequence of RKEFfINV (SEQ ID NO:41) having the conservative amino acid substitution, wherein the peptide is capable of inhibiting the growth of or killing both wild type pneumococci, and a strain of pneumococcus that is autolysin-deficient. Preferably, the peptide can inhibit the growth of or kill a vancomycin tolerant bacterial cell. In a particular embodiment the peptide kills autolysis prone pneumococci without lysing the cell. In a preferred embodiment, the peptide acts together with penicillin (or analogues thereof) in a synergistic manner to kill bacterial cells.

In one such embodiment the peptide contains 12 to 50 amino acids. In another embodiment, the peptide contains 17 to 35 amino acids. In a preferred embodiment of this type, the peptide has 20 to 30 amino acids. In a more preferred embodiment, the peptide has 25 amino acids.

The present invention also provides a peptide containing 7 to 100 amino acids and comprises the amino acid sequence of

LSSGQLL (SEQ ID NO:42)

or the amino acid sequence of LSSGQLL (SEQ ID NO:42) having a conservative amino acid substitution, wherein the peptide is capable of inhibiting the growth of or killing both wild type pneumococci, and a strain of pneumococcus that is autolysin deficient. Preferably, the peptide can inhibit the growth of or kill a vancomycin tolerant bacterial cell. In a particular embodiment the peptide kills autolysis prone pneumococci without lysing the cell. In a preferred embodiment, the peptide acts together with penicillin (or analogues thereof) in a synergistic manner to kill bacterial cells.

In one such embodiment the peptide contains 12 to 50 amino acids. In another embodiment, the peptide contains 17 to 35 amino acids. In a preferred embodiment of this type, the peptide has 20 to 30 amino acids. In a more preferred embodiment, the peptide has 25 amino acids.

The present invention also provides a peptide containing 23 to 100 amino acids and comprising the amino acid sequence of

RKEFHXXXXXXQLLXDKRPXRDY (SEQ ID NO:39)

or this amino acid sequence having a conservative amino acid substitution, wherein the peptide is capable of inhibiting the growth of or killing both wild type pneumococci, and a strain of pneumococcus that is autolysin deficient. Preferably, the peptide can inhibit the growth of or kill a vancomycin tolerant bacterial cell. In a particular embodiment the peptide kills autolysis prone pneumococci without lysing the cell. In a preferred embodiment, the peptide acts together with penicillin (or analogues thereof) in a synergistic manner to kill bacterial cells.

In a particular embodiment of this type, the peptide contains no more than 75 amino acids. In another such embodiment the peptide contains no more than 50 amino acids. In still another such embodiment, the peptide that contains 25 to 35 amino acids.

The present invention further provides a peptide containing 25 to 100 amino acids and comprising the amino acid sequence of

MXXXXXNVLSXGXXXAXXXXAXXXN (SEQ ID NO:43)

or this amino acid sequence having a conservative amino acid substitution, wherein the peptide is capable of inhibiting the growth of or killing both wild type pneumococci, and a strain of pneumococcus that is autolysin deficient. Preferably, the peptide can inhibit the growth of or kill a vancomycin tolerant bacterial cell. In a particular embodiment the peptide kills autolysis prone pneumococci without lysing the cell. In a preferred embodiment, the peptide acts together with penicillin (or analogues thereof) in a synergistic manner to kill bacterial cells.

In a particular embodiment of this type, the peptide contains no more than 75 amino acids. In another such embodiment the peptide contains no more than 50 amino acids. In still another such embodiment, the peptide contains 25 to 35 amino acids.

The present invention further provides the components of the His-Asp phosphorelay pathway and ABC transporter system of the present invention. One such embodiment is a histidine kinase having the amino acid sequence of SEQ ID NO:14. Another embodiment is a homologue of that histidine kinase. Still another embodiment is a histidine kinase having the amino acid sequence of SEQ ID NO:14 with a conservative amino acid substitution. Another such embodiment is a response regulator having the amino acid sequence of SEQ ID NO:16.

Still another embodiment is a homologue of that response regulator. Yet another embodiment is a response regulator having the amino acid sequence of SEQ ID NO:16 with a conservative amino acid substitution.

In a related embodiment, the present invention provides a component of an ABC transporter system One such embodiment is a component having the amino acid sequence of SEQ ID NO:18. Another embodiment is a component that is a homologue of the component having the amino acid sequence of SEQ ID NO:18. Still another embodiment is a component having the amino acid sequence of SEQ ID NO:18 with a conservative amino acid substitution. Another embodiment is a component of the ABC transporter system having the amino acid sequence of SEQ ID NO:20. Still another embodiment is a homologue of the component having an amino acid sequence of SEQ ID NO:20. Yet another embodiment is a component having the amino acid sequence of SEQ ID NO:20 with a conservative amino acid substitution. Still another embodiment is a component of the ABC transporter system having the amino acid sequence of SEQ ID NO:22. Yet another embodiment is a component that is a homologue of the component having the amino acid sequence of SEQ ID NO:22. Yet another embodiment is a component having the amino acid sequence of SEQ ID NO:22 with a conservative amino acid substitution.

All of the proteins of the present invention can also be formed into fusion proteins or chimeric proteins. Fragments (e.g. by proteolytic digestion such as by trypsin) of these proteins are also part of the present invention.

The present invention also provides antibodies raised against any of the proteins or peptides of the present invention. In one such embodiment the antibody is raised against a peptide containing no more than 100 amino acids and comprising the amino acid sequence of SEQ ID NO:2 or SEQ ID NO:2 with a conservative amino acid substitution. In a particular embodiment of this type, the antibody is raised against a peptide containing no more than 100 amino acids and comprising the amino acid sequence of SEQ ID NO:44 with a conservative amino acid substitution. Preferably the peptide can inhibit the growth of or kill both wild type pneumococci, and a strain of pneumococcus that is autolysin deficient. More preferably, the peptide can inhibit the growth of or kill a vancomycin tolerant bacterial cell. In a particular embodiment the peptide kills autolysis prone pneumococci without lysing the cell. In a preferred embodiment, the peptide acts together with penicillin (or analogues thereof) in a synergistic manner to kill bacterial cells.

In a preferred embodiment of this type, the antibody is raised against the peptide having the amino acid sequence of SEQ ID NO:2 or SEQ ID NO:44. In a related embodiment, the antibody is raised against a fragment of 6 to 18 contiguous amino acids of the peptide having the amino acid sequence of SEQ ID NO:2. In yet another embodiment, the antibody is raised against the histidine kinase having the amino acid sequence of SEQ ID NO:14, or raised against a fragment thereof.

The antibodies of the present invention can be either polyclonal or monoclonal antibodies, including chimeric antibodies. One embodiment includes an immortal cell line that produces a monoclonal antibody raised against a peptide of the present invention. In a preferred embodiment of this type the monoclonal antibody is raised against a peptide comprising the amino acid sequence of SEQ ID NO:2, or a fragment thereof. In another embodiment, the monoclonal antibody is raised against the response regulator having the amino acid sequence of SEQ ID NO:16, or raised against a fragment thereof.

The present invention further provides pharmaceutical compositions for treating a bacterial infection comprising one or more of the peptides of the present invention, and a pharmaceutically acceptable carrier. Any of the peptides disclosed herein can be used in such pharmaceutical compositions. In one such embodiment, the pharmaceutical composition comprises a peptide having the amino acid sequence of SEQ ID NO:2, and a pharmaceutically acceptable carrier. In another embodiment, the pharmaceutical composition comprises a peptide having the amino acid sequence of SEQ ID NO:44, and a pharmaceutically acceptable carrier. In a related embodiment, the pharmaceutical composition can further comprise a second antibiotic such as penicillin, or multiple antibiotics and/or peptides.

The present invention further provides methods of treating or preventing bacterial infections or inflammations comprising administering a pharmaceutical composition of the present invention. Such administration can be performed by any number of means including topically, by injection, or orally.

Still another aspect of the present invention provides methods for identifying peptides that can inhibit the growth of and/or kill a strain of bacteria. In a particular embodiment the peptide kills autolysis prone pneumococci without lysing the cell. In a preferred embodiment, the peptide acts together with penicillin (or analogues thereof) in a synergistic manner to kill bacterial cells.

One such method comprises locating an open reading frame in a gene cluster of a prokaryotic or fungal DNA which encodes two or more components involved in an His-Asp phosphorelay signal transduction system. Preferably the gene cluster is next to another gene cluster encoding one or more components of an ABC transporter system. In another such embodiment, an open reading frame is located in a gene cluster of a prokaryotic or fungal DNA which encodes two or more components of an ABC transporter system. In the Examples below, the DNA is obtained from a bacterial genome. In a particular embodiment the gene cluster encodes at least one of the following: a sensor histidine kinase, or a response regulator. In a preferred embodiment of this type, the histidine kinase is a homologue of the histidine kinase having the amino acid sequence of SEQ ID NO:14. In another embodiment, the response regulator is a homologue of the response regulator having the amino acid sequence of SEQ ID NO:16. In still another embodiment the component of the ABC transporter system is a homologue of the component having the amino acid sequence of SEQ ID NO:18. In a related embodiment the component of the ABC transporter system is a homologue of the component having the amino acid sequence of SEQ ID NO:20. In another embodiment, the component of the ABC transporter system is a homologue of the component having the amino acid sequence of SEQ ID NO:22.

The method can further comprise making the peptide which is encoded by the open reading frame, or a peptide analog thereof, and then testing the peptide for its ability to inhibit the growth of or kill the strain of bacteria. In a particular embodiment the peptide kills autolysis prone pneumococci without lysing the cell. In a preferred embodiment, the peptide acts together with penicillin (or analogues thereof) in a synergistic manner to kill bacterial cells.

In one such embodiment a particular peptide, or analog thereof is identified when it can inhibit the growth of and/or kill a bacterial or fungal cell. In another such embodiment, the peptide can kill bacteria without lysis. In a preferred embodiment, the peptide can act synergistically with penicillin to kill cells.

The peptides of the present invention can be prepared through recombinant means, proteolytic digestions, or preferably chemical synthesis. Analogs of the peptides can, for example, contain portions of the amino acid sequence encoded by the open reading frame alone, or alternatively a portion of the amino acid sequence can be linked together in a fusion peptide/protein. Thus, modification of the peptides of the present invention can also be made in order to make the peptide more stable, or more potent etc. Such modifications may include the use of unnatural amino acids as described below.

The method for identifying peptides that can inhibit the growth of and/or kill a strain of bacteria can further comprise testing the peptide for its ability to inhibit the growth of and/or kill an alternative strain (or species) of a bacterium, including a vancomycin tolerant strain. In a particular embodiment, the peptide is identified when it can inhibit the growth of and/or kill both strains of the bacterium In one such embodiment, one strain is a wild type strain, and the other strain is a corresponding mutant strain. In a preferred embodiment of this type, the mutant strain lacks an autolysin or contains a defective autolysin. In one such embodiment, the autolysin (e.g., the missing or defective autolysin) is LytA. In a preferred embodiment, the bacterium is a *Streptococcus pneumoniae*.

The present invention further provides alternative methods of identifying a peptide that can kill a wild type strain of bacterium. In a particular embodiment the peptide kills autolysis prone pneumococci without lysing the cell. In a preferred embodiment, the peptide acts together with penicillin (or analogs thereof) in a synergistic manner to kill bacterial cells.

One such embodiment comprises locating an open reading frame in a bacterial genome which is within three kilobases of another open reading frame which encodes an ABC transporter system The peptide encoded by the open reading frame is obtained, (e.g., made by peptide synthesis or through the expression of a recombinant nucleic acid encoding the peptide or alternatively isolated from its natural source), and then tested for its ability to inhibit the growth of and/or kill a wild type strain of a bacterium The peptide is identified when it can inhibit the growth of and/or kill the bacterium.

In a preferred embodiment of this type the open reading frame encoding the peptide is within one kilobase of the open reading frame which encodes a component of an ABC transporter system In a more preferred embodiment the open reading frame encoding the peptide is within 500 bases of the open reading frame which encodes a component of an ABC transporter system In an even more preferred embodiment the peptide is co-transcribed with a component of the ABC transporter system In a particular embodiment, the component of the ABC transporter system is a homologue of the ABC transporter having the amino acid sequence of SEQ ID NO:18. In another embodiment, the component of the ABC transporter system is a homologue of the ABC transporter having the amino acid sequence of SEQ ID NO:20. In yet another embodiment, the component of the ABC transporter system is a homologue of the ABC transporter having the amino acid sequence of SEQ ID NO:22.

In a related embodiment the open reading frame encoding the peptide is also within three kilobases of an open reading frame that encodes a component involved in the His-Asp phosphorelay signal transduction system In one such embodiment the component involved in the His-Asp phosphorelay signal transduction system is a sensor histidine kinase. In a particular embodiment the sensor histidine kinase is a homologue to the sensor histidine kinase having the amino acid sequence of SEQ ID NO:14. In another such embodiment the component involved in the His-Asp phosphorelay signal transduction system is a response regulator. In a particular embodiment, the response regulator is a homologue of the response regulator having the amino acid sequence of SEQ ID NO:16.

In a preferred embodiment of this type the open reading frame encoding the peptide is within one kilobase of the open reading frame which encodes a component involved in the His-Asp phosphorelay signal transduction system. In a more preferred embodiment the open reading frame encoding the peptide is within 500 bases of the open reading frame which encodes a component involved in the His-Asp phosphorelay signal transduction system. In an alternative embodiment the peptide is co-transcribed with a component of the His-Asp phosphorelay signal transduction system.

In a particular embodiment the method can further comprise testing the peptide for its ability to inhibit the growth of or kill a strain of bacterium that is deficient in an autolysin. In this case the peptide is identified when it can inhibit the growth of or kill both wild type and the autolysin deficient strain of bacterium. Alternatively, the peptide can be tested for its ability kill autolysis prone pneumococci without lysing the cell. In still another embodiment, the peptide is tested for acting synergistically with penicillin (or analogues thereof) for killing bacterial cells. The peptides can be selected for either killing autolysis prone pneumococci without lysing the cell or for acting synergistically with penicillin or an analogue thereof.

In the methods of the present invention for identifying such peptides candidate peptides can be located in the genome of any prokaryotic or fungal cell and preferably a bacterial cell including but not limited to Pneumococcus, Methanococcus, Haemophilus, Archaeoglobus, Borrelia, Synedrocyptis, Mycobacteria, Staphylococcus, and Enterococcus.

The present invention further provides alternative methods of identifying an agent (or drug) that is capable of inhibiting the growth of and/or killing bacterial cells. Alternatively, the peptide can be tested for its ability kill autolysis prone pneumococci without killing the cell. In still another embodiment, the peptide is tested for acting synergistically with penicillin (or analogues thereof) for killing bacterial cells. One such method includes contacting an agent with a bacterial cell that has a defective His-Asp signaling system and then determining whether the cell stops growing or is killed. An agent (or drug) is identified as being capable of killing a bacterial cell if it kills the bacterial cell or inhibits the growth of the cell. In a preferred embodiment of this type the bacterial cell is a vancomycin tolerant cell. In another preferred embodiment, the defective His-Asp signaling system of the bacterial cell is not inhibited or not killed by a peptide having the amino acid sequence of SEQ ID NO:2. More preferably, the cell is both tolerant to vancomycin, and in addition is not killed or not inhibited by a peptide having the amino acid sequence of SEQ ID NO:2.

As in the methods described above, the cell can be a prokaryotic or fungal cell but is preferably a bacterial cell and is more preferably a pneumococcal cell.

In a particular embodiment the His-Asp signaling system lacks a functional sensor histidine kinase. In a preferred embodiment of this type the sensor histidine kinase has a wild type amino acid sequence of SEQ ID NO:14 or is a homologue thereof. In another embodiment the His-Asp signaling system lacks a functional response regulator. In a preferred embodiment of this type the response regulator has a wild type amino acid sequence of SEQ ID NO:16 or is a homologue thereof. In still another embodiment the His-Asp signaling system lacks both a functional sensor histidine kinase and a functional response regulator.

In a related embodiment the present invention includes a method of identifying an agent that is capable of killing and/or inhibiting the growth of a bacterial cell. Alternatively, the peptide can be tested for its ability to kill autolysis prone pneumococci without lysing the cell. In still another embodiment, the peptide is tested for acting synergistically with penicillin (or analogues thereof) for killing bacterial cells. One such method includes contacting the agent with a bacterial cell that has a defective ABC transporter system and determining whether the cell is inhibited or killed. An agent is identified as being capable of inhibiting the growth of a bacterial cell when the growth of the bacterial cell is inhibited. Similarly, an agent is identified as being capable of killing a bacterial cell when the bacterial cell is killed. In a particular embodiment of this type, the killing of the cell is monitored at about 620 nm (for the optical density of the cell culture) and an agent is identified as being capable of killing a bacterial cell when the optical density at 620 nm of a cell culture is decreased in the presence of an agent. In a preferred embodiment the bacterial cell is a vancomycin tolerant cell. As above, any bacterial cell can be used in this assay but preferably the bacterial cell is a pneumococcal cell.

In one such embodiment the ABC transporter system lacks a functional component that has a wild type amino acid sequence of SEQ ID NO:18 or is a homologue thereof. In another such embodiment the ABC transporter system lacks a functional component that has a wild type amino acid sequence of SEQ ID NO:20 or is a homologue thereof. In still another such embodiment the ABC transporter system lacks a functional component that has a wild type amino acid sequence of SEQ ID NO:22 or is a homologue thereof.

The present invention further includes recombinant bacterial cells that lack one or more of the functional components (e.g., a sensor histidine kinase, response regulator and/or a component of the ABC transporter system) described above.

In one such embodiment the cell has been altered so as to have a defective His-Asp phosphorelay system, and the cell is not killed by a peptide having the amino acid sequence of SEQ ID NO:2. Preferably the cell is a bacterial cell. In a particular embodiment the cell is not killed by penicillin. In another embodiment, the cell is a vancomycin tolerant cell. The bacterial cell can be any bacterial cell including but not limited to Pneumococcus, Methanococcus, Haemophilus, Archaeoglobus, Borrelia, and Syndedrocyptis. Preferably the bacterial cell is a pneumococcal cell. In a particular embodiment the His-Asp phosphorelay pathway of the bacterial cell lacks a functional sensor histidine kinase having a wild type amino acid sequence of SEQ ID NO:14. In another such embodiment the His-Asp phosphorelay pathway lacks a functional response regulator having a wild type amino acid sequence of SEQ ID NO:16.

Alternatively the cell has been altered so as to have a defective ABC transporter system, and the cell is not killed by a peptide having the amino acid sequence of SEQ ID NO:2. Preferably the cell is a bacterial cell. In a particular embodiment the cell is not killed by penicillin. In another embodiment the cell is a vancomycin tolerant cell. Again the bacterial cell can be any bacterial cell including but not limited to Pneumococcus, Methanococcus, Haemophilus, Archaeoglobus, Borrelia, and Syndedrocyptis. Preferably the bacterial cell is a pneumococcal cell. In a particular embodiment the ABC transporter system lacks a functional component having a wild type amino acid sequence of SEQ ID NO:18. In another embodiment the ABC transporter system lacks a functional component having a wild type amino acid sequence of SEQ ID NO:20. In still another embodiment the ABC transporter system lacks a functional component having a wild type amino acid sequence of SEQ ID NO:22.

The present invention also provides a method of identifying a cell that contains a mutation in a histidine kinase gene. One such embodiment comprises preparing a PCR amplification product for a nucleic acid using a primer for the histidine kinase gene and comparing the PCR amplification product with a control amplification product prepared using the primer and a control nucleic acid encoding the wild type amino acid sequence of the histidine kinase. When the comparing indicates a difference, the cell is identified as containing a mutation in the histidine kinase gene. In a particular embodiment the nucleic acid is obtained from the pneumococcal cell. Preferably the control nucleic acid encodes the amino acid sequence of SEQ ID NO:14. More preferably the control nucleic acid has the nucleotide sequence of SEQ ID NO:13. In one such embodiment the comparing includes the evaluating of the PCR amplification products by single strand conformation polymorphism (SSCP). In another such embodiment the comparing is performed by Restriction Fragment Length Polymorphism (RFLP). In one embodiment the cell is a vancomycin tolerant cell. In a preferred embodiment the cell is a pneumococcal cell.

The present invention also provides a method of identifying a cell that contains a mutation in a response regulator gene. One such embodiment comprises preparing a PCR amplification product for a nucleic acid using a primer for the response regulator gene and comparing the PCR amplification product with a control amplification product prepared using the primer and a control nucleic acid encoding the wild type amino acid sequence of the response regulator. When the comparing indicates a difference, the cell is identified as containing a mutation in the response regulator gene. In a particular embodiment the nucleic acid is obtained from the pneumococcal cell. Preferably the control nucleic acid encodes the amino acid sequence of SEQ ID NO:16. More preferably the control nucleic acid has the nucleotide sequence of SEQ ID NO:15. In one such embodiment the comparing includes the evaluating of the PCR amplification products by single strand conformation polymorphism (SSCP). In another such embodiment the comparing is performed by Restriction Fragment Length Polymorphism (RFLP). In one embodiment the cell is a vancomycin tolerant cell. In a preferred embodiment the cell is a pneumococcal cell.

The present invention also provides a method of identifying a cell that contains a mutation in a component of a gene for the ABC transporter system One such embodiment comprises preparing a PCR amplification product for a nucleic acid using a primer for the component gene and comparing the PCR amplification product with a control amplification product prepared using the primer and a control nucleic acid encoding the wild type component sequence. When the comparing indicates a difference, the cell is identified as containing a mutation in a gene for a component of the ABC transporter system In a particular embodiment the nucleic acid is obtained from the pneumococcal cell. Preferably the control nucleic acid encodes the amino acid sequence of SEQ ID NO:18. More preferably the control nucleic acid has the nucleotide sequence of SEQ ID NO:17. Alternatively the control nucleic acid encodes the amino acid sequence of SEQ ID NO:20 and more preferably the control nucleic acid has the nucleotide sequence of SEQ ID NO:19. In another embodiment the control nucleic acid encodes the amino acid sequence of SEQ ID NO:22 and more preferably the control nucleic acid has the nucleotide sequence of SEQ ID or of SEQ ID NO:23. In one such embodiment the comparing includes the evaluating of the PCR amplification products by single strand conformation polymorphism (SSCP). In another such embodiment the comparing is performed by Restriction Fragment Length Polymorphism (RFLP). In one embodiment the cell is a vancomycin tolerant cell. In a preferred embodiment the cell is a pneumococcal cell.

In addition, the present invention further includes all of the peptides, agents (or drugs) identified by the methods of the present invention.

Accordingly, it is a principal object of the present invention to provide a novel peptide antibiotic.

It is a further object of the present invention to provide a peptide that acts synergistically with antibiotics that are active against bacterial cell walls.

More particularly it is a further object of the present invention to provide a peptide that acts synergistically with penicillin to kill slow growing or non-growing bacterial cells.

It is a further object of the present invention to provide a method of identifying new peptide antibiotics by inspection of bacterial genomes.

It is a further object of the present invention to provide methods of testing putative peptide antibiotics to identify new agents useful in preventing bacterial proliferation and/or causing bacterial cell death or lysis.

It is a further object of the present invention to provide nucleic acids encoding the peptides of the present invention.

It is a further object of the present invention to provide an antibody specific for a peptide of the present invention.

It is a further object of the present invention to provide a method of producing a peptide of the present invention, including by chemical synthesis, and through recombinant technology.

It is a further object of the present invention to provide a method of designing putative peptide antibiotics through altering the amino acid and/or nucleic acid sequences of a peptide encoded by an open reading frame that is contained in a gene cluster that encodes at least one protein involved in the His-Asp phosphorelay pathway and an ABC transporter.

It is a further object of the present invention to provide methods of detecting and/or identifying penicillin (or related B lactams) or vancomycin tolerant bacterial strains.

It is a further object of the present invention to provide a method of treating a disease or preventing a condition caused by bacteria through administering a pharmaceutical composition containing a peptide of the present invention.

These and other aspects of the present invention will be better appreciated by reference to the following drawings and Detailed Description.

BRIEF DESCRIPTION OF THE DRAWINGS

FIGS. 2A–2B shows the antibacterial activity of the peptide having the amino acid sequence of SEQ ID NO:2 as determined by the change in optical density at 620 nm plotted against time (hours), indicative of the growth curve of R6 bacteria in the presence and absence of 0.1 mM of the peptide having the amino acid sequence of SEQ ID NO:2 (FIG. 2A). A bar graph showing cell viability in the absence and presence of the peptide is shown in FIG. 2B. R6 is a wild type pneumococcus which undergoes autolysis in the presence of penicillin. The peptide kills the bacteria without substantial cell lysis occurring.

FIG. 5 shows the ability of the following peptides to inhibit R6 growth. Variants tested are indicated by the underlined changes in sequence:

Peptide 1: MRKEFHNVLSSGQLLADKRPARDYN (SEQ ID NO.2)

Peptide 2: MRKEFHNVLSSGQLLADKRPARDAN (SEQ ID NO.6)

Peptide 3: MRKEFHNVLSAGQLLADKRPARDYN (SEQ ID NO.4)

Peptide 4: MRKEFHNVLSSGQL (SEQ ID NO.8)

Peptide 5: LADKRPARDYN (SEQ ID NO.10)

Peptides (100 μM final concentration) were added to growing R6 at an OD 620 nm of 0.1.

Figure 6A:
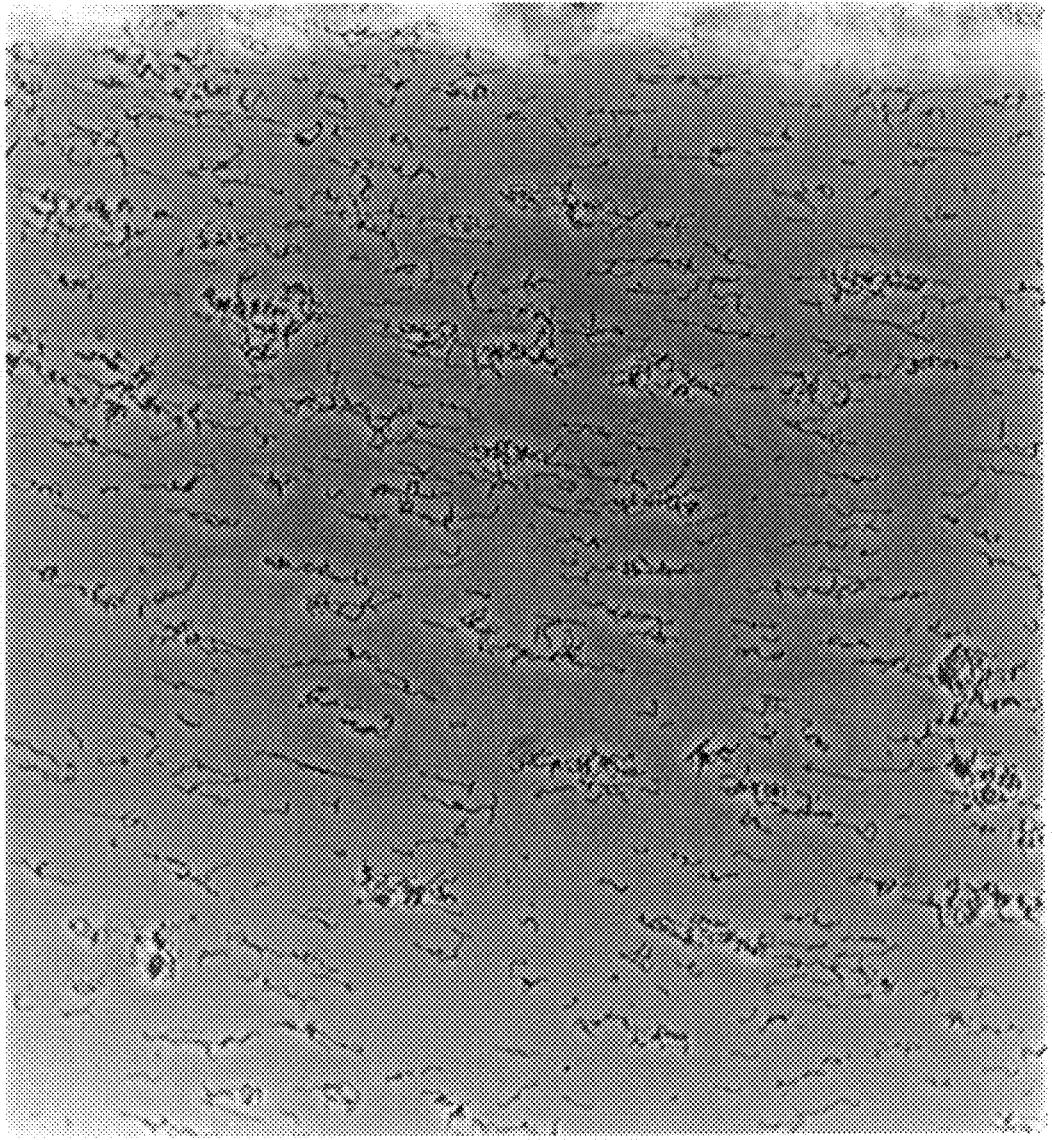
Figure 6B:

FIG. 6A shows Lyt 4-4 in a long chain, at an $OD_{620}$ of >0.8 in the absence of the peptide having the amino acid sequence of SEQ ID NO.2. The same strain at an $OD_{620}$ of 0.8 is shown in FIG. 6B with the addition of that peptide to the medium at 0.5 mM concentration, which results in the dissolution of the chains. Loss of chain formation is a measure of antibacterial activity independent of autolysin.

Figure 7:
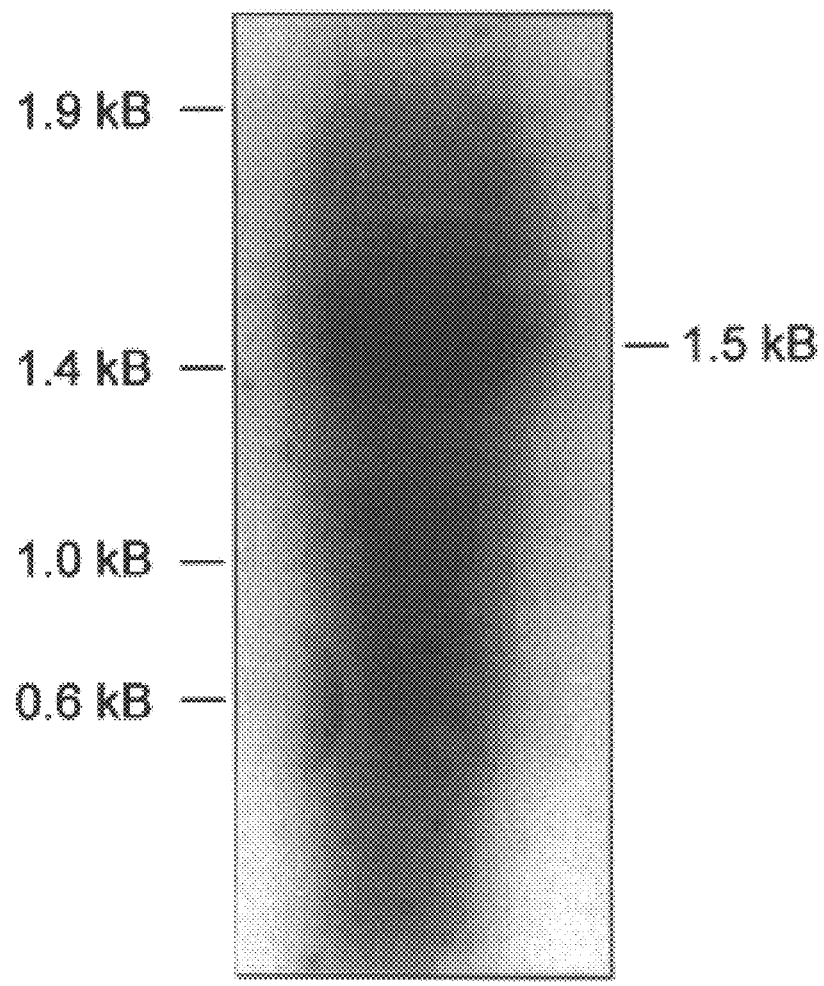

FIG. 7 shows the results of Northern analysis of pneumococcal RNA. A PCR fragment was generated by primers flanking the gene for the peptide having the amino acid sequence of SEQ ID NO:2 but within the intergenic region between the ABC transporter and the RR/HK:5'AATGAGTCTAGAATAAAGATTGC3' (SEQ ID NO:37) (9 residues downstream of the termination codon of ORF W2) and 3'CCCATCCATAAATAAGATTCT5' (SEQ ID NO:38) (beginning at the C at the second residue in the termination codon of the peptide). The PCR fragment was labeled with $\alpha^{32}P[dCTP]$ and used as a probe for the RNA product of the peptide gene. The product indicated by the arrow at ~1.4 kB is consistent with co-transcription of genes for ORF W2 and P.

Figure 8:
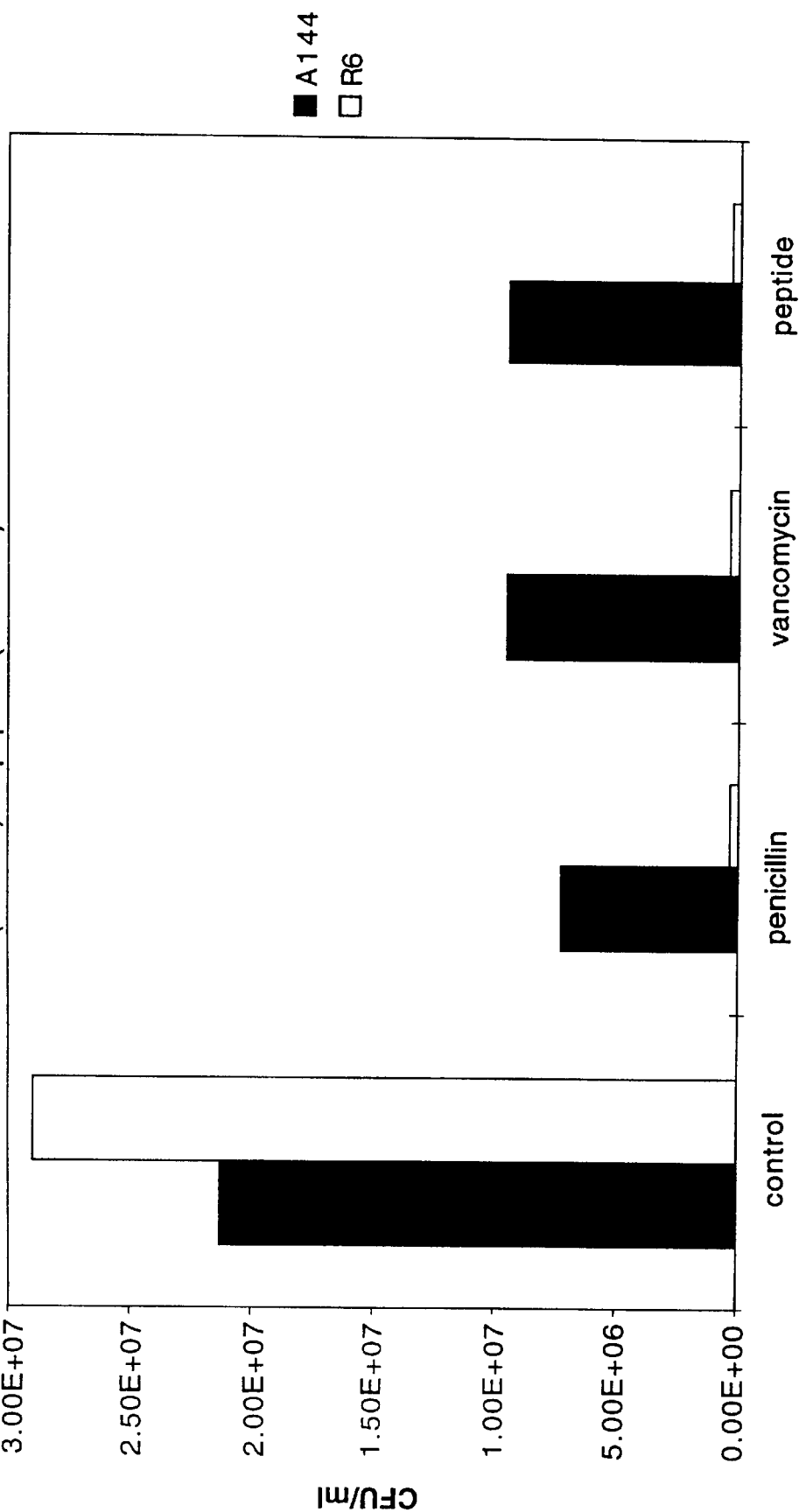

FIG. 8 shows the cell viability (CFU/ml) of bacterial strains A144 and R6 one hour after the addition of 10× MIC of penicillin, or 10× MIC of vancomycin, or 0.4 mM of the peptide having the amino acid sequence of SEQ ID NO:2, or with no additions.

Figure 9:
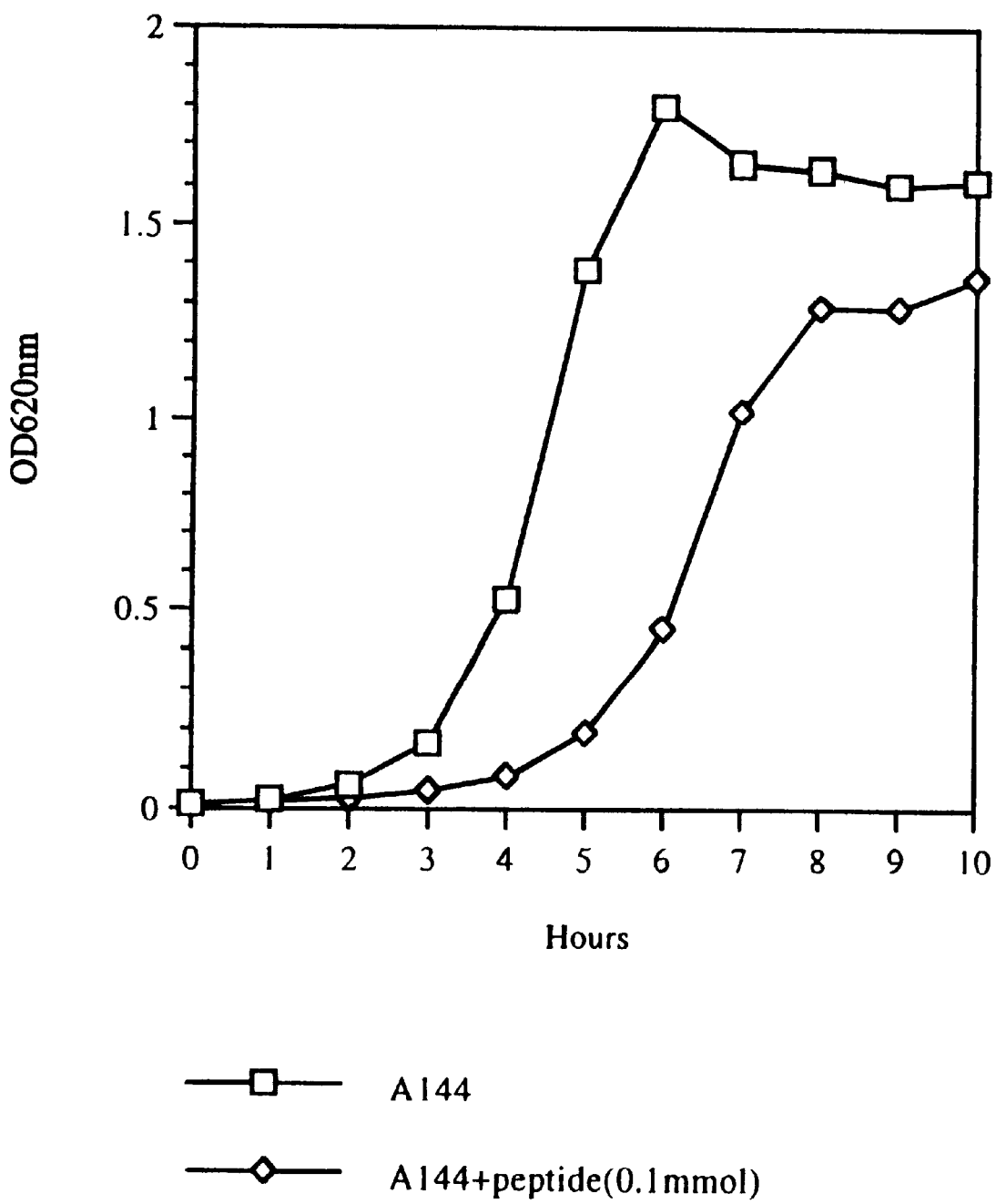

FIG. 9 shows the effect of 0.1 mM of the peptide having the amino acid sequence of SEQ ID NO:2 on the growth of the clinical isolate A144.

Figure 10:
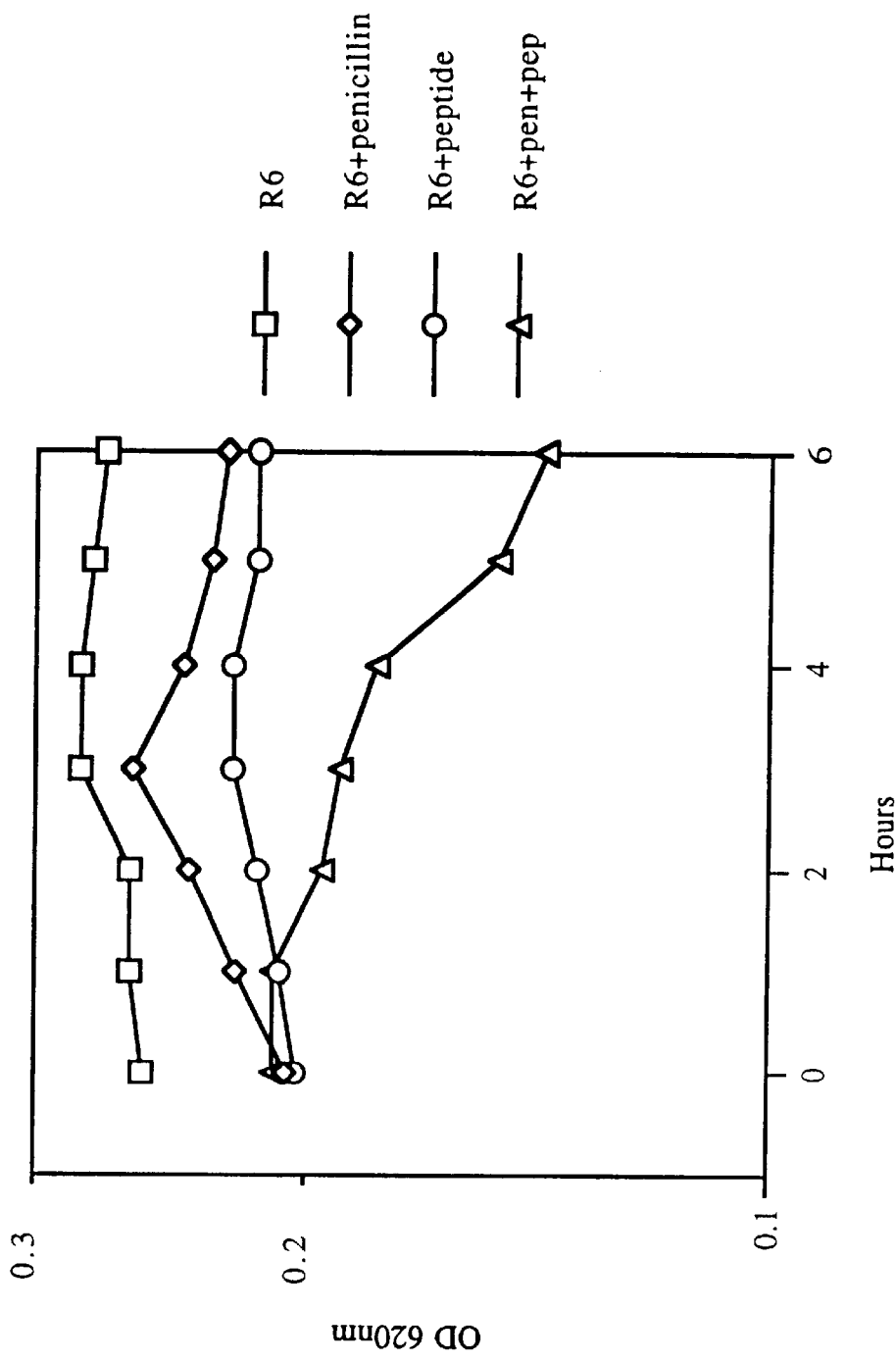

FIG. 10 shows the effect of 10× MIC of penicillin and/or 0.5 mM of the peptide having the amino acid sequence of SEQ ID NO:2 on the lysis of R6 cells under starvation conditions.

Figure 11A:
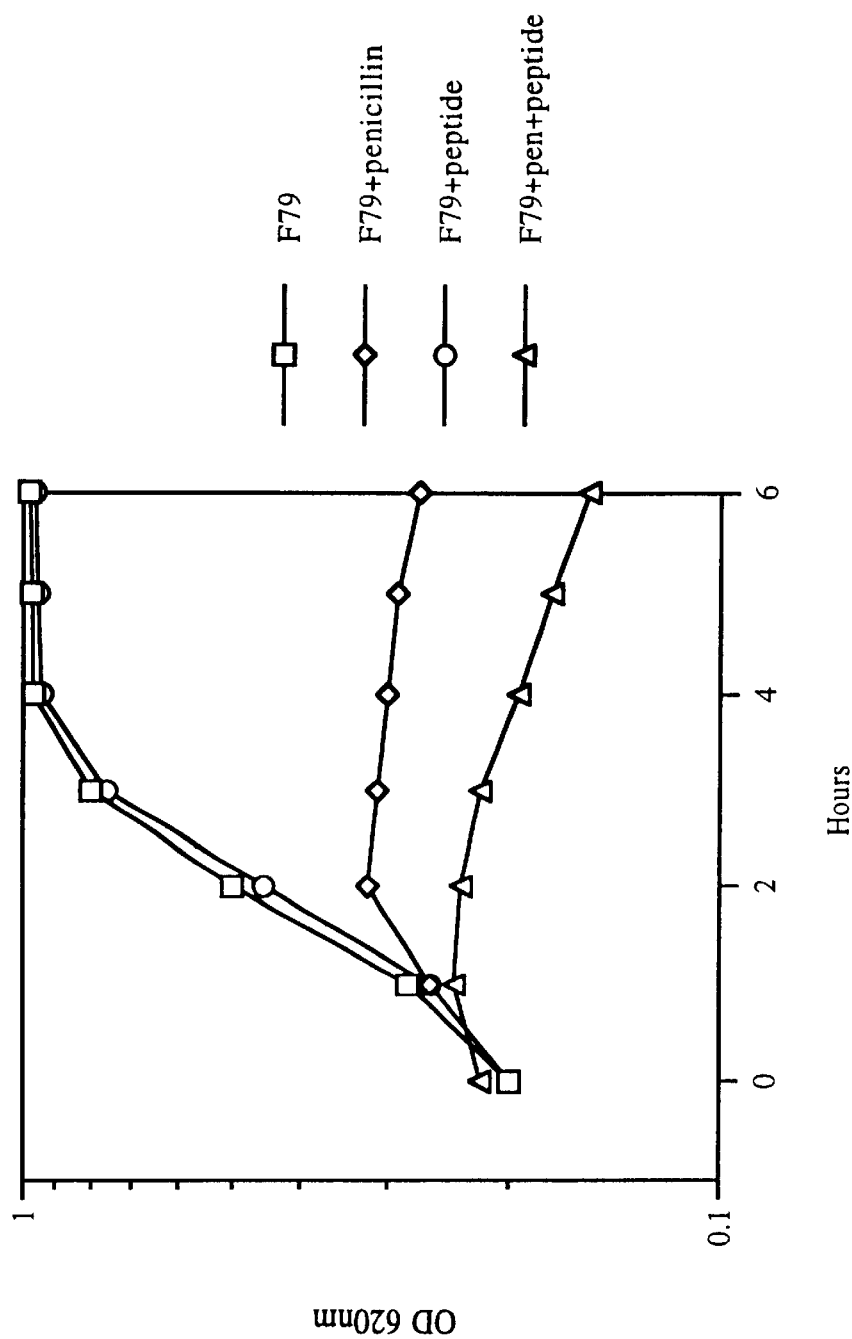
Figure 11B:
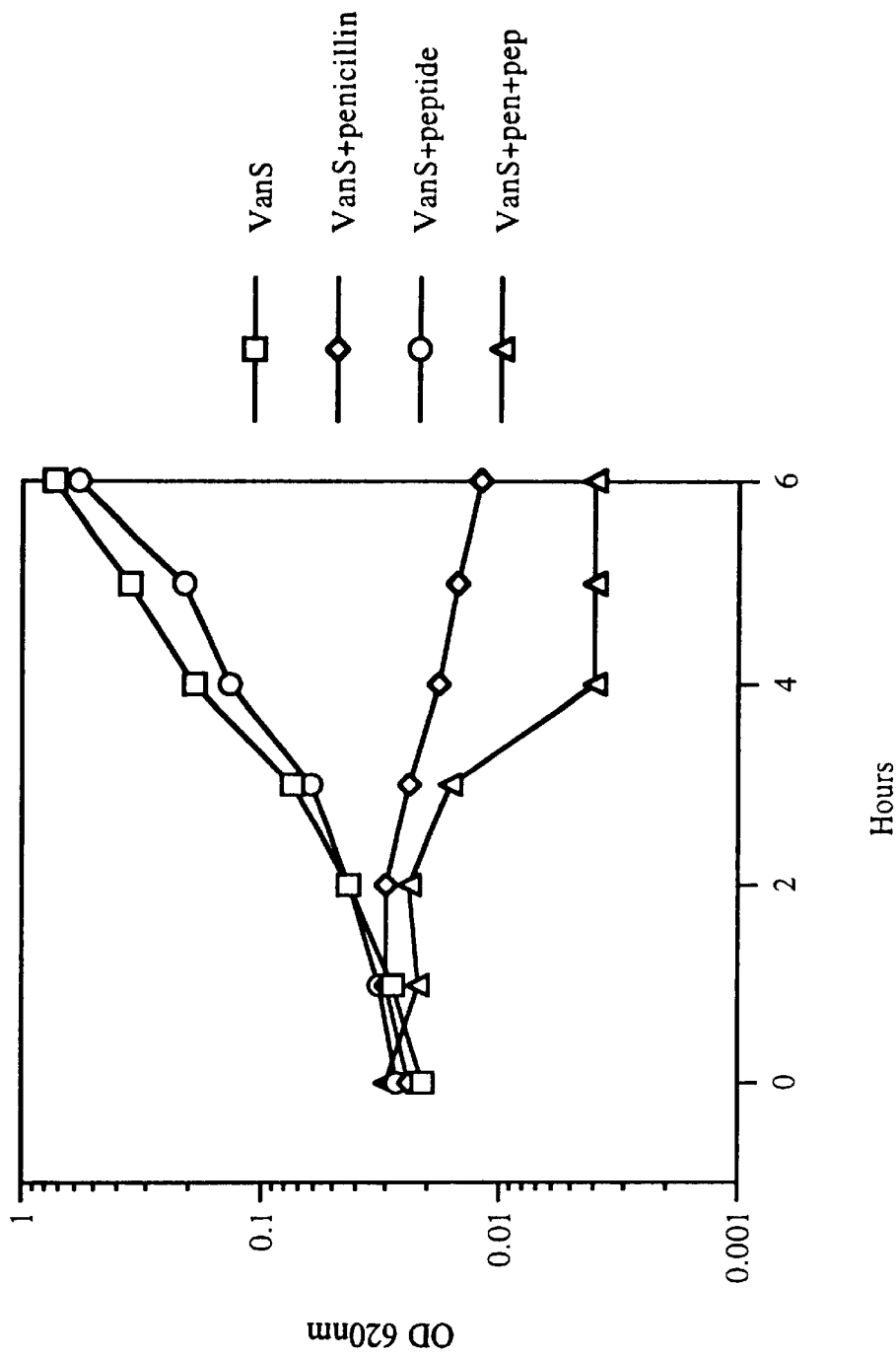

FIGS. 11A–11B show the effects of 10× MIC of penicillin and/or 0.5 mM of the peptide having the amino acid sequence of SEQ ID NO:2 on the lysis of clinical isolate F79 cells (FIG. 11A) and HK mutant VanS cells (FIG. 11B).

Figure 12:
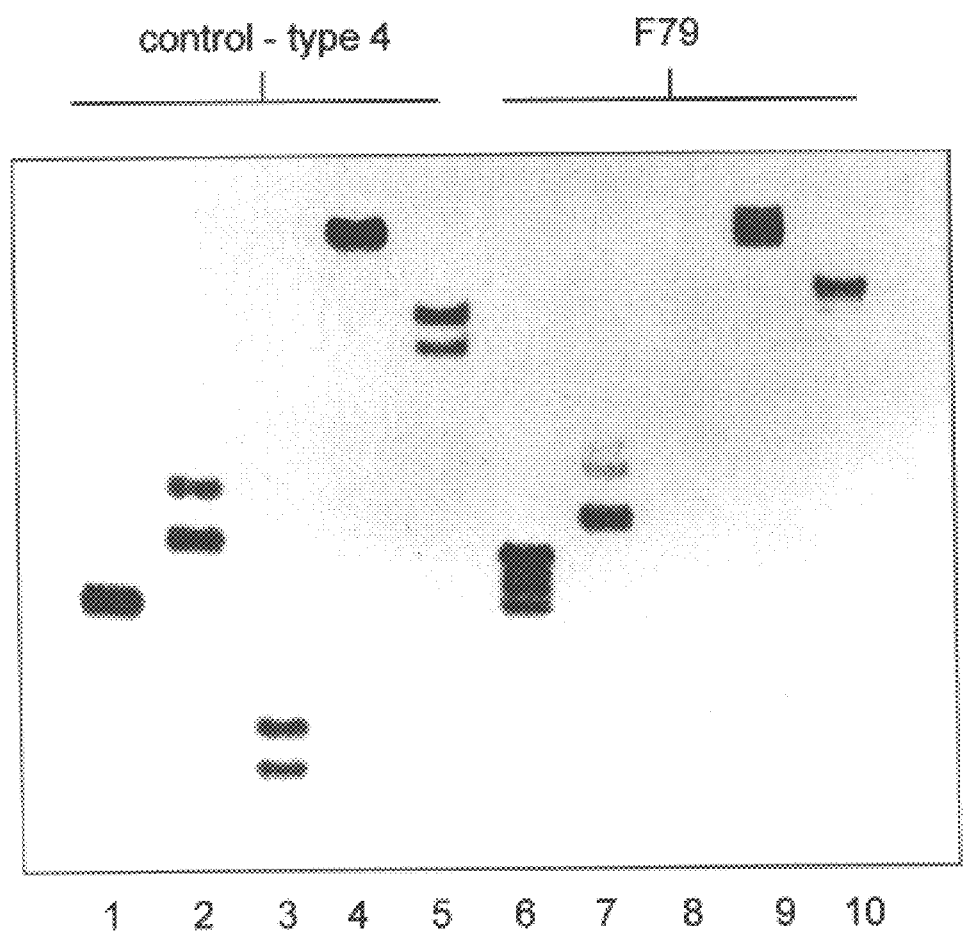

FIG. 12 shows the comparative analysis of two clinical isolates by single-strand conformation polymorphism (SSCP). A wildtype lysis-prone pneumococcus is the control (lanes 1–5) whereas results from the tolerant isolate, F79, is shown in lanes 6–10.

Figure 1:
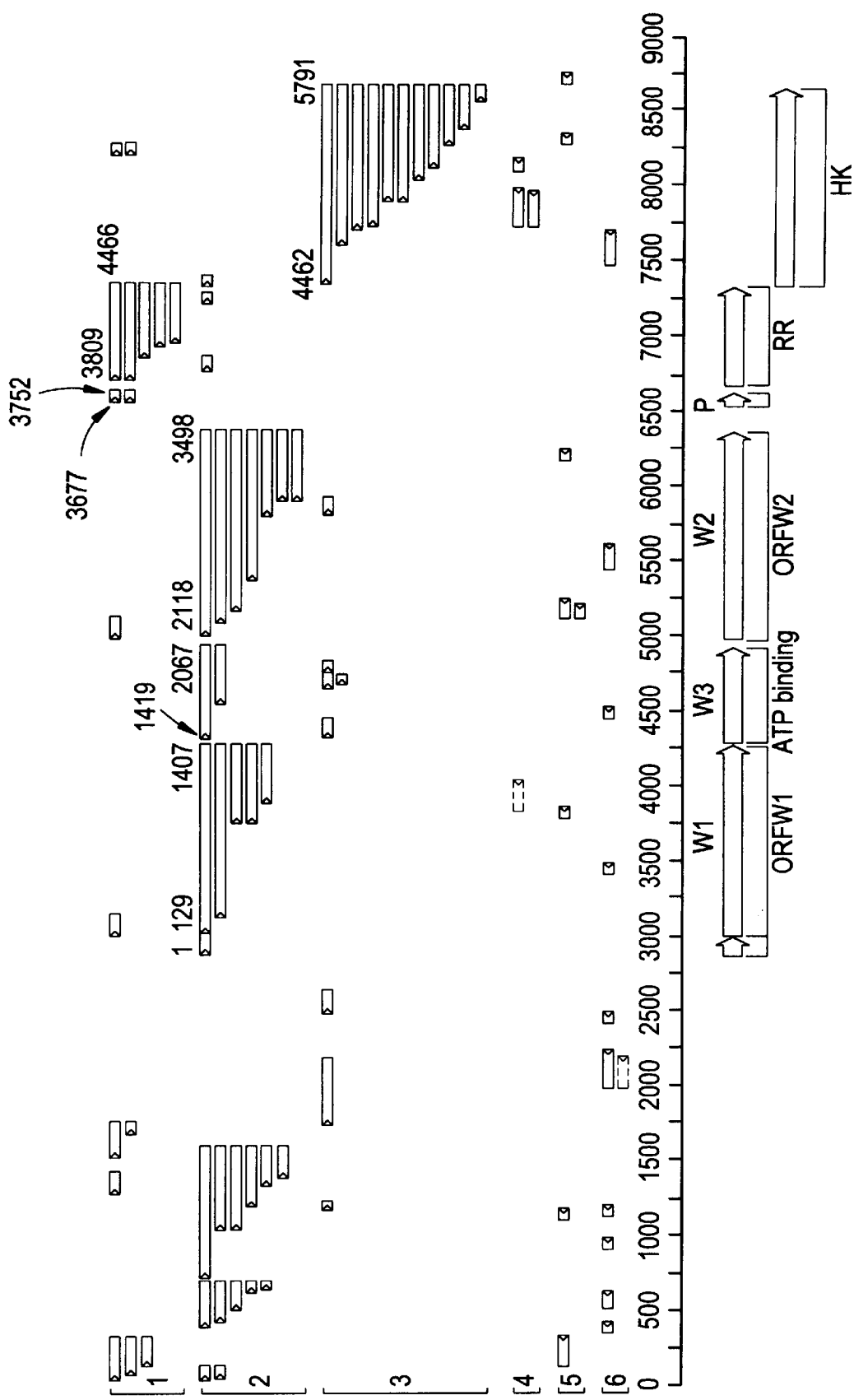
FIG. 1 shows a linear genetic map of a region of the *Streptococcus pneumoniae* genome having six open reading frames: ORFWI (vex 1), ORFW2 (vex3), and ORFW3 (vex2) which form an operon classified by homology as an ABC transporter system; RR and HK which form a two-component sensor-regulator system in which RR (vncR) encodes a response regulator and HK (vncS) encodes a sensor histidine kinase; and an additional peptide (P) at about residue 6500 which has the nucleic acid sequence of SEQ ID NO:1 that encodes the amino acid sequence of SEQ ID NO:2.
Figure 13:
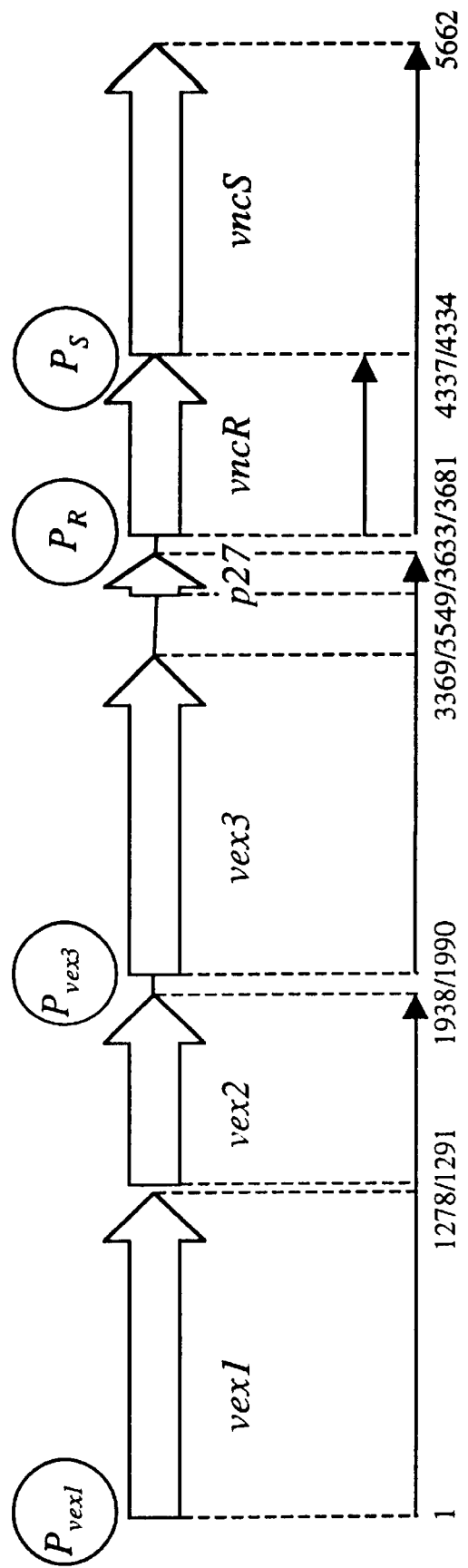

FIG. 13 shows the organization of the gene locus encoding the putative ABC transporter Vex, (which contains the gene products of vex1, vex2, and vex3) the gene encoding peptide P27, (p28, which contains 28 codons including the 27 amino acids of P27 and a stop codon), and the two-component regulatory system VncR (or RR, see FIG. 1) and VncS (or HK see FIG. 1). Putative promoters of the ABC transporter Vex (indicated by Pvex1, and Pvex3) are at positions –26 and 1930.

Figure 14:
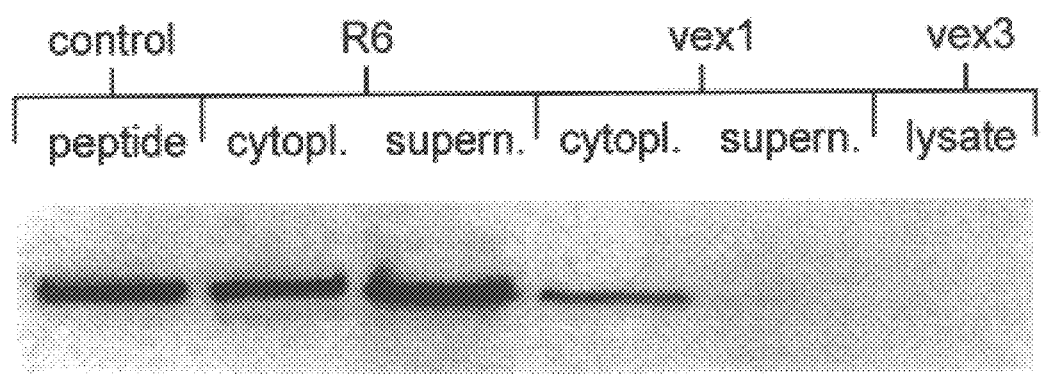

FIG. 14 shows the inmmunoblot analysis of P27 using polyclonal anti-P27 antibodies (1:1000). P27 was detected at 3-kDA in the cytoplasm and the supernatant of R6. P27 was non-detectable in the supernatant of the loss of function mutant vex1. No reactive species was detected in the loss of function mutant vex3.

Figure 15A:
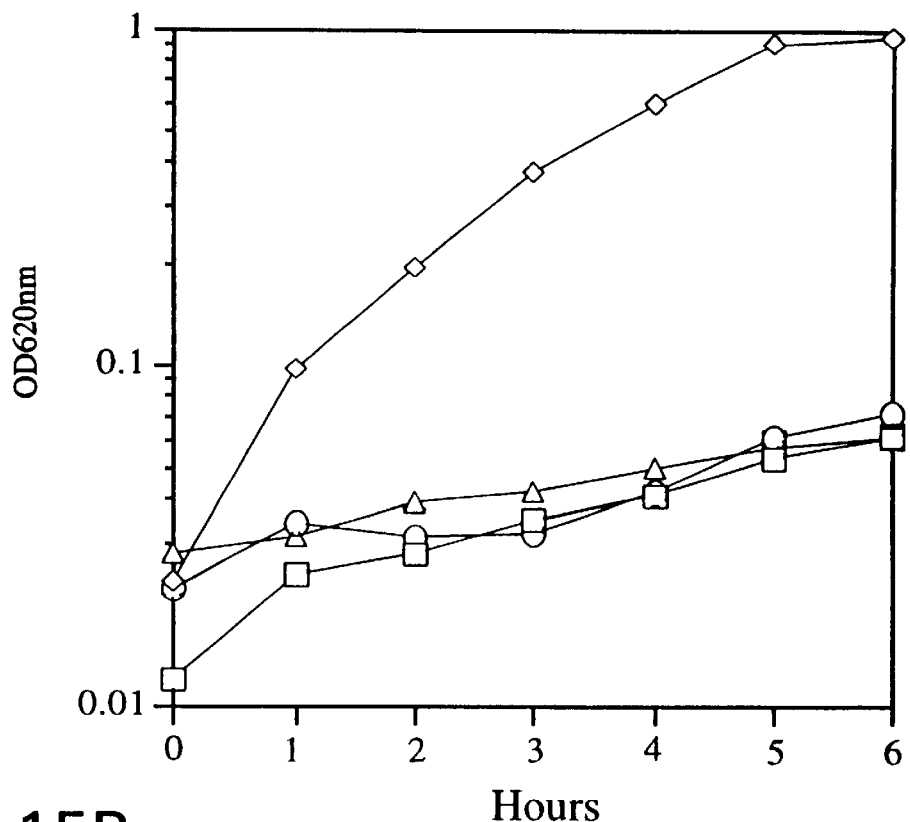
Figure 15B:
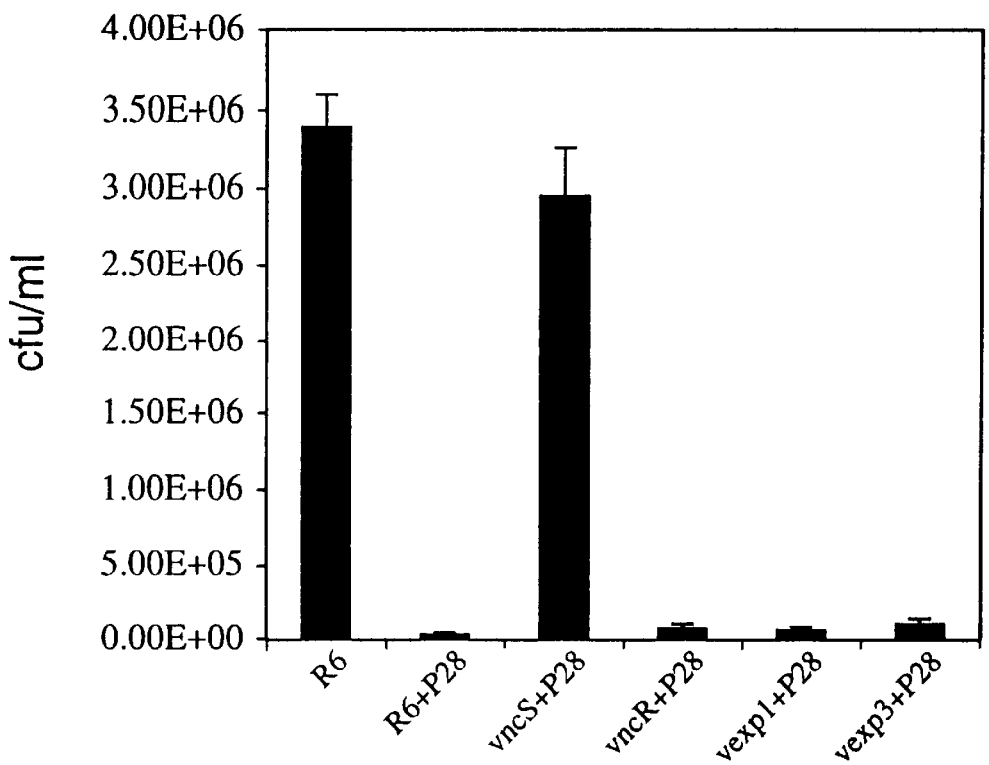
Figure 15C:
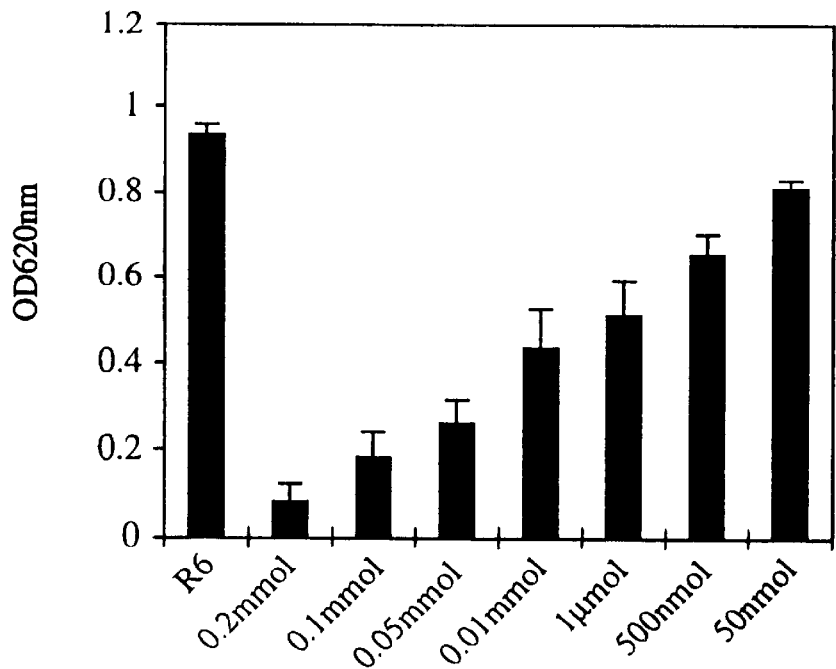

FIGS. 15A–15C show the effect of the synthetic peptide homolog P27 on induced growth inhibition. FIG. 15A shows the decrease in optical density at 620 nm over time (up to 6 hours) when 0. 1mM synthetic peptide, P27. is added the Parental strain, R6 (□), loss of function mutant vncS (◊), mutant vncR (○) or mutant vex1 (Δ). Cultures were in the early exponential phase of growth ($10^6$ cfu/ml) when treated with the synthetic peptide, P27. FIG. 15B is a block diagram showing the viability counts (after one hour) of parent strain R6, and loss of function mutants vncS, vncR, vex1, vex3, following the addition of 0.1 mM P27. R6 without the peptide is the positive control. FIG. 15C is a block diagram showing the dose dependent effect of P27 on the growth of R6. Experimental conditions are the same as in FIG. 15A.

Figure 16:
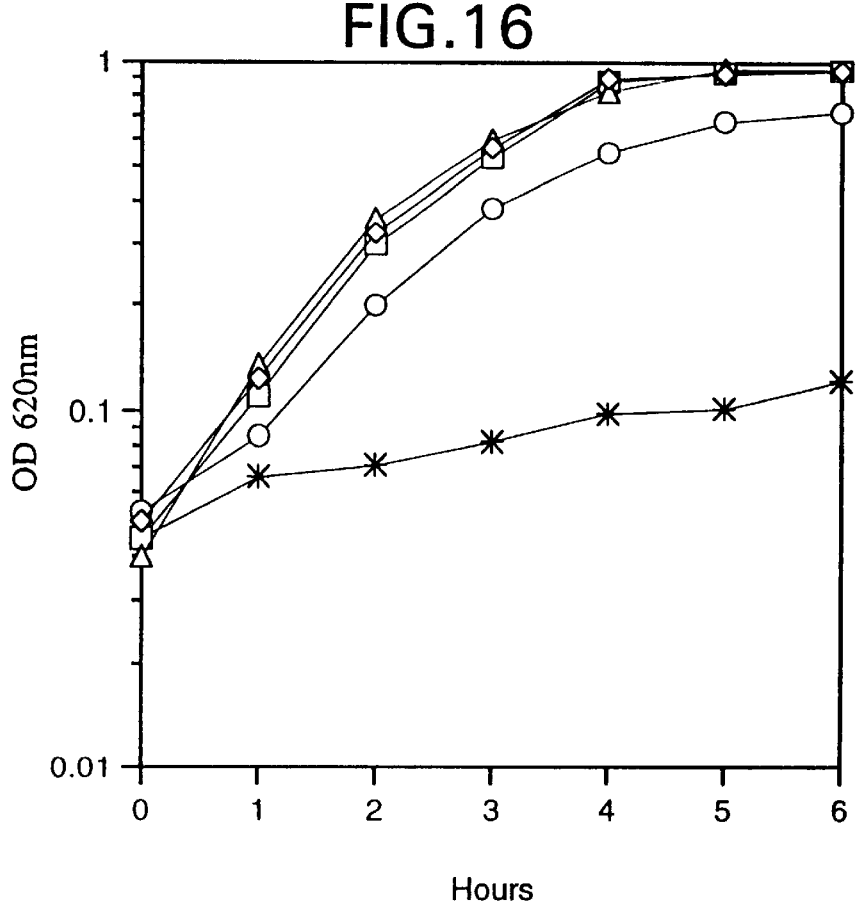

FIG. 16 shows the effect of variants of the P27 peptide on the growth of R6. Cultures in the early exponential phase ($10^6$ cfu/ml) were treated with 0.1 mM P27 (*), 14-mer C-terminal peptide (□), 14-mer N-terminal peptide (Δ), a truncate lacking the 5C-terminal amino acids (○) or an alternative peptide (◊).

Figure 17:
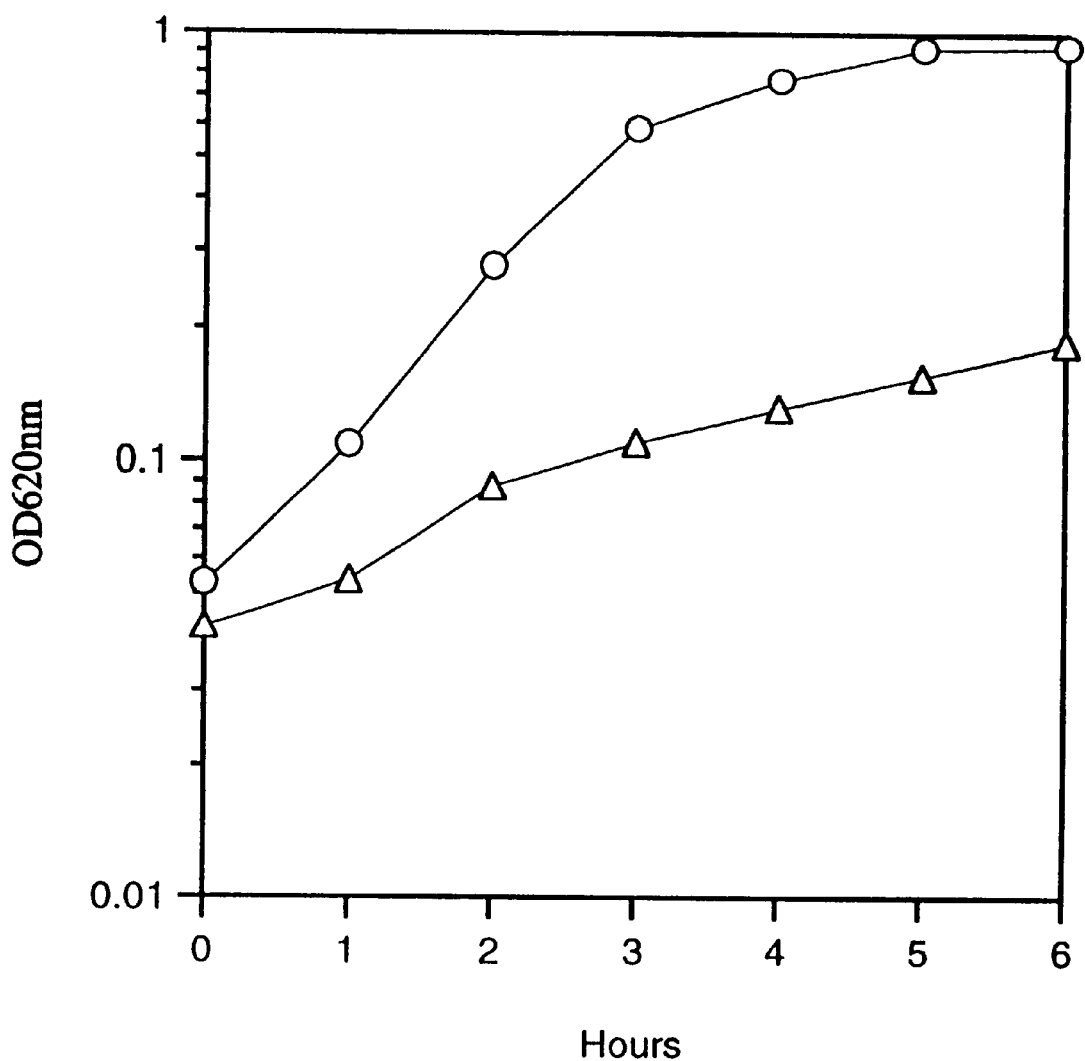

FIG. 17 shows the effect of the synthetic peptide homolog P27 on the growth of the autolysin deficient strain Lyt-4-4 (○). The Parent strain, R6, is the control (Δ).

Figure 18A:
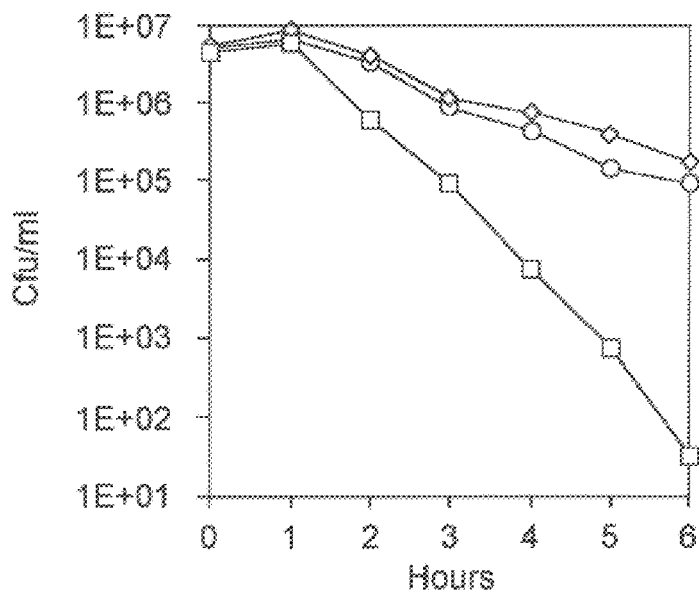
Figure 18B:
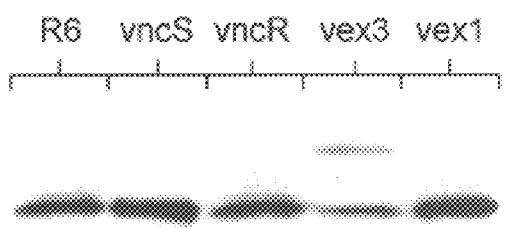
Figure 18C:
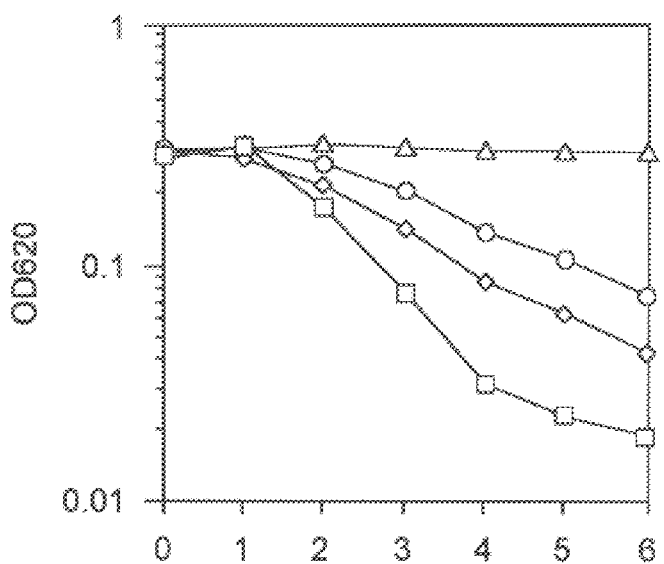

FIGS. 18A–18C show the effect of the loss of function of vex3 and vncS on the bactericidal activity of vancomycin. FIG. 18A shows the results of cultures in the early exponential phase of growth ($10^7$ cfu/ml) that were treated with 10× MIC of vancomycin (5 μg/ml). Bacterial viability was followed for six hours. (Parent strain, R6 (□), vex3 mutant (○), and vncS mutant (◊)). FIG. 18 depicts a Western blot of autolysin preparations of parent strain R6, and the loss of the function mutants vncS, vncR, vex3, and vex1. A polyclonal anti-autolysin antibody (1:1000) was used. FIG. 18C depicts the results of the functional assay of autolysin activity. Autolysin preparations of R6 (□), and the loss of the function mutants vex3 (◊) and vncS (○) were added to cultures of the autolysis defective strain Lyt-4-4 at an optical density at 620 nm of 0.3. Lyt-4-4 serves as the negative control (Δ). Lysis was followed after the addition of 10× MIC of penicillin (0.1 μg/ml) at an $OD_{620\ nm}$ of 0.25.

Figure 19:
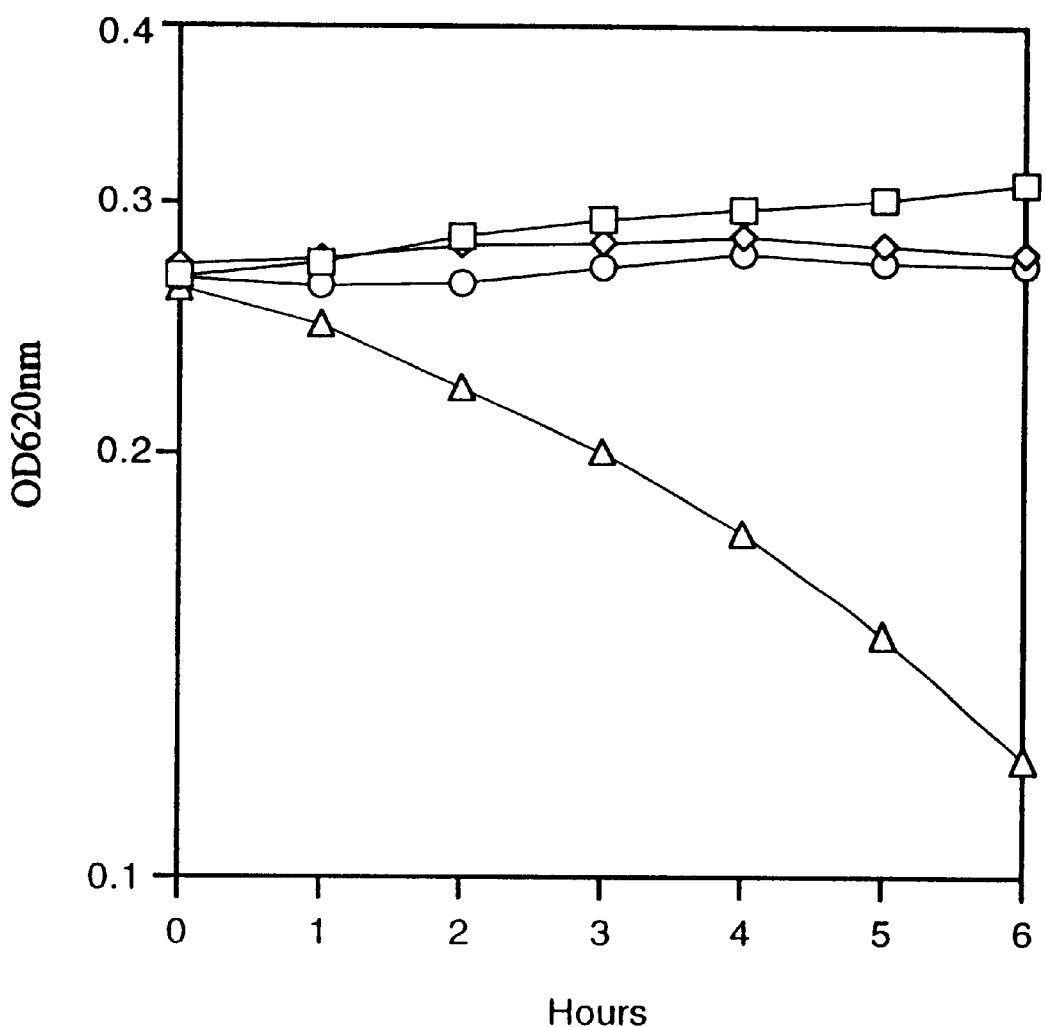

FIG. 19 shows the inhibition of protein synthesis of R6 (◊) by leucine deprivation which stops cell growth. The effect of the addition of 10× MIC of (0.1 μg/ml) penicillin (○), 0.1 mM peptide P27 (□) and a combination of penicillin and P27 (Δ) to the leucine deprived R6 cells was monitored at 620 nm over six hours.

DETAILED DESCRIPTION OF THE INVENTION

The present invention provides a method of identifying novel naturally occurring antibiotic peptides found encoded in prokaryotic DNA, preferably bacterial genomic DNA, in regions encoding proteins involved in His-Asp phosphorelay pathways and ABC transporters. The present invention further discloses facile methods of testing such antibiotic peptides for potency and effectiveness. In addition, the present invention provides a new class of antibiotic, i.e., peptides that act independently of known autolysins. Furthermore, the present invention provides antibiotics that act synergistically with penicillin (or analogues thereof) to kill bacterial cells. Such peptides and combinations of peptides and other antibiotics can be used to treat bacterial infections and inflammations. Additionally, the present invention provides antibiotics that can kill but not lyse autolysis prone pneumococci.

The present invention further provides methods of making, purifying, characterizing, and testing the novel antibiotic peptides of the present invention. Included in the present invention are analogs of the peptides that contain alternative naturally occurring amino acids, and/or unnatural amino acids. Such analogs can be readily tested by known methodology, including by methods disclosed herein. Modifications envisioned by the present invention include proteolytic cleavage of the peptides, or through the use of genetic engineering including site-directed mutagenesis. The peptides are preferably prepared by chemical synthesis, e.g., by solid phase peptide synthesis. Alternatively, the peptides can be made using recombinant DNA technology.

The present invention also provides pharmaceutical compositions containing the peptides either alone or in conjunction with other antibiotics (such as penicillin) as well as therapeutic methods of using the peptide antibiotics of the present invention, including in the treatment and prevention of bacterial infections and inflammations. The peptides of the present invention can also be employed as a preservative or as part of a composition used as a preservative.

In addition, the peptides of the present invention can be used as a laboratory tool, such as in conjunction with one or more bacterial drug selection markers, since specific bacterial strains (or species) are either resistant or susceptible to the peptide. For example, the peptide having the amino acid sequence of SEQ ID NO:2 or SEQ ID NO:44 can kill LytA deficient cells, and can kill some but not all clinical vancomycin tolerant strains. This particular peptide also can be used in conjunction with penicillin in related screening techniques, since penicillin only arrests cell growth in the absence of LytA, whereas the peptide kills the cells. Analogously, this particular peptide can be used in conjunction with penicillin to kill penicillin tolerant cells.

The present invention further provides methods for testing potential agents or drugs, preferably putative antibiotics (either peptides or non-peptides) to identify agents or drugs which are useful in preventing bacterial proliferation or kill bacterial cells.

In addition the present invention provides bacterial cells that contain a defective His-Asp phosphorelay pathway and/or a defective ABC transporter system that contains a "non-functional" component. Such strains can be used for screening for potential antibiotics using commercial chemical drug libraries, combinatorial chemistry and/or phage libraries. Furthermore, these strains can be used to determine the relative efficacy of both novel and known antibiotics. For example, such strains can be used to help identify antibiotics which are effective against vancomycin and/or penicillin tolerant bacteria. Useful candidate antibiotics are identified which have the ability to inhibit the growth, and/or kill, and/or lyse one or more of these strains. In addition, or alternatively, useful candidate antibiotics can be identified that kill bacteria synergistically with penicillin (or analogues thereof) or kill autolysis prone pneumococci without lysing the cell.

The present invention further provides methods of geographically tracking the spread of tolerant and/or resistant bacterial strains. One such method is performed by Single Stranded Conformational Polymorphism (SSCP) analysis in which changes in the sequences of a component in the ABC transporter system and/or the His-Asp phosphorelay pathway (e.g. the sensor histidine kinase or the response regulator) are monitored. When similar changes are detected in a set of clinical isolates, it can be presumed that the clinical isolates are derived from a common source. Therefore, the present invention also provides important epidemiological tools.

In addition, the present invent uses *Streptococcus pneumoniae* as a model, and demonstrates that the two component system VncR/S regulates the activity of different autolytic pathways, including the major autolysin LytA. VncR/S is also shown to control transcription of the signal peptide P27, which is able to induce cell death independently of the major pneumococcal autolysin LytA. Therefore, the present invention identifies a novel mechanism for the general induction of murein hydrolases via a newly identified signal peptide of the present invention.

Therefore, if appearing herein, the following terms shall have the definitions set out below.

As used herein the term "peptide" is used in its broadest sense to refer to a compound of two or more subunit amino acids, amino acid analogs, or peptidomimetics. No upper limit for the number of amino acids in a peptide of the present invention is either expressed or implied. The subunits may be linked by peptide bonds. In another embodiment, the subunit may be linked by other bonds, e.g., ester, ether, etc. Peptides can be in any structural configuration including linear, branched or cyclic configurations. As used herein the term "amino acids" refers to either natural and/or unnatural or synthetic amino acids, including glycine and both the D or L optical isomers, and amino acid analogs and peptidomimetics.

As used herein the term "autolysin" is used to define a bacterial enzyme which breaks a bond in a bacterial wall. This bond breaking can lead to the dissolution of the integrity of the exoskeleton and lead to the osmotic lysis of the bacterial cell.

As used herein the term "histidyl-aspartyl phosphorelay pathway" is used interchangeably with the terms "histidyl-aspartyl phosphorelay signal transduction system" and "histidyl-aspartyl phosphorelay system" and the terms "His-Asp phosphorelay signal transduction system", "His-Asp phosphorelay pathway", and "His-Asp phosphorelay system" and "His-Asp signaling system" and any variants not specifically listed, may be used interchangeably, and as used throughout the present Application refer to a signal transduction system that is prevalent in prokaryotic cells. Two key components in the His-Asp phosphorelay signal transduction system are: (1) a sensor histidine kinase "HK", which is generally a transmembrane protein; and (2) a response regulator, "RR" which mediates changes in gene expression and/or cellular locomotion. As disclosed herein one such HK/RR two component system of the present invention is VncS-VncR.

As used herein a cell having a "defective His-Asp phosphorelay pathway" is a mutated cell which in its wild type form contains a functional His-Asp phosphorelay pathway, but in its mutated form is lacking at least one functional component of this His-Asp phosphorelay pathway, e.g. it contains a non-functional component or is missing the component entirely. Preferably, the cell is a bacterial cell. In a preferred embodiment, the His-Asp phosphorelay pathway of the wild type cell has a sensor histidine kinase having an amino acid sequence of SEQ ID NO:14 and a response regulator having an amino acid sequence of SEQ ID NO:16.

As used herein a "non-functional" sensor histidine kinase fails to activate its cognate response regulator.

As used herein a "non-functional" response regulator fails to activate or repress gene transcription in response to ligand binding by its cognate sensor histidine kinase.

As used herein a cell having a "defective ABC transporter system" is a mutated cell which in its wild type form contains a functional ABC transport system, but in its mutated form is lacking at least one functional component of the ABC transport system e.g., it contains a non-functional component or is missing the component entirely. In Example 12, the ABC transport system contains three components encoded by vex1, vex2, and vex3. Additions, deletions, substitutions and the like to the nucleotide sequence of a component of the ABC transporter system can make the component non-functional.

As used herein the term "gene cluster" refers to two or more genes encoding proteins that are involved in a specific pathway and are positioned in a fungal or prokaryotic DNA (e.g., a bacterial genome) in close proximity to each other (e. g., next to each other). An example of a gene cluster is provided in FIG. 1, where a gene cluster encoding an ABC transporter system is next to a gene cluster encoding a sensor histidine kinase, and a response regulator.

As used herein a cell that is "autolysin deficient" either lacks the autolysin LytA or contains a functionally inactive autolysin.

Peptides and Proteins

A peptide of the present invention can be identified in prokaryotic DNA, preferably a bacterial genome, in regions encoding proteins involved in an His-Asp phosphorelay pathway or a related pathway and an ABC transporter system. Once such a peptide is identified (e.g., the peptide having the amino acid sequence of SEQ ID NO:2 or SEQ ID NO:44 as described in the Examples below) the peptide can be obtained and tested in standard bacterial drug assays, as disclosed herein. Alternative peptides (e.g. the peptide having the amino acid sequence of SEQ ID NO:4 described in the Examples below) can be made by altering the amino acid sequence of the naturally occurring peptide by making substitutions, additions or deletions that provide for functionally equivalent or functionally superior molecules. Preferably, such derivatives are made that have an enhanced or increased effect on killing bacteria and/or inhibiting bacterial growth. For example, a preferred peptide of the present invention may show equivalent cell killing at an order of magnitude lower concentration than the naturally occurring peptide.

Likewise, peptide or protein derivatives and analogs of the invention include, but are not limited to, those containing, as a primary amino acid sequence, all or part of the amino acid sequence of the peptide or protein including altered sequences in which functionally equivalent amino acid residues are substituted for residues within the sequence resulting in a conservative amino acid substitution. Such substitutions are defined as a conservative substitution.

For example, one or more amino acid residues within the sequence can be substituted by another amino acid of a similar polarity, which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. Amino acids containing aromatic ring structures are phenylalanine, tryptophan, and tyrosine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such alterations will not be expected to significantly affect apparent molecular weight as determined by polyacrylamide gel electrophoresis, or isoelectric point.

Particularly preferred conservative substitutions are:

Lys for Arg and vice versa such that a positive charge may be maintained;

Glu for Asp and vice versa such that a negative charge may be maintained;

Ser for Thr such that a free —OH can be maintained; and

Gln for Asn such that a free $NH_2$ can be maintained.

Non-conservative amino acid substitutions may also be introduced to substitute an amino acid with a particularly preferable property. For example, a Cys may be introduced at a potential site for disulfide bridges with another Cys. Pro may be introduced because of its particularly planar structure, which induces β-turns in the structure of the peptide.

In addition all of the peptides or proteins of the present invention can be placed in a fusion or chimeric peptide or protein, or e.g., labeled to have an N-terminal FLAG-tag. In a particular embodiment a peptide can be modified to contain a marker protein such as green fluorescent protein as described in U.S. Pat. No. 5,625,048 filed Apr. 29, 1997 and WO 97/26333, published Jul. 24, 1997 each of which are hereby incorporated by reference herein in their entireties.

The peptides of the present invention can be chemically synthesized. Synthetic peptides can be prepared using the well known techniques of solid phase, liquid phase, or peptide condensation techniques, or any combination thereof, and can include natural and/or unnatural amino acids. Amino acids used for peptide synthesis may be standard Boc ($N^\alpha$-amino protected $N^\alpha$-t-butyloxycarbonyl) amino acid resin with the standard deprotecting, neutralization, coupling and wash protocols of the original solid phase procedure of Merrifield [*J. Am. Chem. Soc.*, 85:2149–2154 (1963)], or the base-labile $N^\alpha$-amino protected 9-fluorenylmethoxycarbonyl (Fmoc) amino acids first described by Carpino and Han [*J. Org. Chem.*, 37:3403–3409 (1972)]. Both Fmoc and Boc $N^\alpha$-amino protected amino acids can be obtained from Fluka, Bachem, Advanced Chemtech, Sigma, Cambridge Research Biochemical, Bachem, or Peninsula Labs or other chemical companies familiar to those who practice this art. In addition, the method of the invention can be used with other $N^\alpha$-protecting groups that are familiar to those skilled in this art. Solid phase peptide synthesis may be accomplished by techniques familiar to those in the art and provided, for example, in Stewart and Young, [*Solid Phase Synthesis*, Second Edition, Pierce Chemical Co., Rockford, Ill. (1984)] or Fields and Noble, [*Int. J. Pept. Protein Res.*, 35:161–214 (1990)]1, or using automated synthesizers, such as sold by ABS. Thus, peptides of the invention may comprise D-amino acids, a combination of D- and L-amino acids, and various "designer" amino acids (e.g., β-methyl amino acids; $C^\alpha$-methyl amino acids; and $N^\alpha$-methyl amino acids; etc.) to convey special properties. Synthetic amino acids include ornithine for lysine, fluorophenylalanine for phenylalanine, and norleucine for leucine or isoleucine. Additionally, by assigning specific amino acids at specific coupling steps, α-helices, β turns, β sheets, α-turns, and cyclic peptides can be generated.

In one aspect of the invention, the peptides may comprise a special amino acid at the C-terminus which incorporates either a $CO_2H$ or $CONH_2$ side chain to simulate a free glycine or a glycine-amide group. Another way to consider this special residue would be as a D or L amino acid analog with a side chain consisting of the linker or bond to the bead. In one embodiment, the pseudo-free C-terminal residue may be of the D or the L optical configuration; in another embodiment, a racemic mixture of D and L-isomers may be used.

In an additional embodiment, pyroglutamate may be included as the N-terminal residue of the peptide. Although pyroglutamate is not amenable to sequence by Edman degradation, by limiting substitution to only 50% of the peptides on a given bead with N-terminal pyroglutamate, there will remain enough non-pyroglutamate peptide on the bead for sequencing. One of ordinary skill would readily recognize that this technique could be used for sequencing of any peptide that incorporates a residue resistant to Edman degradation at the N-terminus. Other methods to characterize individual peptides that demonstrate desired activity are described in detail infra. Specific activity of a peptide that comprises a blocked N-terminal group, e.g., pyroglutamate, when the particular N-terminal group is present in 50% of the peptides, would readily be demonstrated by comparing activity of a completely (100%) blocked peptide with a non-blocked (0%) peptide.

In a further embodiment, subunits of peptides that confer useful chemical and structural properties will be chosen. For example, peptides comprising D-amino acids will be resistant to L-amino acid-specific proteases in vivo. In addition, the present invention envisions preparing peptides that have more well defined structural properties, and the use of peptidomimetics, and peptidomimetic bonds, such as ester bonds, to prepare peptides with novel properties. In another embodiment, a peptide may be generated that incorporates a reduced peptide bond, i.e., $R_1$—$CH_2$—$NH$—$R_2$, where R1 and $R_2$ are amino acid residues or sequences. A reduced peptide bond may be introduced as a dipeptide subunit. Such a molecule would be resistant to peptide bond hydrolysis, e.g., protease activity. Such peptides would provide ligands with unique function and activity, such as extended half-lives in vivo due to resistance to metabolic breakdown, or protease activity. Furthermore, it is well known that in certain systems constrained peptides show enhanced functional activity [Hruby, Life Sciences, 31:189–199 (1982); Hruby et al., Biochem J., 268:249–262 (1990)]; the present invention provides a method to produce a constrained peptide that incorporates random sequences at all other positions.

Constrained and cyclic peptides: A constrained, cyclic or rigidized peptide may be prepared synthetically, provided that in at least two positions in the sequence of the peptide an amino acid or amino acid analog is inserted that provides a chemical functional group capable of crosslinking to constrain, cyclise or rigidize the peptide after treatment to form the crosslink. Cyclization will be favored when a turn-inducing amino acid is incorporated. Examples of amino acids capable of crosslinking a peptide are cysteine to form disulfides, aspartic acid to form a lactone or a lactam, and a chelator such as α-carboxyl-glutamic acid (Gla) (Bachem) to chelate a transition metal and form a cross-link. Protected α-carboxyl glutamic acid may be prepared by modifying the synthesis described by Zee-Cheng and Olson [Biophys. Biochem. Res. Commun., 94:1128–1132 (1980)]. A peptide in which the peptide sequence comprises at least two amino acids capable of crosslinking may be treated, e.g., by oxidation of cysteine residues to form a disulfide or addition of a metal ion to form a chelate, so as to crosslink the peptide and form a constrained, cyclic or rigidized peptide.

The present invention provides strategies to systematically prepare cross-links. For example, if four cysteine residues are incorporated in the peptide sequence, different protecting groups may be used [Hiskey, in The Peptides: Analysis, Synthesis, Biology, Vol. 3, Gross and Meienhofer, eds., Academic Press: New York, pp. 137–167 (1981); Ponsanti et al., Tetrahedron, 46:8255–8266 (1990)]. The first pair of cysteines may be deprotected and oxidized, then the second set may be deprotected and oxidized. In this way a defined set of disulfide cross-links may be formed. Alternatively, a pair of cysteines and a pair of chelating amino acid analogs may be incorporated so that the cross-links are of a different chemical nature.

Non-classical amino acids that induce Conformational constraints: The following non-classical amino acids may be incorporated in the peptide in order to introduce particular conforniational motifs: 1,2,3,4-tetrahydroisoquinoline-3-carboxylate [Kazmierski et al., J. Am. Chem. Soc., 113:2275–2283 (1991)]; (2S,3S)-methyl-phenylalanine, (2S,3R)-methyl-phenylalanine, (2R,3S)-methyl-phenylalanine and (2R,3R)-methyl-phenylalanine (Kazmierski and Hruby, Tetrahedron Lett., (1991)]; 2-aninotetrahydronaphthalene-2-carboxylic acid [Landis, Ph.D. Thesis, University of Arizona (1989)]; hydroxy-1,2,3,4-tetrahydroisoquinoline-3-carboxylate [Miyake et al., J. Takeda Res. Labs., 43:53–76 (1989)]; β-carboline (D and L) [Kazmierski, Ph.D. Thesis, University of Arizona (1988)]; HIC (Histidine isoquinoline carboxylic acid) [Zechel et al., Int. J. Pep. Protein Res., 43 (1991)]; and HIC (histidine cyclic urea) (Dharanipragada).

The following amino acid analogs and peptidomimetics may be incorporated into a peptide to induce or favor specific secondary structures: LL-Acp (LL-3-amino-2-propenidone-6-carboxylic acid), a β-turn inducing dipeptide analog [Kemp et al., J. Org. Chem., 50:5834–5838 (1985)]; β-sheet inducing analogs [Kemp et al., Tetrahedron Lett., 29:5081–5082 (1988)]; β-turn inducing analogs [Kemp et al., Tetrahedron Lett., 29:5057–5060 (1988)]; α-helix inducing analogs [Kemp et al., Tetrahedron Lett., 29:4935–4938 (1988)]; α-turn inducing analogs [Kemp et al., J. Org. Chem., 54:109:115 (1989)]; and analogs provided by the following references: Nagai and Sato, Tetrahedron Lett., 26:647–650 (1985); DiMaio et al., J. Chem. Soc. Perkin Trans., p. 1687 (1989); also a Gly-Ala turn analog [Kahn et al., Tetrahedron Lett., 30:2317 (1989)]; amide bond isostere [Jones et al., Tetrahedron Lett., 29:3853–3856 (1988)]; tretrazol [Zabrocki et al., J. Am. Chem. Soc., 110:5875–5880 (1988)]; DTC [Samanen et al., Int. J. Protein Pep. Res., 35:501:509 (1990)]; and analogs taught in Olson et al., J. Am. Chem. Sci., 112:323–333 (1990) and Garvey et al., J. Org. Chem., 56:436 (1990). Conformationally restricted mimetics of beta turns and beta bulges, and peptides containing them, are described in U.S. Pat. No. 5,440,013, issued Aug. 8, 1995 to Kahn.

Derivatized and modified peptides: The present invention further provides for modification or derivatization of a peptide of the invention. Modifications of peptides are well known to one of ordinary skill, and include phosphorylation, carboxymethylation, and acylation. Modifications may be effected by chemical or enzymatic means.

In another aspect, glycosylated or fatty acylated peptide derivatives may be prepared. Preparation of glycosylated or fatty acylated peptides is well known in the art as exemplified by the following references:
1. Garg and Jeanloz, 1985, in Advances in Carbohydrate Chemistry and Biochemistry, Vol. 43, Academic Press.
2. Kunz, 1987, in Ang. Chem Int. Ed. English 26:294–308.
3. Horvat et al., 1988, Int. J. Pept. Protein Res. 31:499–507.
4. Bardaji et al., 1990, Ang. Chem. Int. Ed. English, 23:231.

5. Toth et al., 1990, in Peptides: Chemistry, Structure and Biology, Rivier and Marshal, eds., ESCOM Publ., Leiden, pp. 1078–1079.
6. Torres et al., 1989, Experiential 45:574–576.
7. Torres et al., 1989, EMBO J. 8:2925–2932.
8. Hordever and Musiol, 1990, in Peptides: Chemistry, Structure and Biology, loc. cit., 811–812.
9. Zee-Cheng and Olson, 1989, Biochem. Biophys. Res. Commun. 94:1128–1132.
10. Marki et al., 1977, Helv. Chem Acta., 60:807.
11. Fuju et al. 1987, J. Chem. Soc. Chem. Commun., pp. 163–164.
12. Ponsati et al., 1990, Peptides 1990, Giralt and Andreu, eds.,ESCOM Publ., pp. 238–20 240.
13. Fuji et al., 1987, 1988, Peptides: Chemistry and Biology, Marshall, ed., ESCOM Publ., Leiden, pp. 217–219.

There are two major classes of peptide-carbohydrate linkages. First, ether bonds join the serine or threonine hydroxyl to a hydroxyl of the sugar. Second, amide bonds join glutamate or aspartate carboxyl groups to an amino group on the sugar. In particular, references 1 and 2, supra, teach methods of preparing peptide-carbohydrate ethers and amides. Acetal and ketal bonds may also bind carbohydrate to peptide.

Fatty acyl peptide derivatives may also be prepared. For example, and not by way of limitation, a free amino group (N-terminal or lysyl) may be acylated, e.g., nyristoylated. In another embodiment an amino acid comprising an aliphatic side chain of the structure —$(CH_2)_nCH_3$ may be incorporated in the peptide. This and other peptide-fatty acid conjugates suitable for use in the present invention are disclosed in U.K. Patent GB-8809162.4, International Patent Application PCT/AU89/00166, and reference 5, supra.

Genes Encoding the Peptides of the Present Invention

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology*, John Wiley & Sons, Inc. (1994).

Therefore, if appearing herein, the following terms shall have the definitions set out below.

As used herein, the term "gene" refers to an assembly of nucleotides that encode a polypeptide, or peptide and includes cDNA and genomic DNA nucleic acids.

A "vector" is a replicon, such as plasmid, phage or cosmid, to which another DNA segment may be attached so as to bring about the replication of the attached segment. A "replicon" is any genetic element (e.g., plasmid, chromosome, virus) that functions as an autonomous unit of DNA replication in vivo, i.e., capable of replication under its own control.

A "cassette" refers to a segment of DNA that can be inserted into a vector at specific restriction sites. The segment of DNA encodes a polypeptide or peptide of interest, and the cassette and restriction sites are designed to ensure insertion of the cassette in the proper reading frame for transcription and translation.

A cell has been "transfected" by exogenous or heterologous DNA when such DNA has been introduced inside the cell. A cell has been "transformed" by exogenous or heterologous DNA when the transfected DNA effects a phenotypic change. Preferably, the transforming DNA should be integrated (covalently linked) into chromosomal DNA making up the genome of the cell.

"Heterologous" DNA refers to DNA not naturally located in the cell, or in a chromosomal site of the cell. Preferably, the heterologous DNA includes a gene foreign to the cell.

A "heterologous nucleotide sequence" as used herein is a nucleotide sequence that is added to a nucleotide sequence of the present invention by recombinant methods to form a nucleic acid which is not naturally formed in nature. Such nucleic acids can encode chimeric and/or fusion peptides/proteins. Thus the heterologous nucleotide sequence can encode peptides and/or proteins which contain regulatory and/or structural properties. In another such embodiment the heterologous nucleotide can encode a protein or peptide that functions as a means of detecting the protein or peptide encoded by the nucleotide sequence of the present invention after the recombinant nucleic acid is expressed. In still another such embodiment the heterologous nucleotide can function as a means of detecting a nucleotide sequence of the present invention. A heterologous nucleotide sequence can comprise non-coding sequences including restriction sites, regulatory sites, promoters and the like.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the non-transcribed strand of DNA (i.e., the strand having a sequence homologous to the mRNA). However, unless specifically stated otherwise, a designation of a nucleic acid includes both the non-transcribed strand referred to above, and its corresponding complementary strand. A "recombinant DNA molecule" is a DNA molecule that has undergone a molecular biological manipulation.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a $T_m$ of 55°, can be used, e.g., 5×SSC, 0.1%

SDS, 0.25% milk, and no formamide; or 30% formamide, 5×SSC, 0.5% SDS). Moderate stringency hybridization conditions correspond to a higher $T_m$, e.g., 40% formamide, with 5× or 6× SCC. High stringency hybridization conditions correspond to the highest $T_m$, e.g., 50% formamide, 5× or 6× SCC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook e al., supra, 9.50–10.51). For hybridization with shorter nucleic acids, i.e., oligonucleotides, the position of mismatches becomes more important, and the length of the oligonucleotide determines its specificity (see Sambrook et al., supra, 11.7–11.8). Preferably a minimum length for a hybridizable nucleic acid is at least about 12 nucleotides; preferably at least about 18 nucleotides; and more preferably the length is at least about 24 nucleotides; and most preferably 36 nucleotides.

In a specific embodiment, the term "standard hybridization conditions" refers to a $T_m$ of 55° C., and utilizes conditions as set forth above. In a preferred embodiment, the $T_m$ is 60° C.; in a more preferred embodiment, the $T_m$ is 65° C.

"Homologous recombination" refers to the insertion of a foreign DNA sequence of a vector in a chromosome. Preferably, the vector targets a specific chromosomal site for homologous recombination. For specific homologous recombination, the vector will contain sufficiently long regions of homology to sequences of the chromosome to allow complementary binding and incorporation of the vector into the chromosome. Longer regions of homology, and greater degrees of sequence similarity, may increase the efficiency of homologous recombination.

A DNA "coding sequence" is a double-stranded DNA sequence which is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. If the coding sequence is intended for expression in a eukaryotic cell, a polyadenylation signal and transcription termination sequence will usually be located 3' to the coding sequence.

Transcriptional and translational control sequences are DNA regulatory sequences, such as promoters, enhancers, terminators, and the like, that provide for the expression of a coding sequence in a host cell. In eukaryotic cells, polyadenylation signals are control sequences.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control" of transcriptional and translational control sequences in a cell when RNA polymerase transcribes the coding sequence into mRNA, which is then trans-RNA spliced and translated into the protein encoded by the coding sequence.

A "signal sequence" is included at the beginning of the coding sequence of a protein to be expressed on the surface of a cell. This sequence encodes a signal peptide, N-terminal to the mature polypeptide, that directs the host cell to translocate the polypeptide. The term "translocation signal sequence" is used herein to refer to this sort of signal sequence. Translocation signal sequences can be found associated with a variety of proteins native to eukaryotes and prokaryotes, and are often functional in both types of organisms.

As used herein, the term "sequence homology" in all its grammatical forms refers to the relationship between proteins that possess a "common evolutionary origin," including proteins from superfamilies (e.g., the immunoglobulin superfamily) and homologous proteins from different species (e.g., myosin light chain, etc.) [Reeck et al., Cell, 50:667 (1987)].

More specifically, a "homologue" to a particular gene or gene product, as used herein, refers to a gene or gene product (protein or peptide) that has a common evolutionary origin to the particular gene or gene product and preferably has an analogous function. Homologues are generally derived from different species e.g. rat phenylalanine hydroxylase is a homologue of human phenylalanine hydroxylase.

Accordingly, the term "sequence similarity" in all its grammatical forms refers to the degree of identity or correspondence between nucleic acid or amino acid sequences of proteins that do not share a common evolutionary origin [see Reeck et al., 1987, supra]. However, in common usage and in the instant application, the term "homologous," when modified with an adverb such as "highly," may refer to sequence similarity and not a common evolutionary origin.

In a specific embodiment, two DNA sequences are "substantially homologous" or "substantially similar" when at least about 50% (preferably at least about 75%, and most preferably at least about 90 or 95%) of the nucleotides match over the defined length of the DNA sequences. Sequences that are substantially homologous can be identified by comparing the sequences using standard software available in sequence data banks such as that defined below, or in a Southern hybridization experiment under, for example, stringent conditions as defined for that particular system. Defining appropriate hybridization conditions is within the skill of the art. See, for example, Maniatis et al., supra; DNA Cloning, Vols. I & 11, supra; Nucleic Acid Hybridization, supra.

Similarly, in a particular embodiment, two amino acid sequences are "substantially homologous" or "substantially similar" when greater than 30% of the amino acids are identical, or greater than about 60% are similar (functionally identical). Preferably, the similar or homologous sequences are identified by alignment using, for example, the GCG (Genetics Computer Group, Program Manual for the GCG Package, Version 7, Madison, Wis.) pileup program and the default parameters.

The term "corresponding to" is used herein to refer to similar or homologous sequences, whether the exact position is identical or different from the molecule to which the similarity or homology is measured. Thus, the term "corresponding to" refers to the sequence similarity, and not the numbering of the amino acid residues or nucleotide bases.

A gene encoding an antibiotic peptide of the present invention, whether genomic DNA or cDNA, can be isolated from any prokaryotic source or fungal source, preferably a bacterial source. Similarly, the corresponding nucleotide and amino acid sequences can be obtain by inspection of genomic sequences, without requiring the actual isolation of the nucleic acid.

Accordingly, any prokaryotic cell or fungal cell potentially can serve as the nucleic acid source for an antibiotic peptide or component of the His-Asp pathway or ABC transporter system of the present invention. The DNA may be obtained by standard procedures known in the art from cloned DNA (e.g., a DNA "library"), by chemical synthesis, by cDNA cloning, or by the cloning of genomic DNA, or fragments thereof, purified from the desired cell [see, for example, Sambrook et al. 1989, supra; Glover, D. M. (ed.), 1985, DNA Cloning: A Practical Approach, MRL Press, Ltd., Oxford, U.K. Vol. I, II].

A radiolabeled cDNA encoding an antibiotic peptide of the present invention can be synthesized and then used as a probe to identify homologous coding regions from among other prokaryotic genomic DNA or fragments thereof.

The present invention also relates to cloning vectors containing genes encoding the peptides of the invention. The production and use of such derivatives and analogs related to the antibiotic peptides are within the scope of the present invention.

Due to the degeneracy of nucleotide coding sequences, other DNA sequences which encode substantially the same amino acid sequence as gene encoding a peptide of the invention may be used in the practice of the present invention including those comprising conservative substitutions thereof. These include but are not limited to modified allelic genes, modified homologous genes from other species, and nucleotide sequences comprising all or portions of such genes which are altered by the substitution of different codons that encode the same amino acid residue within the sequence, thus producing a silent change.

The genes encoding peptide derivatives and analogs of the invention can be produced by various methods known in the art. The manipulations which result in their production can occur at the gene or protein level. For example, a peptide gene sequence can be produced from a native peptide clone by any of numerous strategies known in the art [Sambrook et al., 1989, supra]. The sequence can be cleaved at appropriate sites with restriction endonuclease(s), followed by further enzymatic modification if desired, isolated, and ligated in vitro. In the production of the gene encoding a derivative or analog of peptide of the present invention, care should be taken to ensure that the modified gene remains within the same translational reading frame as the original gene, uninterrupted by translational stop signals, in the gene region where the desired activity is encoded.

Additionally, nucleic acid sequence encoding a peptide of the present invention can be produced by in vitro or in vivo mutations, to create and/or destroy translation, initiation, and/or termination sequences, or to create variations in coding regions and/or form new restriction endonuclease sites or destroy preexisting ones, to facilitate further in vitro modification. Preferably such mutations will further enhance the specific properties of the gene product. Any technique for mutagenesis known in the art can be used, including but not limited to, in vitro site-directed mutagenesis [Hutchinson, C., et al., J. Biol. Chem., 253:6551 (1978); Zoller and Smith, DNA, 3:479–488 (1984); Oliphant et al., Gene, 44:177 (1986); Hutchinson et al., Proc. Natl. Acad. Sci. U.S.A., 83:710 (1986)], use of TAB® linkers (Pharmacia), etc. PCR techniques are preferred for site directed mutagenesis (see Higuchi, 1989, "Using PCR to Engineer DNA"., in PCR Technology: Principles and Applications for DNA Amplification, H. Erlich, ed., Stockton Press, Chapter 6, pp. 61–70)].

A general method for site-specific incorporation of unnatural amino acids into proteins is described in Christopher J. Noren, Spencer J. Anthony-Cahill, Michael C. Griffith, Peter G. Schultz, Science, 244:182–188 (April 1989). This method may be used to create analogs with unnatural amino acids.

The identified and isolated or synthesized gene can then be inserted into an appropriate cloning vector. An appropriate vector-host system can be selected from the large number of those known in the art.

Expression of The Proteins and Peptides of the Present Invention

The nucleotide sequence coding for a peptide or protein of the present invention, or a functionally equivalent derivative, including a chimeric peptide/protein, thereof, can be inserted into an appropriate expression vector, i.e., a vector which contains the necessary elements for the transcription and translation of the inserted protein-coding sequence. Such elements are termed herein a "promoter." Thus, the nucleic acid encoding the peptide of the invention is operationally associated with a promoter in an expression vector of the invention. Both cDNA and genomic sequences can be cloned and expressed under control of such regulatory sequences. An expression vector also preferably includes a replication origin.

The necessary transcriptional and translational signals can be provided on a recombinant expression vector, or they may be supplied by the native gene encoding the corresponding peptide and/or its flanking regions. Any person with skill in the art of molecular biology or protein chemistry, in view of the present disclosure, would readily know how to assay the protein expressed as described herein, e.g., to determine whether such a modified peptide has the antibiotic activity of the peptides of the present invention.

A recombinant protein or peptide of the present invention, or functionally equivalent derivative, or chimeric construct may be expressed clromosomally, after integration of the coding sequence by recombination. In this regard, any of a number of amplification systems may be used to achieve high levels of stable gene expression [See Sambrook el al., 1989, supra]. Chromosomal integration, e.g., by homologous recombination is desirable where permanent expression is required, such as to immortalize an antibody-producing plasma cell. In other embodiments, such as for in vitro propagation of cells for transplantation, transient transfection such as with a plasnid, is preferable. This way, the cell can be propagated indefinitely in vitro, but will terminally differentiate when reintroduced in vivo.

The cell containing the recombinant vector comprising the nucleic acid encoding an peptide of the present invention is cultured in an appropriate cell culture medium under conditions that provide for expression of the peptide by the cell.

Many methods well know in the art may be used to construct expression vectors containing a gene consisting of appropriate transcriptional/translational control signals and the protein coding sequences. These methods may include in vitro recombinant DNA and synthetic techniques and in vivo recombination (genetic recombination).

Expression of peptides or proteins of the present invention may be controlled by any promoter/enhancer element known in the art, but these regulatory elements must be functional in the host selected for expression.

Expression vectors containing a nucleic acid encoding a peptide or a protein of the present invention can be identified by four general approaches: (a) PCR amplification of the desired plasnid DNA or specific mRNA, (b) nucleic acid hybridization, (c) presence or absence of selection marker gene functions, and (d) expression of inserted sequences. In the first approach, the nucleic acids can be amplified by PCR to provide for detection of the amplified product. In the second approach, the presence of a foreign gene inserted in an expression vector can be detected by nucleic acid hybridization using probes comprising sequences that are homologous to an inserted marker gene. In the third approach, the recombinant vector/host system can be identified and selected based upon the presence or absence of certain "selection marker" gene functions (e.g., β-galactosidase activity, thymidine kinase activity, resistance to antibiotics, transformation phenotype, occlusion body formation in baculovirus, etc.) caused by the insertion of foreign genes in the vector. In another example, if the nucleic acid encoding the peptide is inserted within the "selection marker" gene sequence of the vector, recombinants containing the peptide insert can be identified by the absence of the marker gene function. In the fourth approach, recombinant expression vectors can be identified by assaying for the activity, biochemical, or immunological characteristics of the gene product expressed by the recombinant, provided that the expressed peptide or protein assumes a functionally active conformation.

The art recognizes a wide variety of host/expression vector combinations that may be employed in expressing the DNA sequences of this invention. Once a particular recombinant DNA molecule is identified and isolated, several methods known in the art may be used to propagate it. Once a suitable host system and growth conditions are established, recombinant expression vectors can be propagated and prepared in quantity.

Vectors are introduced into the desired host cells by methods known in the art, e.g., transfection, electroporation, microinjection, transduction, cell fusion, DEAE dextran, calcium phosphate precipitation, lipofection (lysosome fusion), use of a gene gun, or a DNA vector transporter [see, e.g., Wu el al., *J. Biol. Chem.* 267:963–967 (1992); Wu and Wu, *J. Biol. Chem.*, 263:14621–14624 (1988); Hartmut et al., Canadian Patent Application No. 2,012,311, filed Mar. 15, 1990)].

Antibodies to the Peptides and Proteins of the Present Invention

According to the present invention, the peptides and proteins of the present invention as produced by a recombinant source, through chemical synthesis, through the modification of a peptide of the present invention, or directly isolated from a natural sources, and derivatives or analogs thereof, including fusion proteins/peptides, may be used as an immunogen to generate antibodies that specifically recognize the peptide or protein. Such antibodies include but are not limited to polyclonal, monoclonal, chimeric, single chain, Fab fragments, and a Fab expression library. The anti-peptide antibodies of the invention may be cross reactive, that is, they may recognize an homologous peptide derived from a different naturally occurring peptide. Polyclonal antibodies have greater likelihood of cross reactivity. Alternatively, an antibody of the invention may be specific for a single form of a peptide or protein of the present invention, such as the peptide having an amino acid sequence of SEQ ID NO:2 or SEQ ID NO:44.

Various procedures known in the art may be used for the production of polyclonal antibodies to the peptides or proteins of the present invention or derivatives or analogs thereof. For the production of antibody, various host animals can be immunized by injection with the peptide, protein, or a derivative (e.g., or fusion protein) thereof, including but not limited to rabbits, mice, rats, sheep, goats, etc. In one embodiment, the peptide can be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calinette-Guerin) and *Corynebacterium parvum.*

For preparation of monoclonal antibodies directed toward the peptide, or analog, or derivative thereof, any technique that provides for the production of antibody molecules by continuous cell lines in culture may be used. These include but are not limited to the hybridoma technique originally developed by Kohler and Milstein [*Nature*, 256:495–497 (1975)], as well as the trioma technique, the human B-cell hybridoma technique [Kozbor et al., *Immunology Today*, 4:72 (1983); Cote et al., *Proc. Natl. Acad. Sci. U.S.A.*, 80:2026–2030 (1983)], and the EBV-hybridoma technique to produce human monoclonal antibodies [Cole et al., in *Monoclonal Antibodies and Cancer Therapy*, Alan R. Liss, Inc., pp. 77–96 (1985)]. In an additional embodiment of the invention, monoclonal antibodies can be produced in germ-free animals utilizing recent technology [PCT/US90/02545]. In fact, according to the invention, techniques developed for the production of "chimeric antibodies" [Morrison et al., *J. Bacteriol.*, 159:870 (1984); Neuberger et al., *Nature*, 312:604–608 (1984); Takeda et al., *Nature*, 314:452–454 (1985)] by splicing the genes from a mouse antibody molecule specific for an antibody together with genes from a human antibody molecule of appropriate biological activity can be used; such antibodies are within the scope of this invention. Such human or humanized chimeric antibodies are preferred for use in therapy of human diseases or disorders (described infra), since the human or humanized antibodies are much less likely than xenogenic antibodies to induce an immune response, in particular an allergic response, themselves.

According to the invention, techniques described for the production of single chain antibodies [U.S. Pat. Nos. 5,476,786 and 5,132,405 to Huston; U.S. Pat. No. 4,946,778] can be adapted to produce specific single chain antibodies to a peptide of the present invention. An additional embodiment of the invention utilizes the techniques described for the construction of Fab expression libraries [Huse et al., *Science*, 246:1275–1281 (1989)] to allow rapid and easy identification of monoclonal Fab fragments with the desired specificity for a peptide of the present invention, or its derivatives, or analogs.

Antibody fragments which contain the idiotype of the antibody molecule can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment, and the Fab fragments which can be generated by treating the antibody molecule with papain and a reducing agent.

In the production of antibodies, screening for the desired antibody can be accomplished by techniques known in the art, e.g., radioirnmunoassay, ELISA (enzyme-linked immunosorbent assay), "sandwich" immunoassays, iminunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hem agglutination assays), complement fixation assays, immunofluorescence assays, protein A assays, and inimunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies which recognize a specific epitope of the peptide, one may assay generated hybridomas for a product which binds to the peptide fragment containing such epitope. For selection of an antibody specific to a peptide from a particular source, one can select on the basis of positive binding with the peptide expressed by, chemically synthesized, or isolated from that specific source.

The foregoing antibodies can be used in methods known in the art relating to the localization and activity of the corresponding peptide or protein of the invention, e.g., for Western blotting, measuring levels thereof in appropriate physiological samples, etc. using any of the detection techniques mentioned herein or known in the art.

Labels

The peptides and proteins of the present invention, as well as nucleic acids that encode these peptides all can be labeled. Suitable labels include enzymes, fluorophores (e. g., fluorescein isothiocyanate (FITC), pbycoerythrin (PE), Texas red (TR), rhodamine, free or chelated lanthanide series salts, especially Eu$^{3+}$ to name a few fluorophores), chromophores, radioisotopes, chelating agents, dyes, colloidal gold, latex particles, ligands (e.g., biotin), and chemiluminescent agents. When a control marker is employed, the same or different labels may be used for the receptor and control marker.

In the instance where a radioactive label, such as the isotopes $^3$H, $^{14}$C, $^{32}$P, $^{35}$S, $^{36}$Cl, $^{51}$Cr, $^{57}$Co, $^{58}$Co, $^{59}$Fe, $^{90}$Y, $^{125}$I, $^{131}$I, and $^{186}$Re are used, known currently available counting procedures may be utilized. In the instance where the label is an enzyme, detection may be accomplished by any of the presently utilized colorimetric, spectrophotometric, fluorospectrophotometric, amperometric or gasometric techniques known in the art.

Direct labels are one example of labels which can be used according to the present invention. A direct label has been defined as an entity, which in its natural state, is readily visible, either to the naked eye, or with the aid of an optical filter and/or applied stimulation, e.g. U.V. light to promote fluorescence. Among examples of colored labels, which can be used according to the present invention, include metallic sol particles, for example, gold sol particles such as those described by Leuvering (U.S. Pat. No. 4,313,734); dye sole particles such as described by Gribnau et al. (U.S. Pat. No. 4,373,932) and May et al. (WO 88/08534); dyed latex such as described by May, supra, Snyder (EP-A 0 280 559 and 0 281 327); or dyes encapsulated in liposomes as described by Campbell et al. (U.S. Pat. No. 4,703,017). Other direct labels include a radionucleotide, a fluorescent moiety or a luminescent moiety. In addition to these direct labeling devices, indirect labels comprising enzymes can also be used according to the present invention. Various types of enzyme linked immunoassays are well known in the art, for example, alkaline phosphatase and horseradish peroxidase, lysozyme, glucose-6-phosphate dehydrogenase, lactate dehydrogenase, urease, these and others have been discussed in detail by Eva Engvall in Enzyme Immunoassay ELISA and EMIT in *Methods in Enzymology*, 70:419–439 (1980) and in U.S. Pat. No. 4,857,453.

Suitable enzymes include, but are not limited to, alkaline phosphatase and horseradish peroxidase. Other labels for use in the invention include magnetic beads or magnetic resonance imaging labels.

In another embodiment, a phosphorylation site can be created on an antibody of the invention for labeling with $^{32}$P, e.g., as described in European Patent No. 0372707 (application No. 89311108.8) by Sidney Pestka, or U.S. Pat. No. 5,459,240, issued Oct. 17, 1995 to Foxwell et al.

As exemplified herein, proteins, including antibodies, can be labeled by metabolic labeling. Metabolic labeling occurs during in vitro incubation of the cells that express the protein in the presence of culture medium supplemented with a metabolic label, such as [$^{35}$S]-methionine or [$^{32}$P]-orthophosphate. In addition to metabolic (or biosynthetic) labeling with [$^{35}$S]-methionine, the invention further contemplates labeling with [$^{14}$C]-amino acids and [$^3$H]-amino acids (with the tritium substituted at non-labile positions).

Peptide Screening

As disclosed herein, nucleic acid sequences encoding naturally occurring peptides can be identified and selected through inspection of prokaryotic (e.g., bacterial) or fungal DNA in regions encoding ABC transporter or systems, or proteins involved in His-Asp phosphorelay pathways, or analogous prokaryotic signal transduction systems. Further examples of priate peptides include those listed in Table 1 below.

TABLE 1

| | Peptide | SEQ ID NO: | Origin |
|---|---|---|---|
| 1 | NRKVFIVVLSMLLLLAMERPWCSLV | 26 | *Methanococcus jannaschii* |
| 2 | SSLLDGVKIASGNLLASTKPSGNFN | 27 | *Haemophilus influenzae* Rd |
| 3 | SRKRFHQILMQGMKLAYRIYRSSHD | 28 | *Haemophilus influenzae* Rd |
| 4 | RSDKFHSTIVLSSVLADKKTPRCCH | 29 | *Haemophilus influenzae* Rd |
| 5 | HVEELHHVVESLALLSDKVLCRNSY | 30 | *Archaeoglobus fulgidus* |
| 6 | TGREARRIISAGEILVDGVVRKDYK | 31 | *Archaeoglobus fulgidus* |

TABLE 1-continued

| Peptide | SEQ ID NO: | Origin |
|---|---|---|
| 7 RCLRRDSLFSSGCLLAGEEPSRRSC | 32 | Archaeoglobus fulgidus |
| 8 VLRTHGTVLSAKQLINAKNPSRYFG | 33 | Borrelia burgdoiferl |
| 9 LKEEFEKFRSAGEKLLDFRP | 34 | Synechocystis Sp. |
| 10 FGNQLSIGQLIA | 35 | Synechocystis Sp. |

Such peptides can be generated by synthesizing or expressing the amino acid sequence encoded. The peptide can then be tested to see if it inhibits the growth of and/or kills the bacterial cells. Alternatively, the peptide can be tested for its ability kill autolysis prone pneumococci with or alternatively without lysing the cell. In still another embodiment, the peptide is tested for acting synergistically with penicillin (or analogues thereof) for killing non growing or slow growing bacterial cells. Similarly, analogs of the natural peptide can also be prepared and then tested for their ability to kill prokaryotic cells. A particular peptide, or analog thereof is identified when it can inhibit the growth of or stimulate bacterial cell killing or lysis.

The analogs of the peptides can contain one or more conservative amino acid substitutions, or contain a portion of the naturally occurring sequence of the peptide, which has one or more conservative amino acid substitutions. Such a portion of the peptide can also be linked together in a fusion peptide or protein, and thereby contain amino acid residues that are functionally distinct from those that have been replaced.

Any person having skill in the art would recognize appropriate modifications of the peptide to make it more stable, including the use of substitutions involving unnatural amino acids as described above. Changes in the peptide also can be made to make it potentially more effective and/or more broadly applicable. Such peptide analogs are filly contemplated in the present invention.

The method for identifying a peptide that can inhibit the growth of or kill a prokaryote (e.g., a bacterium) can comprise testing the peptide for its ability to inhibit the growth of or kill an alternative strain (and/or species) of the bacterium, since not all peptides will be able to kill all bacterial strains and/or species. Alternatively, the peptide can be tested for its ability kill autolysis prone pneumococci without lysing the cell. In still another embodiment, the peptide is tested for acting synergistically with penicillin (or analogues thereof) for killing bacterial cells. Indeed, many of the peptides of the present invention will show specificity for particular species and/or strains of bacteria (or other prokaryotes). Therefore, generally, the bacterium (or prokaryote) tested will initially be one that naturally encodes the peptide.

In particular embodiments, the bacterial strain tested is a wild type strain. In other embodiments a particular mutant strain is tested. In the Examples below, the peptide having the amino acid sequence of SEQ ID NO:2 was tested in a wild type strain of Streptococcus pneumoniae, a strain deficient in the autolysin, LytA, a strain of bacteria highly tolerant to vancomycin and penicillin, and s trains of bacteria having a non-functional histidine kinase or a non-functional ABC transporter.

The ability of a peptide to inhibit the growth of or kill a particular cell and/or act synergistically with penicillin can be measured by any technique known in the art. In the Examples below, cell growth curves were performed in the presence or absence of the peptide, and monitored by the change in optical density (e.g., at 620 nm) with time. If the optical density decreases in the presence of the peptide relative to in its absence, the peptide is identified as an activator of cell lysis. If the optical density remains constant, the peptide is identified as an inhibitor of cell growth. The synergistic effect with penicillin can also be readily determined. Cell killing can be determined by measuring relative colony forming units (CFU/ml) as d described below.

Cell cultures can be readily prepared, as exemplified below, by initially growing cells to a defined concentration, e.g., having an $OD_{620}$ of 0.05–0.2. At this point the peptide can be administered to the sample, alone or together with other appropriate reagents (alternative antibiotics etc.) The cells can then be cultured for a designated time, at a designated temperature, to allow cell growth to reach a designated growth phase, e.g., stationary phase. The cell density can be determined by a number of means including by monitoring the OD at 620 nm at regular intervals, e.g., every hour. A decrease in optical density (i.e., cell concentration) is indicative of the cells being killed.

Prokaryotic cells (e.g., bacterial cells) can be constructed to have functional mutations in any or all of the open reading frames of an ABC transporter system and/or a His-Asp phosphorelay signal transduction system (including in sensor histidine kinase or a response regulator). In one such embodiment, the lack of function in a particular open reading frame is performed by insertion duplication mutagenesis, although a number of comparable methods can be used including transpose mutagenesis.

The ability of an agent, including a peptide of the present invention, to maintain antibacterial activity in the mutant cells can be readily tested as described below. Aside from the methods of identifying the potential agents (or drugs) detailed above the assays of the present invention can be used to identify agents from the huge chemical libraries that are commercially available from most large chemical companies including Merck, Glaxo Wellcome, Bristol Meyers Squib, Monsanto/Searle, Eli Lilly, Novartis and Pharmacia UpJohn. Alternatively recombinant bacteriophage may be used to produce large peptide libraries. Using the "phage method" [Scott and Smith, Science, 249:3860–390 (1990); Cwirla et al., Proc. Natl. Acad. Sci., 87:6378–6382 (1990); Devlin et al., Science, 249:404–406 (1990)], very large libraries can be constructed ($10^6$–$10^8$ chemical entities). A second approach uses primarily chemical methods, of which the Geysen method [Geysen et al., Molecular Immunology, 23:709–715 (1986); Geysen et al., J. Immunologic Method, 102:259–274 (1987)] and the method of Fodor et al. [Science, 251:767–773 (1991)] are examples. Furka et al. [14th International Congress of Biochemistry, Volume 5, Abstract FR:013 (1988); Furka, Int. J. Peptide Protein Res., 37:487–493 (1991)], Houghton [U.S. Pat. No. 4,631,211, issued December 1986] and Rutter et al. [U.S. Pat. No. 5,010,175, issued Apr. 23, 1991] describe methods to produce a mixture of peptides that can be readily tested as agents or drugs.

In another aspect, synthetic libraries [Needels et al., Proc. Natl. Acad. Sci. USA, 90:10700–4 (1993); Ohlmeyer et al., Proc. Natl. Acad. Sci. USA, 90:10922–10926 (1993); Lam et al., International Patent Publication No. WO 92/00252; Kocis et al., International Patent Publication No. WO 9428028, each of which is incorporated herein by reference in its entirety], and the like can be used to screen for drugs using the mutant cells provided by the present invention.

Diagnostics

The sensor histidine kinase having the amino acid sequence of SEQ ID NO:14, and homologues thereof, the response regulator having the amino acid sequence of SEQ ID NO:16 and homologues thereof, and a component of the ABC transporter system having the amino acid sequence of SEQ ID NO:18, SEQ ID NO:20, or SEQ ID NO:22, and homologues thereof, individually and in combination may be used as markers to identify clinically tolerant strains of bacteria as described in Example 11. Primers for the marker (s) can be prepared and the PCR amplification products can be evaluated by SSCP analysis or alternatively by restriction fragment length polymorphism (RFLP) for example. Differences in the gel patterns of the products of the SSCP procedure between a test sample and a wildtype bacterial strain allows the identification of a bacterial strain that is likely to be a tolerant strain. Such identification can be used in the epidemiological study of the spread of tolerant/ resistant traits. The greater the similarity of the changes in the sequences between two particular bacterial strains (relative to a known standard) the more closely related are the two particular sequences. Identical sequence changes indicate identical clones from the same source bacterial strain.

Administration

According to the invention, the component or components of a therapeutic composition, e.g., a peptide of the present invention and a pharmaceutically acceptable carrier, may be introduced topically, parenterally, transmucosally, e.g., orally, nasally, or rectally, or transdermally. Administration that is parenteral, e.g., via intravenous injection, also includes, but is not limited to, intra-arterial, intramuscular, intradermal, subcutaneous, intraperitoneal, intraventricular, and intracranial administration.

In a preferred aspect, a peptide of the present invention can cross cellular or nuclear membranes, which would allow for intravenous or oral administration. Strategies are available for such crossing, including but not limited to, increasing the hydrophobic nature of the peptide; introducing the peptide as a conjugate to a carrier, such as a ligand to a specific receptor, targeted to a receptor; and the like.

The present invention also provides for conjugating targetin, molecules to a peptide of the invention. "Targeting molecule" as used herein shall mean a molecule which, when administered in vivo, localizes to desired location(s). In various embodiments, the targeting molecule can be a peptide or protein, antibody, lectin, carbohydrate, or steroid. In one embodiment, the targeting molecule is a peptide ligand of a receptor on the target cell. In a specific embodiment, the targeting molecule is an antibody. Preferably, the targeting molecule is a monoclonal antibody. In one embodiment, to facilitate crosslinking the antibody can be reduced to two heavy and light chain heterodimers, or the F(ab')$_2$ fragment can be reduced, and crosslinked to the peptide via the reduced sulibydryl.

Antibodies for use as targeting molecule are specific for cell surface antigen. In one embodiment, the antigen is a receptor. For example, an antibody specific for a receptor on cell in the lung, can be used in the treatment of pneumonia. This invention further provides for the use of other targeting molecules, such as lectins, carbohydrates, proteins and steroids.

In another embodiment, the therapeutic compound can be delivered in a vesicle, in particular a liposome [see Langer, Science, 249:1527–1533 (1990); Treat et al., in *Liposomes in the Therapy of Infectious Disease and Cancer*, Lopez-Berestein and Fidler (eds.), Liss: New York, pp. 353–365 (1989); Lopez-Berestein, ibid., pp. 317–327; see generally ibid.]. To reduce its systemic side effects, this may be a preferred method for introducing a peptide of the present invention.

In yet another embodiment, the therapeutic compound can be delivered in a controlled release system For example, the peptide may be administered using intravenous infusion, an implantable osmotic pump, a transdermal patch, liposomes, or other modes of administration. In one embodiment, a pump may be used [see Langer, supra; Sefton, *CRC Crit. Ref. Biomed. Eng.*, 14:201 (1987); Buchwald et al., *Surgery*, 88:507 (1980); Saudek et al., *N. Engl. J. Med.*, 321:574 (1989)]. In another embodiment, polymeric materials can be used [see *Medical Applications of Controlled Release*, Langer and Wise (eds.), CRC Press: Boca Raton, Fla. (1974); *Controlled Drug Bioavailability, Drug Product Design and Performance*, Smolen and Ball (eds.), Wiley: New York (1984); Ranger and Peppas, *J. Macromol. Sci. Rev. Macromol. Chem.*, 23:61 (1983); see also Levy et al., Science, 228:190 (1985); During et al., *Ann. Neurol*, 25:351 (1989); Howard et al. , *J. Neurosurg.*, 71:105 (1989)]. In yet another embodiment, a controlled release system can be placed in proximty of the therapeutic target, e.g., the lungs, thus requiring only a fraction of the systemic dose [see, e.g., Goodson, in *Medical Applications of Controlled Release*, supra, vol. 2, pp. 115–138 (1984)]. Other controlled release systems are discussed in the review by Langer [*Science*, 249:1527–1533 (1990)].

Pharmaceutical Compositions. Yet another aspect of the present invention, provides pharmaceutical compositions of the above. Such pharmaceutical compositions may be for topical administration or for injection, or for oral, pulmonary, nasal or other forms of administration. In general, included in the invention are pharmaceutical compositions comprising effective amounts of a low molecular weight component or components, or derivative products, of the invention together with pharmaceutically acceptable diluents, preservatives, solubilizers, emulsifiers, adjuvants and/or carriers. Such compositions include diluents of various buffer content (e.g., Tris-HCl , acetate, phosphate), pH and ionic strength; additives such as detergents and solubilizing agents (e.g., Tween 80, Polysorbate 80), anti-oxidants (e.g., ascorbic acid, sodium metabisulfite), preservatives (e.g., pmersol, benzyl alcohol) and bulking substances (e. g., lactose, mannitol); incorporation of the material into particulate preparations of polymeric compounds such as polylactic acid, polyglycolic acid, etc. or into liposomes. Hyaluronic acid may also be used. Such compositions may influence the physical state, stability, rate of in vivo release, and rate of in vivo clearance of the present peptides and derivative s. See, e.g., Remington's Pharmaceutical Sciences, 18th Ed. [1990, Mack Publishing Co., Easton, Pa. 18042] pages 1435–1712 which are herein incorporated by reference. The compositions may be prepared in liquid form, or may be in dried powder, such as lyophilized form.

Oral Delivery. Contemplated for use herein are oral solid dosate forms, which are described generally in Remington's Pharmaceutical Sciences, 18th Ed. 1990 (Mack Publishing Co. Easton Pa. 18042) at Chapter 89, which is herein incorporated by reference. Solid dosage forms include tablets, capsules, pills, troches or lozenges, cachets or pellets. Also, liposomial or proteinoid encapsulation may be used to formulate the present compositions (as , for example, proteinoid microspheres reported in U.S. Pat. No. 4,925,673). Liposomal encapsulation may be used and the liposomes may be derivatized with various polymers (e.g., U.S. Pat. No. 5,013,556). A description of possible solid dosage forms for the therapeutic is given by Marshall, K. In: *Modern Pharmaceutics* Edited by G. S. Banker and C. T. Rhodes Chapter 10, 1979, herein incorporated by reference. In general, the formulation will include a peptide of the present invention (or chemically modified forms thereof) and inert ingredients which allow for protection against the stomach environment, and release of the biologically active material in the intestine.

Also specifically contemplated are oral dosage forms of the above derivatized peptides. The peptides may be chemically modified so that oral delivery of the derivative is efficacious. Generally, the chemical modification contemplated is the attachment of at least one moiety to the peptide itself, where said moiety permits (a) inhibition of proteolysis; and (b) uptake into the blood stream from the stomach or intestine. Also desired is the increase in overall stability of the peptide and increase in circulation time in the body. An example of such a moiety is polyethylene glycol.

For the peptide (or derivative) the location of release may be the stomach, the small intestine (the duodenum, the jejunum, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the peptide (or derivative) or by release of the biologically active material beyond the stomach environment, such as in the intestine.

The therapeutic can be included in the formulation as fine multi-particulates in the form of granules or pellets of particle size about 1 mmn The formulation of the material for capsule administration could also be as a powder, lightly compressed plugs or even as tablets. The therapeutic could be prepared by compression.

One may dilute or increase the volume of the therapeutic with an inert material. These diluents could include carbohydrates, especially mannitol, a-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form Materials used as disintegrates include but are not limited to starch, including the commercial disintegrant based on starch, Explotab. Binders also may be used to hold the therapeutic agent together to form a hard tablet and include materials from natural products such as acacia, tragacanth, starch and gelatin.

An anti-frictional agent may be included in the formulation of the therapeutic to prevent sticking during the formulation process. Lubricants may be used as a layer between the therapeutic and the die wall. Glidants that might improve the flow properties of the drug during formulation and to aid rearrangement during compression also might be added. The glidants may include starch, talc, pyrogenic silica and hydrated silicoaluminate.

In addition, to aid dissolution of the therapeutic into the aqueous environment a surfactant might be added as a wetting agent. Additives which potentially enhance uptake of the protein (or derivative) are for instance the fatty acids oleic acid, linoleic acid and linolenic acid.

Nasal Delivery. Nasal delivery of a peptide of the present invention is also contemplated. Nasal delivery allows the passage of the peptide to the blood stream directly after administering the therapeutic product to the nose, without the necessity for deposition of the peptide in the lung. Formulations for nasal delivery include those with dextran or cyclodextran.

For nasal administration, a useful device is a small, hard bottle to which a metered dose sprayer is attached. In one embodiment, the metered dose is delivered by drawing the pharmaceutical composition of the present invention solution into a chamber of defined volume, which chamber has an aperture dimensioned to aerosolize and aerosol formulation by forming a spray when a liquid in the chamber is compressed. The chamber is compressed to administer the pharmaceutical composition of the present invention. In a specific embodiment, the chamber is a piston arrangement. Such devices are commercially available.

Alternatively, a plastic squeeze bottle with an aperture or opening dimensioned to aerosolize an aerosol formulation by forming a spray when squeezed. The opening is usually found in the top of the bottle, and the top is generally tapered to partially fit in the nasal passages for efficient administration of the aerosol formulation. Preferably, the nasal inhaler will provide a metered amount of the aerosol formulation, for administration of a measured dose of the drug.

Transdermal administration. Various and numerous methods are known in the art for transdermal administration of a drug, e.g., via a transdermal patch. Transdermal patches are described in for example, U.S. Pat. No. 5,407,713, issued Apr. 18, 1995 to Rolando et al.; U.S. Pat. No. 5,352,456, issued Oct. 4, 1004 to Fallon et al.; U.S. Pat. No. 5,332,213 issued Aug. 9, 1994 to D'Angelo et al.; U.S. Pat. No. 5,336,168, issued Aug. 9, 1994 to Sibalis; U.S. Pat. No. 5,290,561, issued Mar. 1, 1994 to Farhadieh et al.; U.S. Pat. No. 5,254,346, issued Oct. 19, 1993 to Tucker et al.; U.S. Pat. No. 5,164,189, issued Nov. 17, 1992 to Berger et al.; U.S. Pat. No. 5,163,899, issued Nov. 17, 1992 to Sibalis; U.S. Pat. Nos. 5,088,977 and 5,087,240, both issued Feb. 18, 1992 to Sibalis; U.S. Pat. No. 5,008,110, issued Apr. 16, 1991 to Benecke et al.; and U.S. Pat. No. 4,921,475, issued May 1, 1990 to Sibalis, the disclosure of each of which is incorporated herein by reference in its entirety.

It can be readily appreciated that a transdermal route of administration may be enhanced by use of a dermal penetration enhancer, e.g., such as enhancers described in U.S. Pat. No. 5,164,189 (supra), U.S. Pat. No. 5,008,110 (supra), and U.S. Pat. No. 4,879,119, issued Nov. 7, 1989 to Aruga et al., the disclosure of each of which is incorporated herein by reference in its entirety.

Pulmonary Delivery. Also contemplated herein is pulmonary delivery of the pharmaceutical compositions of the present invention. A pharmaceutical composition of the present invention is delivered to the lungs of a mammal while inhaling and traverses across the lung epithelial lining to the blood stream Other reports of this include Adjei et al. [*Pharmaceutical Research*, 7:565–569 (1990); Adjei et al., *International Journal of Pharmaceutics*, 63:135–144 (1990) (Oeuprolide acetate); Braquet et al., *Journal of Cardiovascular Pharmacology*, 13(suppl. 5):143–146 (1989) (endothelin-1); Hubbard et al., *Annals of Internal Medicine*, Vol. III, pp. 206–212 (1989) ($\alpha$-1-antitrypsin); Smith et al., *J. Clin. Invest.*, 84:1145–1146 (1989) ($\alpha$-1-proteinase); Oswein et al., "Aerosolization of Proteins", *Proceedings of*

*Symposium on Respiratory Drug Delivery II*, Keystone, Colo., March, (1990) (recombinant human growth hormone); Debs et al., *J. Immunol.*, 140:3482–3488 (1988) (interferon-α and tumor necrosis factor alpha); Platz et al., U.S. Pat. No. 5,284,656 (granulocyte colony stimulating factor)]. A method and composition for pulmonary delivery of drugs for systemic effect is described in Wong et al., U.S. Pat. No. 5,451,569, issued Sep. 19, 1995.

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art. With regard to construction of the delivery device, any form of aerosolization known in the art, including but not limited to spray bottles, nebulization, atomization or pump aerosolization of a liquid formulation, and aerosolization of a dry powder formulation, can be used in the practice of the invention.

All such devices require the use of formulations suitable for the dispensing of pharmaceutical composition of the present invention (or derivative). Typically, each formulation is specific to the type of device employed and may involve the use of an appropriate propellant material, in addition to the usual diluents, adjuvants and/or carriers useful in therapy. Also, the use of liposomes, microcapsules or microspheres, inclusion complexes, or other types of carriers is contemplated. Chemically modified pharmaceutical composition of the present invention may also be prepared in different formulations depending on the type of chemical modification or the type of device employed.

Formulations suitable for use with a nebulizer, either jet or ultrasonic, will typically comprise pharmaceutical composition of the present invention (or derivative) dissolved in water at a concentration of about 0.1 to 25 mg of biologically active ingredients of a pharmaceutical composition of the present invention per mL of solution. The formulation may also include a buffer and a simple sugar (e.g., for stabilization and regulation of osmotic pressure of a pharmaceutical composition of the present invention). The nebulizer formulation may also contain a surfactant, to reduce or prevent surface induced aggregation of the pharmaceutical composition of the present invention caused by atomization of the solution in forming the aerosol.

The liquid aerosol formulations contain a pharmaceutical composition of the present invention and a dispersing agent in a physiologically acceptable diluent. The dry powder aerosol formulations of the present invention consist of a finely divided solid form of a pharmaceutical composition of the present invention and a dispersing agent. With either the liquid or dry powder aerosol formulation, the formulation must be aerosolized. That is, it must be broken down into liquid or solid particles in order to ensure that the aerosolized dose actually reaches the mucous membranes of the nasal passages or the lung. The term "aerosol particle" is used herein to describe the liquid or solid particle suitable for nasal or pulmonary administration, i.e., that will reach the mucous membranes. Other considerations, such as construction of the delivery device, additional components in the formulation, and particle characteristics are important. These aspects of nasal or pulmonary administration of a drug are well known in the art, and manipulation of formulations, aerosolization means and construction of a delivery device require at most routine experimentation by one of ordinary skill in the art.

Often, the aerosolization of a liquid or a dry powder formulation for inhalation into the lung will require a propellent. The propellant may be any propellant generally used in the art. Specific non-limiting examples of such useful propellants are a chlorofluorocarbon, a hydrofluorocarbon, a hydrochlorofluorocarbon, or a hydrocarbon, including trifluoromethane, dichlorodifluoromethane, dichlorotetrafluoroethanol, and 1,1,1,2-tetrafluoroethane, or combinations thereof.

Systems of aerosol delivery, such as the pressurized metered dose inhaler and the dry powder inhaler are disclosed in Newman, S. P., *Aerosols and the Lung*, Clarke, S. W. and Davia, D. editors, pp. 197–220 and can be used in connection with the present invention.

In general, as described in detail infra, pharmaceutical composition of the present invention is introduced into the subject in the aerosol form in an amount between about 0.01 mg per kg body weight of the mammal up to about 1 mg per kg body weight of said mammal. In a specific embodiment, the dosage is administered as needed. One of ordinary skill in the art can readily determine a volume or weight of aerosol corresponding to this dosage based on the concentration of pharmaceutical composition of the present invention in an aerosol formulation of the invention.

Liquid Aerosol Formulations. The present invention provides aerosol formulations and dosage forms. In general such dosage forms contain a pharmaceutical composition of the present invention in a pharmaceutically acceptable diluent. Pharmaceutically acceptable diluents include but are not limited to sterile water, saline, buffered saline, dextrose solution, and the like.

The formulation may include a carrier. The carrier is a macromolecule which is soluble in the circulatory system and which is physiologically acceptable where physiological acceptance means that those of skill in the art would accept injection of said carrier into a patient as part of a therapeutic regime. The carrier preferably is relatively stable in the circulatory system with an acceptable plasma half life for clearance. Such macromolecules include but are not limited to Soya lecithin, oleic acid and sorbitan trioleate, with sorbitan trioleate preferred.

The formulations of the present embodiment may also include other agents useful for pH maintenance, solution stabilization, or for the regulation of osmotic pressure.

Aerosol Dry Powder Formulations. It is also contemplated that the present aerosol formulation can be prepared as a dry powder formulation comprising a finely divided powder form of pharmaceutical composition of the present invention and a dispersant.

Formulations for dispensing from a powder inhaler device will comprise a finely divided dry powder containing pharmaceutical composition of the present invention (or derivative) and may also include a bulking agent, such as lactose, sorbitol, sucrose, or mannitol in amounts which facilitate dispersal of the powder from the device, e.g., 50 to 90% by weight of the formulation. The pharmaceutical composition of the present invention (or derivative) should most advantageously be prepared in particulate form with an average particle size of less than 10 mm (or microns), most preferably 0.5 to 5 mm, for most effective delivery to the distal lung.

Methods of Treatment, Methods of Preparing a Medicament. In yet another aspect of the present invention, methods of treatment and manufacture of a medicament are provided. Conditions alleviated or modulated by the administration of the present derivatives are those indicated above.

Dosages. For all of the above molecules, as further studies are conducted, information will emerge regarding appropriate dosage levels for treatment of various conditions in various patients, and the ordinary skilled worker, considering the therapeutic context, age and general health of the recipient, will be able to ascertain proper dosing. Similarly, any person having skill in the art of medicine would be able to determine appropriate doses for individuals from corresponding in vitro or animal studies without undue experimentation.

Administration with other compounds. For treatment of bacterial infections or related diseases one may administer the peptides of the present invention (or derivatives) in conjunction with other antibiotics including penicillin-like antibiotics (including penicillin itself), aminoglygoside antibiotics, macrolide antibiotics, antifungals, tetracyclines, cephalosporins, chloramphenicol and the like.

Thus, the peptides of the present invention can be delivered by topically, intravenous, intraarterial, intraperitoneal, intramuscular, or subcutaneous routes of administration. Alternatively, such a peptide, properly formulated, can be administered by nasal or oral administration. A constant supply of the peptide can be ensured by providing a therapeutically effective dose (i.e., a dose effective to induce prokaryotic cell lysis in a subject) at the necessary intervals, e.g., daily, every 12 hours, etc. These parameters will depend on the severity of the disease condition being treated, other actions, such as diet modification, that are implemented, the weight, age, and sex of the subject, and other criteria, which can be readily determined according to standard good medical practice by those of skill in the art.

A subject in whom administration of a peptide of the present invention is an effective therapeutic regiment for bacterial infections and inflarumations is preferably a human, but can be any animal. Thus, as can be readily appreciated by one of any person having skill in the art, the methods and pharmaceutical compositions of the present invention are particularly suited to administration to any animal, particularly a mammal, and including, but by no means limited to, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, etc., avian species, such as chickens, turkeys, songbirds, etc., i.e., for veterinary medical use.

The various peptides of the present invention, corresponding peptide analogs, nucleic acids encoding the same, and pharmaceutical compositions containing the same may be used in the treatment and or prevention of any disease caused by a bacterium, such as by, *Staphylococcus aureus*, Acinetobactor, *Enterococcus faecalis, Escherichia coli, Pseudomonas aeruginosa*, all of which can cause blood poisoning among other ailments; *Mycobacterium tuberculosis* which causes tuberculosis; *Shigella dysenteria* which causes dysentery; and *Neisseria gonorrhoeae* which causes gonorrhoea. As exemplified below, in preferred embodiment, a peptide is identified that is useful in the treatment of infections due to *Streptococcus pneumnonziae*, a bacterial species that causes blood poisoning, middle ear infections, pneumonia, and meningitis in humans.

The present invention mnay be better understood by reference to the following non-limiting Examples, which are provided as exemplary of the invention. The following examples are presented in order to more fully illustrate the preferred embodiments of the invention. It should in no way be construed, however, as limiting the broad scope of the invention.

EXAMPLE 1

IDENTIFICATION OF AN ANTIBIOTIC PEPTIDE FROM *STREPTOCOCCUS PNEUMONIAE*

Introduction

All bacteria contain lytic enzymes that sever the peptidoglycan of the bacterial cell wall to allow bacterial growth. For unknown reasons, some bacteria activate these enzymes in stationary phase so as to undergo suicidal lysis (e.g., pneumococcus, *Haeinophilus influenzae*, and Neisseria species). Not surprisingly, these lytic enzymes are highly regulated to avoid autolytic suicide. Indeed, the antibiotic penicillin kills bacteria by activating these nascent lytic enzymes.

Pneumococcus is a particularly good model system for identifying novel antibiotics which act independently of these lytic enzymes because prieuwiococcus contains only one such lytic enzyme, the autolysin Lyt A. Therefore, the loss of LytA function, e.g. due to a mutation such as in Lyt 4-4, provides a strain which can be killed only by activity independent of Lyt A. Pneumococcus naturally activates Lyt A when the cells are in stationary phase. Therefore, natural activators of Lyt A would be anticipated to be present during stationary phase. However, no such natural activator of Lyt A has been identified to date.

Antibiotics exhibit a range of activities useful in controlling infections. All useful antibiotics inhibit bacterial growth (bacteristasis). Some useful antibiotics also kill bacteria (bactericidal). This is a particularly useful property since the course of treatment is often shorter if the antibiotic is bactericidal. Bactericidal antibiotics usually engender bacterial lysis as part of the mechanism of killing.

However, it has been suggested that bacterial lysis contributes to inflammation and can transiently worsen the course of disease. Thus, the optimal antibacterial effect is to kill bacteria without lysis. For pneumococci, and several other common pathogens, killing by any antibiotic is always accompanied by lysis because of the activity of the autolysin, which is obligately tied to bacterial killing by these drugs. The characterization of the peptide to follow demonstrates that it is a bactericidal agent that kills autolysis prone pneumococci without lysis. This is a novel and highly desirable activity.

Methods

Peptide Synthesis: Peptides were synthesized in the Center for Biotechnology at St. Jude Children's Research Hospital using a Perkin-Elmer Applied Biosystems 433A peptide synthesizer. Synthesis was done with preloaded p-hydroxymethylphenoxymethyl-polystyrene (HMP) resins (Applied Biosystems) using 1-hydroxybenzotriazole/2-(1H-benzotriazol-1-yl),-1,1,3,3-tetramethyluronium hex afluorophosphate (HOBt/HBTU) coupling methods on 9-fluorenylmethyloxycarbonyl (FMOC) protected amino acids. In some cases, the first amino acid was manually loaded on a chmorotrityl chloride resin (Calbiochem) according to the manufacturer's instructions prior to placing the resin in the synthesizer. FMOC protected amino acids were obtained from Anaspec. For peptides containing more than one arginine, protected arginines with pentamethyldihydrobenzofuransulfonyl (Pbf) and 2,2,5,7,8-pentamethyl-chroman-6-sulfonyl (Pmc) side chain protection were alternated throughout the peptide sequence. Phosphoserine was incorporated as the FMOC-Ser(benzylphospho) protected amino acid (Calbiochem). Phosphotyrosine was incorporated as FMOC-Tyr(Dimethyl-phospho) derivatives. If conductivity measurements of the FMOC removal step fell below acceptable levels, the instrument automatically adds a second extended coupling of DMSO of the next amino acid and adds and acetic anhydride capping step. In some cases, a second extended coupling in dimethyl sulfoxide (DMSO) was manually inserted into the cycle to improve efficiency on difficult sequences. In the event that the coupling is still incomplete, a third extended coupling step is performed with 0.4 M LiCl added in the coupling step. Cleavage is performed in 89% TFA, 2% ethanedithiol, 4% thioarisole, 4% phenol, and 7% water (the water is omitted in the case of amino terminal glutamic acid) at room temperature for 2 hours. For peptides containing more than two arginines, cleavage time was extended by one hour for each additional arginine. Peptides containing phosphotyrosine were cleaved by one hour for each additional arginine. Peptides containing phosphotyrosine were cleaved in 69% TFA, 11% thioanisole, 6% ethanedithiol, 13% trimethylsilyl bromide and 2% m-cresol at 4° C. overnight. Cleaved peptides were recovered and precipitated with cold diethyl ether, then dissolved in water and lyophilized. Peptides containing phophotyrosine were dissolved in 5% ammonium bicarbonate and desalted on a disposable prepacked column containing a cross-linked dextran gel in beaded form, DNA Grade SEPHADEX™ G-25 (NAP-25) columns (Pharmacia) with water as the eluent.

Genotne Analysis: Genome analysis was performed using the FASTA, TFASTA, BLAST, and BLASTN programs. Nucleotide sequence SEQ ID NO:1 or amino acid sequence SEQ ID NO:2 were used to search existing public databases containing the multiple bacterial genomes. Homologues were found in Methanococcus, Haemophilus, Archaeoglobus, Borrelia, and Synechocystis.

Cell growth curves were performed in the presence or absence of the test reagents as specified. In short, samples were prepared as follows: 1 ml of a pneumococcus culture was placed into 10 ml of prewarmed Semisynthetic (C+Y) medium The optical density (OD) of the bacteria was monitored at 620 nm until an OD of approximately 0.1 was reached. At this point the test reagents were administered to the samples. The cells were cultured for up to 11 hours at 37° Celsius, and the OD at 620 nm was monitored every hour. A decrease in OD 620 is indicative of cell lysis, an increase is indicative of bacterial growth. No change in optical density indicates growth inhibition.

Results

The open reading frames in a gene cluster encoding an ABC transporter and a two component His-Asp phosphorelay pathway of Streptococcus pneumoniae were examined in pursuit of a putative peptide that might be involved in autolysis. Open reading Frames W1 having a nucleic acid sequence of SEQ ID NO:21, and encoding the amino acid sequence of SEQ ID NO:22, W2 having a nucleic acid sequence of SEQ ID NO:19, and encoding the amino acid sequence of SEQ ID NO:20, and W3 having a nucleic acid sequence of SEQ ID NO:17, and encoding the amino acid sequence of SEQ ID NO:18 together encode an ABC transporter [see ORF W1–W3 in FIG. 1, note that W3 is in between W1 and W2]. These sequences are just upstream of open reading frame RR/HK which encodes a response regulator (RR) having a nucleic acid sequence of SEQ ID NO:15, and an amino acid sequence of SEQ ID NO:16, and a sensor histidine kinase (HK) having a nucleic acid sequence of SEQ ID NO:13, and an amino acid sequence of SEQ ID NO:14.

An additional short open reading frame is located in between ORF W1–W3 and RR/HK at approximately position 6500 (P). This short open reading frame (P) has a nucleotide sequence of SEQ ID NO:1 and encodes a number of peptides including a peptide containing twenty-five amino acids having an amino acid sequence of SEQ ID NO:2; a peptide containing twenty-seven amino acids having an amino acid sequence of SEQ ID NO:44; and a peptide containing thirty amino acids having an amino acid sequence of SEQ ID NO:48.

The peptide having amino acid sequence SEQ ID NO:2 was chemically synthesized and tested for growth inhibiting, killing and lytic activity in Streptococcus pneumnonziae cultures.

Figure 2B:
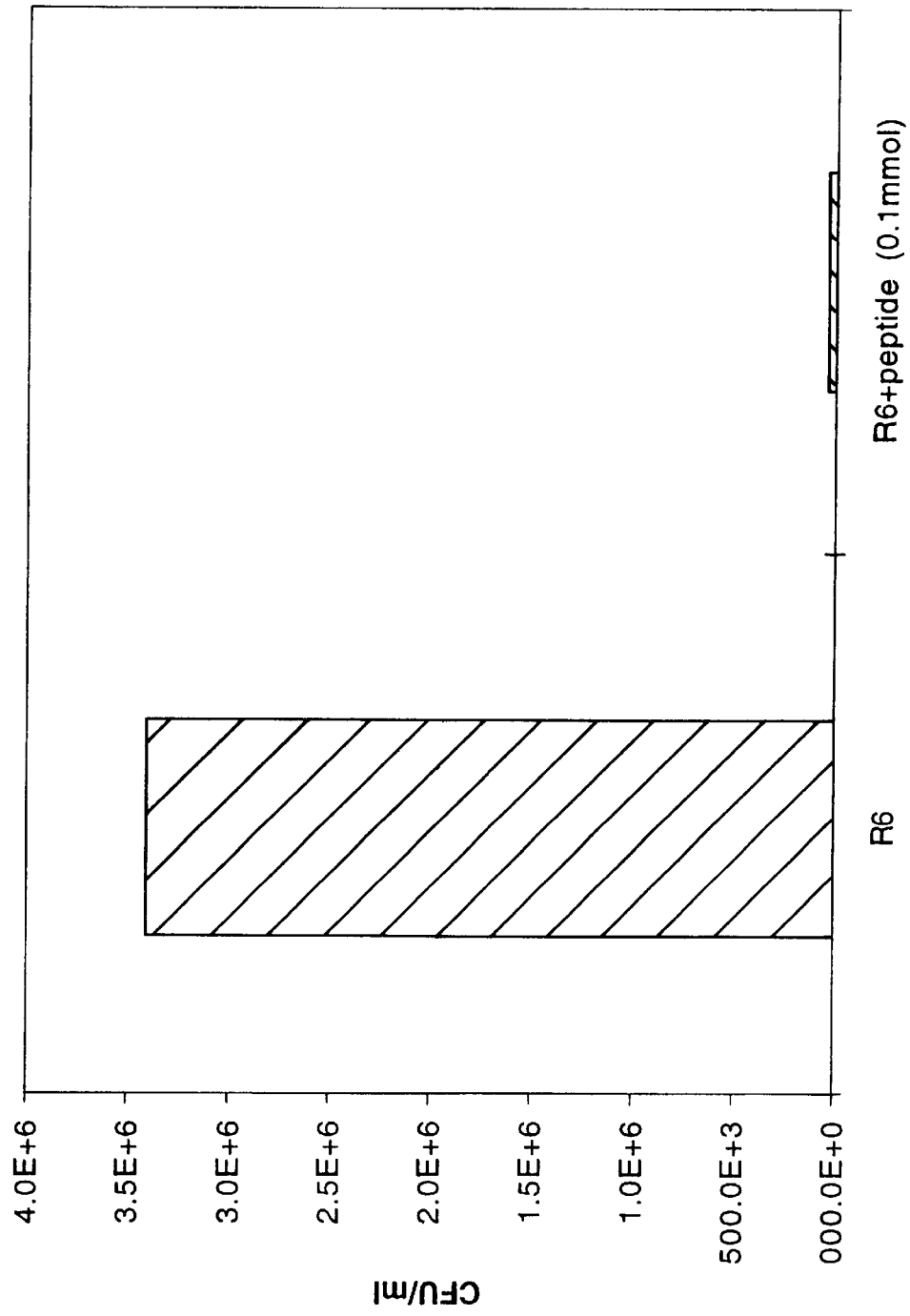

To characterize the antibacterial activity of the peptide, pneumococcal strain R6 which is sensitive to penicillin was exposed to 0.1 mM of the peptide having the amino acid sequence of SEQ ID NO:2 at an optical density of 0.01 (bacterial density of $3 \times 10^6$ cfu/ml). Bacterial growth as measured by optical density was followed for 11 hours and viability was assessed by plating on blood agar. As shown in FIG. 2A, the peptide completely inhibited growth of the bacteria. No lysis was detected. Further, the bacteria were rapidly killed as shown in FIG. 2B. Four hours after the start of the experiment, the control strain grew from $3 \times 10^6$ to $1.2 \times 10^7$ cfu/ml. In contrast, four hours after addition of the peptide, the viable bacterial number decreased from $3 \times 10^6$ to $3 \times 10^4$ CFU/ml ($10^3$-fold lower than the control).

Figure 3:
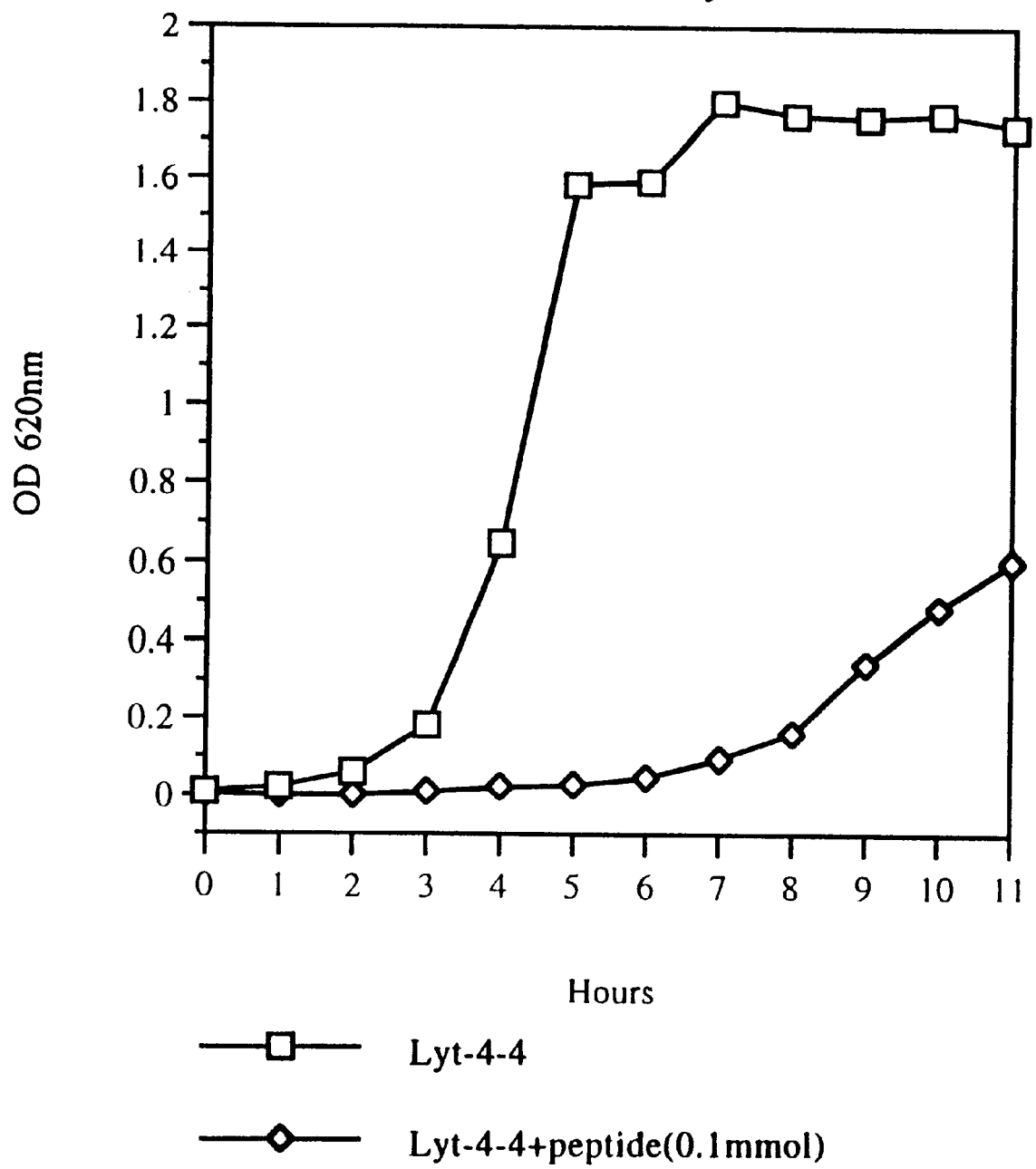
FIG. 3 shows the change in optical density at 620 nm of bacterial cultures plotted against time (hours) in the absence or presence of the peptide having the amino acid sequence of SEQ ID NO:2. The addition of the additives were made at time "0" hours. The strain of bacteria cultured was the Lyt-4-4 strain of *Streptococcus pneumoniae* which harbors a mutation leading to the loss of LytA activity. The peptide having the amino acid sequence of SEQ ID NO:2 was added as indicated at a concentration of 0.1 mM. Lyt-4-4 lacks active autolysin LytA and is therefore tolerant to penicillin treatment.

This antibacterial effect was also demonstrable in bacteria mutated so as to prevent autolysis by point mutation in the autolysin, as in the autolysin deficient strain Lyt 4-4. As shown in FIG. 3, the bactericidal activity of the peptide was demonstrable in strain Lyt 4-4 despite the absence of autolytic activity.

These results demonstrate that the peptide having an amino acid sequence of SEQ ID NO:2 not only kills wild type bacterial cells but, more importantly, kills Lyt A mutant tolerant strains as well. Furthermore, as shown below in Example 9, it activates lysis of growth arrested cells where penicillin alone fails. Therefore the results disclosed herein indicate that the mechanism of action of the antibiotic peptide differs from that of penicillin and is novel. Furthermore, these results demonstrate that the mechanism of action of the antibiotic peptide is novel in that it is independent of LytA and of bacterial growth arrest.

EXAMPLE 2

DOSE RESPONSE OF THE PEPTIDE

Figure 4:
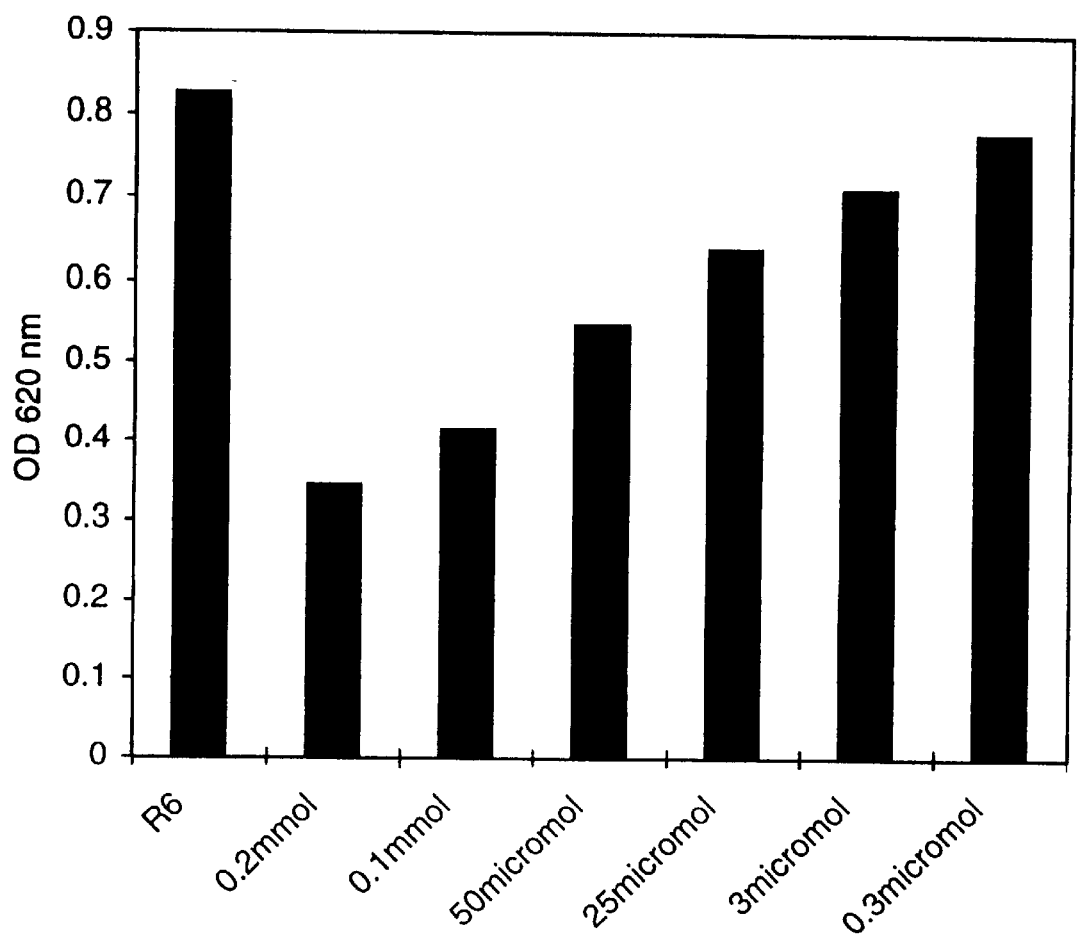
FIG. 4 shows the titration of the concentration of the peptide having an amino acid sequence of SEQ ID NO:2 with the decrease in optical density at 620 nM of R6 bacterial cultures. The effect was measured four hours after the addition of the peptide having the amino acid sequence of SEQ ID NO:2.

To determine the range of concentrations of the peptide saving the amino acid sequence of SEQ ID NO:2) that displayed antibacterial activity, pneumococcal strain R6 was subjected to various amounts of peptide and the rate of growth was measured as optical density of the culture over a period of 4 hours. As shown in FIG. 4, the peptide exhibited a dose dependent antibacterial activity. The minimum effective concentration was found to be 50–100 nM. The molecular weight of the peptide is 2940, indicating that the minimum effective concentration (MEC) can be defined as 50–100 nM or 0.15–0.3 µg/ml. Addition of more peptide was more effective at inducing growth arrest. This behavior is distinct from all other antibiotics described to date which have a clear cut minimum inhibitory concentration (MIC) above which all antibacterial activity is manifest and can not be increased further, i.e. increasing the dose above approximately 10× MIC does not further increase antibacterial efficacy. The fact that the peptide is active in the range below 1 μg/ml places the potency of its antibacterial effect in the same range as conventional antibiotics.

EXAMPLE 3

EFFECT OF PEPTIDE SEQUENCE ON BIOACTIVITY

The ability of the peptide to inhibit bacterial growth was compared using the native sequence and several variant sequences. Variants tested are as follows with the changes in sequence underlined. (Note: Peptide 7 was not tested):

original sequence (Peptide 1): MRKEFHNVLSSGQL-LADKRPARDYN (SEQ ID NO:2)

Peptide 2: (24Y-A): MRKEFHNVLSSGQLLAD-KRPARDAN (SEQ ID NO:6)

Peptide 3: (11S-A): MRKEFHNVLS AGQLLADKRPARDYN (SEQ ID NO:4)

Peptide 4: (14N truncate): MRKEFHNVLSSGQL (SEQ ID NO:8)

Peptide 5: (11C truncate): LADKRPARDYN (SEQ ID NO:10)

Peptide 6: (27): MRKEFHNVLSSGQLLADKRPAR-DYNRK(SEQ ID NO:44)

Peptide 7: (27, 11S-A) MRKEFHNVLS AGQLLADKRPARDYNRK(SEQ ID NO:47)

As shown in FIG. 5, peptides at 100 μM concentration were added to growing R6 cells at an OD 620 nm of 0.1. R6 with no peptide was the control and underwent exponential growth. The native peptide sequence having SEQ ID NO:2 (Peptide 1) demonstrated a significant delay in the onset of bacterial growth consistent with previous documentation of antibacterial activity. Peptide 6 having SEQ ID NO:44 and containing two additional c-terminal amino acids had the same effect, (although not shown in the figure). Exponential growth equal to untreated bacteria was observed with Peptides 4 and 5 indicating that the N-terminal or C-terminal end of the peptide by themselves have a markedly decreased anti-bacterial activity. Furthermore, the loss of the carboxypenultimate tyrosine (in this case replacement by alanine) in Peptide 2 also led to greatly decreased anti-bacterial activity. In direct contrast, Peptide 3 showed a greatly enhanced antibacterial effect, indicating that changing the serine-serine to serine-alanine was a preferred modification of the peptide. This enhanced activity may result from an improvement in folding of the peptide or greater access to the bacterial target.

The DNA sequence encoding the peptide, having the amino acid sequence of SEQ ID NO:2, has an alternative methionine initiation site nine nucleotides upstream of the start site for transcription of the native peptide. To determine if this peptide, which is three amino acids longer, was antibacterial, the following peptide was synthesized (changes underlined):

MEFMRKEFHNVLSSGQLLADKRPARDYN (SEQ ID NO:12)

This peptide demonstrated no antibacterial activity against R6 suggesting that at least this extension of the amino terminus is not a desirable modification of the peptide.

EXAMPLE 4

OTHER FEATURES OF THE ANTIBIOTIC ACTIVITY OF THE PEPTIDE

Strains of pneumococcus that are tolerant to penicillin, such as Lyt 4-4, grow in long chains as compared to the diplococcal morphology of wild type pneumococci. FIG. 6A illustrates these chains, which extend to 30–50 bacteria in length. Addition of the peptide to the medium (0.5 mM concentration) results in reversion of the chains to diplococci as seen in FIG. 6B. This change in bacterial morphology demonstrates that the activity of the peptide can override a loss in Lyt A activity, thereby further demonstrating the ability of the peptide to overcome tolerance.

EXAMPLE 5

THE PEPTIDE IS CO-TRANSCRIBED WITH THE CONTIGUOUS ABC TRANSPORTER

The gene encoding the peptide lies in the intergenic region between the ABC transporter complex ORF W and the two component response regulator/histidine kinase, (RR/HK) system To establish that the peptide is transcribed in wild type pneumococci, Northern analysis was performed. Total RNA was prepared according to the Qiagen manufacturer's protocol. 20 μg of RNA was separated in a 1.2% formaldehyde gel. The gel was rinsed and RNA was transferred to nylon membranes (Hybond-N, Amershame, Inc.) by capillary blotting. A PCR fragment was generated by primers flanking the gene for the peptide but within the intergenic region between the ABC transporter and the RR/HK:5'AATGAGTCTAGAATAAAGATTGC3' (SEQ ID NO:37) (9 residues downstream of the termination codon of ORF W2) and 3'CCCATCCATAAATAAGATTCT5' (SEQ ID NO:38) (beginning at the C at the second residue in the termination codon of the peptide). The PCR fragment was labeled with $\alpha^{32}$P[dCTP] and used as a probe for the product of the peptide gene. Northern analysis of ptneumococcal RNA indicated a single transcript at slightly larger than 1.4 kB (FIG. 7). The size indicates the peptide is most likely co-transcribed with the contiguous upstream ORF W3 in the ABC transporter system This further indicates that similar peptides in other bacterial species may maintain this geographic location being close to an ABC transporter. The peptide may alternatively be contiguous to a RR/HK. This may be preferred as it is reasonable to suggest that the transporter and two component RR/HK system may participate in the biological effect of the peptide.

EXAMPLE 6

MUTANTS OF THE ABC TRANSPORTER AND TWO COMPONENT (RR/HK) SYSTEM

Bacterial strains and growth conditions: The parental strain of S. pneumoniae used in these studies was R6x [Tiraby et al., Proc. Natl. Acad. Sci. USA, 70:3541–3545 (1973)], a derivative of the unencapsulated Rockefeller strain R36A [Avery et al., J. Ex. Med., 79:137–158 (1944)]. Pneumococci were routinely grown on tryptic soy agar (TSA, Difco) supplemented with sheep blood to a final concentration of 3% (v/v). For growth in liquid culture, the bacteria were grown in a semi-synthetic casein hydrolysate medium supplemented with yeast extract (C+Y, [Lacks et al., Biochem. Biophys. Acta, 39:508–517 (1960)]). For the selection and maintenance of pneumococci containing chromosomally integrated plasmids, bacteria were grown in the presence of 1 μg/ml erythromycin and/or 250 μg/ml kanamycin.

The expression of LytA was assessed by irnmunoblot of crude autolysin preparations. Bacteria were grown to $OD_{620}$ of 0.1, centrifuged at 5000×g for 10 min and resuspended in 200 μl prechilled 20 mM $KPO_4$ buffer. The suspension was quick frozen in a mixture of dry ice and ethanol, slowly thawed on ice and sonicated with glass beads for 1 min. The supernatant was centrifuged at 16000×g for 45 min at 4° C. and frozen at −20° C. The autolysin preparation was analyzed by 10% sodium dodecyl sulfate polyacrylamide gel electrophoresis and by immunoblotting after electrophoretic transfer to Immobilon-P membranes (Millipore Corporation, Bedford, Mass.). The membrane was incubated with rabbit polyclonal anti-autolysin antiserum (1:1000) and developed using goat anti-rabbit horseradish peroxidase conjugated anti-lgG (1:10,000; ECL Chemiluminescence Kit, Amersham).

DNA sequencing: The nucleotide sequences were amplified by PCR. Products were gel purified and sequenced at the St. Jude Center for Biotechnology.

Construction of mutations: Insertion duplication mutagenesis was carried out using PCR to generate gene fragments for homologous recombination proximal to the amino terminus of Orf W1, HK or RR as follows:

OrfW1: 435 bp gene fragment spanning residues 473 (EcoR1 site) to 908 (BamH1 site) of SEQ ID NO:21.

RR: 371 bp gene fragment spanning residues 142 (EcoR1 site) to 513 (BamH1 site) of SEQ ID NO:15.

HK: 411 bp gene fragment spanning residues 279 (EcoR1 site) to 690 (BamH1 site) of SEQ ID NO:13.

PCR fragments were ligated into pJDC9. Selection for double crossover homologous recombination was made using erythromycin and the insertion was confirmed by PCR.

Phenotypes of the mutants: The mutants were assessed for various physiological functions characteristic of pneumococci. This included lysis by penicillin, vancomycin, and the detergent deoxycholate (DOC). Other capabilities tested included ability to undergo natural DNA transformation (Transform) and expression of the LytA protein as assessed by Western blot. All mutants grew at the normal 30–40 minute doubling time and formed the classical diplococcal morphology. The data are summarized in the Table below.

TABLE 2

| Gene | Lysis by: | | | DNA | Expression of: |
| --- | --- | --- | --- | --- | --- |
| | Penicillin | Vancomycin | DOC | Transform | LytA |
| Orf W1 | tolerant | tolerant | no | deficient | present |
| RR | sensitive | sensitive | yes | normal | present |
| HK | tolerant | tolerant | yes | normal | present |

Conclusion

These mutant cells are useful for a screen for novel antibiotics that are effective against penicillin and/or vancomycin tolerant bacterial strains.

ACTIVITY OF THE PEPTIDE ON MUTANTS IN THE CONTIGUOUS ABC TRANSPORTER AND TWO COMPONENT SYSTEM

As described in Example 6, using insertion duplication mutagenesis, loss of function mutations were obtained in each of the 3 open reading frames of the ABC transporter and each of the two parts of the RR/HK. All 3 mutants displayed a similar phenotype. They failed to lyse and die with growth inhibitory concentrations of penicillin, i.e. both characteristics of tolerance. These parallel phenotypes further implicate these topographically close genes in a common pathway.

In addition to tolerance to penicillin, they also exhibited tolerance to vancomycin. Vancomycin is the only antibiotic that maintains efficacy against many strains of highly antibiotic resistant bacteria, such as staphylococci, enterococci and pneumococci. Escape from antibiotic activity of vancomycin has been detected in rare staphylococci and enterococci but not in pneuniococci as yet. This is an important issue as such a development would suggest an end to the ability to effectively treat these pathogens since there are no alternative antibiotics effective against multiply resistant strains [Friedland et al., Pediatr. Infect. Dis. J., 12:196–200 (1993); Marton et al., J. Infect. Dis., 163:542–8 (1991); and Bradley et al., Pediatr. Infect. Dis., 14:1037–1041 (1995)]. The commonality of the phenotype of the mutants in these contiguous genes suggests that they participate in the same biological pathway. If they created a phenotype which was corrected by exogenous peptide, they may participate in the biological activity of the peptide. For instance, the ABC transporter may transport the peptide and the HK may serve as an extracellular receptor for the peptide which then changes the behavior of the bacteria (i.e. killing) via a RR signal. Such a paradigm for transport and sensing of the peptide has been demonstrated for the property of competence for DNA transformation in pneuniococci [Havarstein et al., Proc. Natl. Acad. Sci. USA, 92:11140–11144 (1995); Havarstein et al., Mol. Microbiol., 21:965–971 (1996); Hui et al., J. Bacteriol., 173:372–381 (1991); and Cheng et al., Mol. Microbiol., 23:683–692 (1997)].

To test this hypothesis the ability of the peptide having the amino acid sequence of SEQ ID NO:2 to maintain antibacterial activity in the mutants was examined. The peptide was not able to inhibit growth of the mutant in ORF W1 suggesting that the ABC transporter is needed for the bacteria to respond to the peptide even if added from the outside. The peptide also did not function to inhibit the growth of the RR/HK mutants suggesting that the presence of this two component system is required for activity of the peptide even if added exogenously, a finding compatible with the RR/HK being a receptor for the peptide or its signal. These results demonstrate that the peptide will be active against bacteria that harbor an appropriate homologous RR/HK, in particular streptococci, enterococci, and staphylococci. Furthermore, bacteria which are tolerant by virtue of phenotypic tolerance due to slow growth rate or mutations in genes other than the RRJHK will be susceptible to the antibacterial effect of the peptide.

EXAMPLE 8

ACTIVITY OF THE PEPTIDE ON A CLINICAL ISOLATE OF PNEUMOCOCCUS HIGHLY TOLERANT TO PENICILLIN AND VANCOMYCIN

Tolerance to penicillin occurs in bacteria that fail to trigger autolysins in response to the drug. Thus, they do not undergo the classical antibiotic induced lysis and death. This is a mechanism of resistance to these drugs and is a serious emerging medical problem. While tolerance to penicillin is commonly shared with other β lactam antibiotics such as cephalosporins, this tolerance does not routinely extend to other classes of antibiotics such as vancomycin. However, one pneumococcal strain that fails to lyse and dies slowly in response to both penicillin and vancomycin is the clinical isolate A144. This combination of traits makes A144 recalcitrant to therapy. FIG. 8 compares the activity of penicillin, vancomycin, and the peptide against a classical sensitive strain, R6, and the tolerant strain A144. R6 is killed >3 logs by all three therapies within one hour. In contrast, strain A144 loses only 0.5 logs of viability in the same time period for all three therapies. Addition of the peptide (0.1 mM) early in the growth cycle, however, (FIG. 9) significantly inhibits the growth of strain A144 for 4 hours. Thereafter the bacteria grew more slowly than untreated controls. These data show that the peptide has bacteriostatic antibacterial activity against strain A144 that is greater than conventional antibiotics although its bactericidal activity is similar.

EXAMPLE 9

ABILITY OF THE PEPTIDE TO SYNERGIZE WITH PENICILLIN ON PHENOTYPICALLY TOLERANT BACTERIA

When bacteria grow slowly or stop growing due to nutrient deprivation, they become tolerant to antibiotics of all classes. This is relevant to the clinical setting because many body sites do not provide adequate nutrients for optimal bacterial growth and therefore bacteria commonly grow slowly. This prolongs the course of antibiotics needed to treat these infections. For instance, many weeks of therapy are required to treat endocarditis and osteomyelitis secondary to slowly growing bacteria. An in vitro example of phenotypic tolerance is shown in FIG. 10 where pneumococcus R6 has been transferred at time 0 to a medium lacking the essential amino acid lysine. Penicillin was added 5 min after the transfer. Normally penicillin lyses R6 within one hour of addition at 10× MIC. However, these non-growing bacteria show only a minimal response to penicillin and viability is unaffected (phenotypic tolerance). This same response is seen with the peptide. However, the addition of the peptide and penicillin together causes a dramatic lysis and loss of viability. These results indicate that the peptide in combination with β lactam antibiotics can be used to overcome phenotypic tolerance and improve the bactericidal effect of conventional antibiotics.

EXAMPLE 10

ABILITY OF THE PEPTIDE TO ACT SYNERGETISTICALLY WITH PENICILLIN IN CELLS HAVING NON-FUNCTIONAL HK AND/ OR ABC TRANSPORTER GENES

F79 is a natural isolate of pneumococcus with mutations in the HK and the ABC transporter genes as determined by SSCP (see Example 11). This strain is tolerant to penicillin and vancomycin. Addition of the peptide together with penicillin overcomes the tolerance and enables bacteriolysis, as shown in FIG. 11A. FIG. 11B shows that a mutation in HK created in the laboratory (strain Van S) mimnics the phenotype of the clinical isolate F79. Specifically, the addition of peptide together with penicillin overcomes the tolerance of the HK mutant to penicillin alone. It should be noted that strain Van S is not responsive to peptide alone, consistent with HK functioning as the receptor for the peptide.

These experiments demonstrate that the novel peptide could be a useful drug for treatment of infections by these types of tolerant strains. Van S could be a useful strain for screening for antibacterial compounds.

EXAMPLE 11

SSCP ANALYSIS OF CLINICAL ISOLATES AS AN EPIDEMIOLOGICAL TOOL TO TRACK TOLERANCE

The tolerance genes can serve as genetic markers for clinically tolerant strains. The frequency of defects in HK/RR/orfW in clinical isolates can be determined using single-strand conformation polymorphism (SSCP). This technique rapidly detects even single base pair changes in DNA sequence and is suitable for analyzing a large number of strains quickly [Stone et al., Science, 275:668–670 (1997)].

Method: Primers were selected from available sequence of HK, RR, and orfW. PCR amplification products were evaluated by SSCP analysis as follows. 12 ng of DNA is used for the template in an 8 µl PCR mixture containing 1.25 µl buffer, 300 µM deoxynucleotides, 1 pmol primer, 0.25 units Taq polymerase. Samples are denatured for 5 min at 94° C. and incubated for 35 cycles of the following: 94° C.×30s, 55° C.×30s, 72° C.×30s. After amplification and addition of stop solution, products are denatured for 3 minutes at 94° C. and electrophoresed on 6% polyacrylamide-5% glycerol gels at 25W for 3 hours. Gels are stained with silver nitrate as described by Bassam et al., [Anal. Biochem., 196:80–83 (1991)]. Differences are confirmed by direct DNA sequencing.

A comparative analysis of two clinical isolates by SSCP is shown in FIG. 12. Each isolate is studied in five lanes. A control lysis prone pneumococcus is shown in lanes 1–5. F79, a tolerant isolate is shown in lanes 6–10. Note the difference in the pattern in lanes 1 versus 6 and lanes 2 versus 7. These two differences indicate two changes in the sequence of the gene analyzed (HK) in the F79 isolate compared to the control. This pattern therefore identifies a clone of one type of tolerance mutation. Such testing and identification is important to the epidemiological study of the spread of resistance traits.

EXAMPLE 12

VANCOMYCIN TOLERANCE IN *STREPTOCOCCUS PNEUMONIAE*: A DEATH SIGNAL PEPTIDE REGULATED BY A TWO COMPONENT SYSTEM

Introduction

Regulation of autolysin activity is believed to occur on the post-translational level. For example, the expression of most hydrolases is constitutive throughout the cell cycle [Hakenbeck and Messer, Eur. J. Biochem. 129:1239–1244 (1977); Ronda et al., Antimicrob. Agents Chemother, 38:2311–2116 (1994)]. Expression of the pneumococcal autolysin gene from a plasmid in an autolysin deficient strain not only leads to the expected rapid lysis at the end of the exponential phase, but also autolysin activity during exponential phase is curtailed like the wild type [Ronda et al., Antimicrob. Agents Chemother, 38:2311–2116 (1994)]. This indicates regulation of autolysin independent of transcription of the autolysin itself. In addition, murein hydrolases are continuously present on the cell surface and since triggering of wall hydrolysis does not require the synthesis of new enzyme [Kitano and Tomasz, Antimicrob. Agents Chemother, 16:838–848], these surface located enzymes are always potentially capable of hydrolytic activity. Possible post-translational regulatory mechanisms include control at the site of transport [Tuomanen and Tomasz, Scand. J. Infect. Dis. Suppl., 74:102–112 (1990)], specific activation of the enzyme by substrate modification [Goodell and Tomasz, J. Bacteriol, 144:1009–1016 (1980)], or activation-inhibition by cofactors.

A striking example of physiological down regulation of autolysis occurs during amino acid deprivation, which instigates the stringent response [Cashel et al., In "Escherichia coli and Salmonella: cellular and molecular biology, Neidhardt et al., eds., Washington, D.C.: ASM Press (1996)]. Starved bacteria bind antibiotic normally, but do not lyse and do not rapidly die. Upon starvation, bacteria rapidly accumulate guanosine 3', 5'-bispyrophosphate (ppGpp), which is synthezised by ppGpp synthetase I, a ribosome associated enzyme encoded by the relA gene [Metzger et al., *J. Biol. Chem.*, 263:15699–15704 (1988); Schreiber et al., *J. Biol. Chem.*, 266:3760–3767 (1991); Svitil et al., *J. Biol. Chem.*, 268:2307–2311 (1993)]. ppGpp in turn shuts down the synthesis of phospholipids [Sokawa et al., *Biochem. Biophys. Res. Commun.*, 33:108–112 (1968)1 and cell wall peptidoglycan [Ishiguro and Ramey, *J. Bacteriol.*, 127: 1119–1126 (1976)]. In this setting antibiotic-induced lysis is blocked by an as yet uncharacterized defect in autolysin activation.

This protection from lysis, termed phenotypic tolerance, is a capability of all bacteria and is an important source of residual bacteria despite antibiotic therapy of infections in vivo. Tolerance is of major clinical significance since it has been shown that the inability to eradicate tolerant bacteria leads to failure of antibiotic therapy and acquisition of resistance [Handwerger and Tomasz, *Revs. Infect. Dis.*, 7:368–386 (1985); Tuomanen et al., *Antimicrob. Agents Chemother*, 30:521–527 (1986); Tuomanen et al., *J. Bacteriol*, 170:1373–1376 (1988A); Tuomanen et al., *J. Infect. Dis.*, 158:36–43 (1988B)]. Studies have shown that the prevalence of antibiotic tolerance among clinical isolates of pneumococci reaches up to 20% [Tuomanen et al., *Antimicrob. Agents Chemother*, 30:521–527 (1986)]. In contrast to the described phenotypic tolerance genetic changes causing antibiotic tolerance are also known. The most simple example of tolerance is the knockout of the autolysin gene, lytA [Tomasz et al., *Nature*, 227:138–140 (1970)]. For reasons that are not clear, no clinical isolates have been found because of a deletion in the autolysin. Rather, clinical tolerance at the level of regulation of autolysin activity [Tuomanen et al., *J. Bacteriol*, 170:1373–1376 (1988A); Tuomanen et al., *J. Infect. Dis.*, 158:36–43 (1988B)].

Methods

Strains of pneumococci and growth conditions: *S. pneumoniae* strain R6 [Tiraby and Fox, *Proc. Natl. Acad. Sci. U.S.A.*, 70:3541–3545 (1973)] was obtained from the Rockefeller University collection. The autolysin deficient strain, Lyt-4-4 was provided from the collection of Dr A. Tomasz, Rockefeller University. This strain is a stable point mutant created by chemical mutagenesis. *S. pneumoniae* was cultured on tryptic soy agar (TSA, Difco, Detroit, Mich., USA) supplemented with sheep blood 3% (v/v). For growth in liquid culture, the bacteria were grown at 37° C. without aeration in 5% $CO_2$ using a semi-synthetic casein hydrolysate medium supplemented with yeast extract (C+Y medium), [Lacks and Hotchkiss, *Biochem. Biophys. Acta.*, 39:508–517 (1960)]. For the selection and maintenance of pneumococci containing chromosomally integrated plasmids, bacteria were grown in the presence of 1 $\mu$g/ml erythromycin (Sigma, St. Louis, Mo., USA).

Recombinant DNA methods: DNA ligations, restriction endonuclease digestions, agarose gel electrophoresis and DNA amplification by PCR were performed according to standard techniques [Sambrook et al., "*Molecular Cloning. A laboratory manual*", second ed., Cold Spring Harbor Laboratory, Coldspring Harbor, N.Y. (1990)]. DNA purification and plasmid preparations were performed using kits from Qiagen (Qiagen, S. Clarita, Calif., USA) and Promega/Wizard (Promega, Madison, Wis., USA) according to the manufacturer's instructions. Transformation of *E. coli* with plasmid DNA was carried out with $CaCl_2$-treated cells as described previously [Brown et al., *FEMS Microbiol. Lett.*, 5:219–222 (1979)]. Transformation of *S. pneumoniae* was performed according to standard protocols [Pearce et al., *Mol. Microbiol.*, 9:1037–1050 (1993)].

Insertional inactivation of vexp1 and vexp3: To create the knockout mutants the method of insertional duplication mutagenesis, which is a homology-directed insertion of foreign DNA was used [Haldenwang et al., *J. Bacteriol*, 142:90–98 (1980); Mejean et al., *Gene*, 15:289–293 (1981)]. For insertional duplication mutagenesis of vexp1 an internal 435 bp fragment (bp 473–908) was amplified using total DNA of R6 and evexp1 (5'-ACG AAG AAT TCG CTA AGA AGA ACG GT-3' SEQ ID NO:49) and bvexp2 (5'-ATT AAG GAT CCA GCT ATC AA-3' SEQ ID NO:50) as primers. The PCR product was digested with BamHI and EcoRI. An identical strategy was used to knockout the other genes. The insertional inactivation of vexp3 was performed using the primers evexp3 (5'-ATC AAG GGA TCCACT GCC AAG GC-3' SEQ ID NO:51) and bvexp3 (5'-AGA GGA GAA TTCCCA CTT CCT TGC G-3' SEQ ID NO:52). The resulting fragment was 900-bp long (bp 106–906). The amplified fragments were ligated to pJDC9 and digested with BamHI and EcoRI [Chen and Morrison, *Gene*, 55:179–187 (1987)]. The resulting recombinant plasmids were then transformed into R6. Mutations were confirmed by Southern blot analysis.

Penicillin and vancomycin susceptibility and autolysis rates: Autolysis rates of the strains were determined using 10 ml cultures of *S. pneumoniae* exposed to ten times the minimal inhibition concentration (MIC) of benzylpenicillin (0.1 mg/nm) when the $OD_{620nm}$ reached 0.25 to 0.3. Autolysis rates were calculated as the first order rate constant $K = \ln(A_0/A_{120}) \times \min^{-1}$, where $A_0$ represents the peak of absorbance reading at 620 nm and $A_{120}$ the reading after a further 120 min of incubation [Liu and Tomasz, *J. Infect. Dis.*, 152:365–72 (1985)]. The effect of penicillin and vancomycin treatment on the viability was determined by exposing 10 ml cultures in the early exponential phase of growth ($OD_{620 nm} = 0.3$, corresponding $5 \times 10^7$ cfu/ml) to ten times the MIC of benzylpenicillin or vancomycin, respectively. After various times of exposure, 100 $\mu$l portions were removed, serially diluted in C+Y and in the case of penicillin supplemented with 100 units of penicillinase (Sigma), and plated on tryptic-soy agar supplemented with 3% sheep blood (v/v).

Subcellular fractionation: Pneumococci were separated in subcellular fractions by a modification of a previously described method [Hakenbeck et al., *Antimicrob. Agents Chernother.*, 30:553–558 (1986)]. Briefly, bacteria were grown in 10 ml of C+Y medium to an $OD_{620 nm}$ of 0.9, and isolated by centrifugation 17,000×g for 10 min. The supernatant was harvested and stored at −70° C. Cell pellets were resuspended in 250 $\mu$l of TEP (25 mM Tris-HCl pH 8.0, 1 mM EDTA, 1 mM phenyl methyl sulphonyl fluoride). The suspension was sonicated for a total of 4 min with 15 second bursts. Cellular debris was removed by centrifugation at 17,000×g for 10 min. The bacterial membranes and the cytoplasmic contents were separated by centrifugation at 98,000×g for 4 hours. The supernatant from this final step contained the cytoplasmic fraction while the pellet contained the bacterial membranes. Samples from each fraction were evaluated for protein content and solubilized in SDS sample buffer for subsequent gel electrophoresis.

Peptide synthesis: Edman degradation was performed with a Perkin-Elmer Applied Biosystems 433A automatic sequencer. The synthetic peptide was prepared by the Center for Biotechnology at St. Jude Children's Research Hospital. The supplier reported that analysis by HPLC showed the peptide was 90% pure and that mass spectrographic analysis demonstrated the predicted mass for the peptide.

Immunoblotting: The peptide P27 was analyzed by running precasted 16.5% Tris-Tricine gels (BioRad, CA) and by Western blotting using Immobilon-P membranes (Millipore Corporation, Bedford, Mass.). The membranes were incubated with polyclonal rabbit anti-P27 antibody (1:2000). The membranes were developed using goat anti-rabbit horseradish peroxidase (ECL Chemiluminescence leit, Amersham, Buckinghamshire, England).

Northern blot: Total RNA was prepared according to the manufacturer's instructions (Qiagen). Approximately 10 to 20 µg of total RNA was separated in a 1.2% formaldehyde gel. The gel was rinsed in 20×SSC buffer and RNA was transferred to nylon membranes (Hybond-N-, Amersham) by capillary blotting [Sambrook et al., "*Molecular Cloning. A laboratory manual*", second ed., Cold Spring Harbor Laboratory, Coldspring Habor, N.Y. (1990)]. A 435-bp PCR fragment generated by primers evexp1 and bvexp1 was used as the vexp1-specific probe. A 900-bp PCR fragment generated by primers evexp3 and bvexp3 was used as the vexp3-specific probe. The 261-bp specific probe for p28 (which encodes P27) was created by the primers ep28 and bp28. A 371-bp PCR fragment generated by the primers evncR and bvncR was used as the vncS-specific probe. A 411-bp PCR fragment generated by the primers evncS and bvncS was used as the vncR-specific probe. The probes were labeled with $\alpha^{32}P[dCTP]$ (Amersham). Hybridization under stringent conditions was performed according to standard protocols.

Computer-assisted sequence analysis: Sequence analysis and alignments were conducted with the program DNA-Star and with Genetics Computer Group sequence analysis software package. The computer program BLAST [Altschul et al., *J. Mol. Biol.*, 215:403–410 (1990)] was used to search for amino acid sequences that were homologous to the gene products of vexp1, vexp2, vexp3, p28, vncR and vncS.

Results

To detect genes that are part of the trigger pathway of the pneumococcal autolysin a library of loss of function mutants has been created, which was screened for antibiotic tolerance [Pearce et al., *Mol. Microbiol.*, 9:1037–1050 (1993)]. The screen identified 17 mutants, which had an active autolysin, but failed to die in the presence of penicillin. One mutant, SPSJ01, also failed to die in the presence of vancomycin, a further analysis of the affected genes revealed a two component regulatory system, VncS-VncR, controlling the activity of autolysin. It is reasonable to assume that this two component system represents the start of the pneumococcal autolytic trigger pathway, functioning as a relay station reacting to cell density signals or the binding of antibiotics to penicillin binding proteins. Similar to the enterococcal histidine kinase $VanS_B$, the pneumococcal VncS works most likely as a kinase/phosphatase (see Example 1, above).

The further analysis of the gene locus encoding the two component system VncS-VncR putative genes involved in the trigger pathway of autolysin revealed a two component regulatory system VncR-VncS, which regulates the expression of a peptide, P27, which itself is exported by an ABC-transporter. Expression of the peptide is induced at late logarithmic phase and it mediates growth inhibition in other pneumococci.

Organization and regulation of the gene locus: Using Analysis of the gene cluster upstream of the two component system, VncS-VncR, revealed a 84-bp large open reading frame p28 encoding a small signal peptide, P27 and three genes encoding a putative ABC (ATP-binding cassette) transporter Vexp (FIG. 13) [Higgins, Annu Rev Cell Biol, 8:67–113 (1992); Linton and Higgins, *Mol. Microbiol.*, 28:5–13 (1998)]. Vexp has a fused ABC-ABC organization with heterodimeric transmembrane domains (TMDs). The genes vexp1 and vexp3 encode putative hydrophobic transmembrane proteins consisting of four TMDs. vexp1 and vexp3 flank the gene vexp2 which encodes an ATP-binding cassette (ABC) protein including the Walker A motif $GX_4GK(S/T)$ [Walker et al., *EMBO J*, 1:945–951 (1982)] at amino acid positions 41 to 46, and the Walker B motif $(R/K)X_{6-8}hyd_4D$ (hyd, hydrophobic residues) [Ames et al., *FEMS Microbiol Rev*, 6:429–446 (1990); Hyde et al., *Nature*, 346:362–5 (1990)], at amino acid positions 142 to 156. An ABC signature sequence (L/Y)SGG(Q/M) [C. F. Higgins, Annu Rev Cell Biol, 8:67–113 (1992)], at positions 130 to 134, possibly functions as a peptide linker joining different domains of the protein. The fourth motif is a conserved histidine located 34 amino acids downstream of the aspartic acid of the Walker B motif, preceded by 4 hydrophobic residues and followed by a charged residue. ABC proteins often, but not exclusively, generate the energy of multi-component membrane bound transporters. They mediate the transport of a diversity of substrates, including ions, sugars and peptides [Alloing et al., *J. Mol. Biol.*, 241:44–58 (1994); Jenkinson et al., *J. Bacteriol*, 178:68–77 (1996); Russell et al., *J. Biol. Chem*, 267:4631–4637 (1992)]. The majority of ABC transporters are associated with periplasmic-binding proteins which provide the primary substrate binding site for uptake of solute into cells [Linton and Higgins, *Mol. Microbiol.*, 28:5–13 (1998)]. The absence of such a protein in the putative Vexp ABC transporter indicates that it is expected to be involved in substrate export.

Northern blot analysis using a 435-bp probe specific for vexp1, revealed a single transcript of 2-kb indicating that vexp1 and vexp2 are transcribed from one promoter located upstream of vexp1 (see Example 5, above). Using a 900-bp probe specific for vexp3, a 1.7-kb large transcript, which does not match the size of the 1.38-kb open reading frame vexp3, was obtained. To confirm the assumption that the open reading frame p28 downstream of vexp3 was cotranscribed from a promoter upstream of vexp3, a probe specific for the intergenic region between vexp3 and vncR was used. The 1.7-kb transcript matched exactly the size of the transcript obtained with the probe specific for vexp3. Two putative stem loop structures directly downstream of p28 indicated termination of transcription.

Genes involved in export of peptides are usually found adjacent to the structural gene and are under the same regulation [Kolter and Moreno, *Annu. Rev. Microbiol.*, 46:141–165 (1992)]. The close vicinity of the two component system VncR/S to the ABC transporter and the gene encoding P27 suggested a regulation of this locus by the two component system In addition, VncR/S is responsible for repression and release of the autolytic trigger pathway. One of the stimuli sensed by the sensor histidine kinase VncS is most likely that of an unknown cell density signal.

To investigate if the response regulator VncR and P27 are indeed both regulated in a cell density dependent manner, the wild type strain R6 was harvested at different growth stages. Northern blot analysis demonstrated that cells harvested from the early- and mid-exponential growth stage, showed almost no transcription of vncR, whereas bacteria obtained from stationary growth stage demonstrated a clearly increased transcription of vncR. Similar to these findings the level of transcription of p28 increased during stationary phase. The loss of function mutant vncR demonstrated a constitutive level of transcription of the p28 gene, and an upregulation of the p28 gene was not observed during stationary phase. This finding establishes a direct link between the response regulator VncR and regulation of the p28 gene.

Triggering of different death pathways by VncS: Mutations of the HK (vncS) have been shown to lead to loss of killing by penicillin, vancomycin and a variety of other antibiotics. This tolerance phenotype indicates that VncR/S may participate in the triggering pathway for the major pneumococcal autolysin, LytA. A model was proposed, which delineates VncS as a kinase/phosphatase controlling the level of phosphorylation of the response regulator VncR. A dephosphorylated VncR could enable triggering of LytA, e.g. during stationary phase or due to triggering by antibiotics. To address the question if the kinase/phosphatase VncS was indeed directly linked to the major pneumococcal autolytic pathway, VncS was overexpressed from a plasmid in a vncS deficient knockout mutant. For that purpose the vncS mutant was transformed with a construct where vncS was placed downstream of the inducible promoter of comA and ligated in the vector pMU1328 [Achen et al., *Gene*, 45:45–49 (1986)], creating the strain RNET01. Induction of transcription with the competence stimulating peptide (CSP) leads to an approximately 40-fold increase in transcription. After addition of 10 µg/ml of CSP to RNET01, the strain grew in long chains with up to 200 pneumococci. This morphological feature was remarkable, since neither a knockout in the major autolysin LytA, nor in the newly discovered glucosaminidase, LytB [Garcia et al., *Mol. Microbiol.*, 31:1275–1277 (1999)], led to a major impact on daughter cell separation. However, an introduction of the lytB mutation into the amidase-deficient, lytA, led to a similar extent of chain formation compared to that observed in the RNET01 strain after induction of vncS transcription. These data provide evidence that the histidine/phosphatase VncS is likely to regulate in addition to the LytA specific pathway, other not yet defined death pathways, such as the LytB pathway.

P27, an exopeptide induces growth inhibition and cell death: The gene locus Vexp-VncR/S includes an 84-bp open reading frame, p28. Northern blot analysis showed that this open reading frame is co transcribed with vexp3, suggesting that p28 encodes a potential peptide with a predicted size of about 3 kDa. To further address the question whether transcription of p28 leads to a translational product, the peptide was synthesized and used to raise specific antibodies. Western blot analysis of the cytoplasmic fraction and the supernatant of the parent strain R6 demonstrated a 3 kDa product reactive with the P27 specific antiserum (FIG. 14). Analysis of the insertion duplication mutagenesis of vexp3, which is polar on the downstream p28 gene, resulted in no detection of any reactive species in either the cytoplasm or the supernatant (FIG. 14). Western blot analysis of the mutant defective in the first putative transmembrane protein, vexpl, showed no P27 in the supernatant (FIG. 14). This finding and the missing periplasmic binding protein in the organization of the ABC-transporter, VexP, as well as lack of a signal sequence of P27 is indicative that Vexp transports P27 outside the bacterial cell. The described co-transcription of the transmembrane protein vexp3 with the open reading frame encoding the peptide vexP27, is consistent with this conclusion, since genes that are involved in modification and export of peptides are often found adjacent to the structural gene and are under the same regulation [Kolter and Moreno, *Annu. Rev. Microbiol.*, 46:141–165 (1992)].

To determine the biological effect of P27, cultures of the parent strain R6 at an $OD_{620\ nm}$ of 0.1 were exposed to 0.1 mmol of the synthetic peptide homolog P27. The peptide's effect on turbidity and viability is shown in FIGS. 15A–15C. Addition of P27 induced a potent growth inhibition in the parent strain R6 and resulted in a loss of viability of 2 log units. Titration experiments using concentrations of P27 ranging from 50 nmol to 0.2 mmol demonstrated that the extent of growth inhibition was dose dependent (FIG. 15C). This behavior is distinct from all other antibiotics described to date, which have a clear cut MIC. At a concentration of 50 nmol the inhibition of growth was marginal, whereas the addition of 0.2 mmol of synthetic peptide resulted in complete growth arrest. At concentrations greater than 0.05 mmol a substantial loss of viability was demonstrated for R6.

To ensure the specificity of the biological effect mediated by peptide P27, different peptide structure variants were analyzed. Using two truncated forms of the peptide lacking 14 amino acids from the C-terminus or 14 amino acids from the N-terminal region abolished its biological activity completely. A truncated form lacking the 5 C-terminal also reduced its efficiency (FIG. 16).

P27 is capable of triggering different autolytic pathways: To identify the relationship between P27 and the activation of the autolysin LytA, the bactericidal effect of the peptide on the pneumococcal mutant Lyt-4-4 (which is deficient in the major autolysin), was investigated. The mutant Lyt-4-4 was still killed by P27 but not as efficiently as R6 (FIG. 17), suggesting that cell death induced by P27 is not entirely dependent on an intact LytA. Furthermore, these data provide further evidence that in addition to the major pneumococcal executioner, LytA, alternative death pathways exist, which can be activated by P27. Compared to the diplococcal morphology of wild type pneumococci, pneumococci lacking an active autolysin grow in long chains. Addition of the peptide to the mutant Lyt-4-4 resulted in reversion of the chains to diplococci also indicating dominance of the peptide for the phenotype of cell separation and that the activity of the peptide can override a loss in autolysin activity.

To investigate if the peptide P27 was not only capable of triggering different death pathways but was in fact, obligatory, a mutant deficient in P27 was investigated for antibiotic tolerance. Insertion duplication mutagenesis of vexp3 was performed which resulted in a mutant deficient in P27 production due to the polar effect. This was confirmed by Western blot analysis. After addition of 10× MIC of vancomycin, the vexp3 mutant underwent less than 2 log kill in 4 hours in contrast to 4 log kill of the wild type (FIG. 18A). Analogous to the vncS mutant, tolerance for the vexp3 mutant extended to penicillin and cephalosporins suggesting that the peptide, P27, might be indeed required for the initiation of pneumococcal death pathways. To exclude the possibility that tolerance of the vexp3 mutant resulted from changes in either the expression or intrinsic activity of the autolysin LytA, Western blot analysis of LytA of the vexp3 mutant was performed. The blot showed in addition to the expected 36 kDa band, an additional 54 kDa larger band (FIG. 18B). However, exogenous autolysin from vexp3 mutant was as efficient as that from wild type pneumococcus at reconstitution of lysis of the autolysin deficient strain Lyt-4-4 (FIG. 18C).

Exposing the vncS mutant to the P27 peptide did not result in growth inhibition or even cell death. To investigate if this phenomenon was restricted to mutations in VncS or rather to the antibiotic tolerant phenotype, clinical pneumococcal isolates, which had no defect in the histidine-kinase VncS (verified by sequencing), were exposed to 0.1 mmol of P27. Although the isolates showed growth inhibition to a different extent, in all samples tested a clear reduction in growth could be observed. This supports the conclusion that VncS might function as a receptor for P27.

P27 and the stringent response mechanism: The stringent response is believed to prevent the death pathway. To clarify the relationship of the stringent response to P27 activity, protein synthesis of R6 was inhibited by leucine deprivation and the effect of P27 was monitored (FIG. 19). Under these conditions, neither the addition of 10× the MIC of penicillin or vancomycin nor the addition of 0.2 mmol P27 resulted in lysis of R6. However, a combination of a cell wall synthesis-inhibiting antibiotic, e.g., penicillin with P27 resulted in significant lysis of the cells. The minimum concentration of penicillin required to cause penicillin dependent autolysis was equal to its MIC (0.1 mg/ml). This suggests that the stringent response interrupts two steps in the autolytic pathway, one circumvented by antibiotics and the other one by exogenous P27.

Discussion

The phenomenon that suppression of the autolytic system in bacteria leads to antibiotic tolerance suggested the framework for the mechanism of action of penicillin 30 years ago [Tomasz et al., Nature, 227:138–140 (1970)]. Members of this regulatory circuit, a universal feature of bacteria, have not been as yet found. Antibiotic tolerance is of clinical significance, as it has been shown that the inability to eradicate tolerant bacteria leads to failure of therapy [Entenza et al., J. Infect. Dis., 175:70–76 (1997); Handwerger and Tomasz, Revs. Infect. Dis., 7:368–386 (1985); Meeson et al., J. Antimicrob. Chemother., 25:103–109 (1990); Novak et al, Nature (1999); Tuomanen et al., J. Bacteriol, 170:1373–1376 (1988A); Tuomanen et al., J. Infect. Dis., 158:36–43 (1988)]. Furthermore, tolerance is considered to promote the development of antibiotic resistance and in a time of dramatically increasing antibiotic resistance, the need to uncover the trigger pathway of autolysins has become more urgent. Although the distinctive mechanisms mediating antibiotic resistance have been studied extensively, the link between binding of antibiotics to their bacterial target and the consequent activation of the trigger pathway regulating the activity of autolysins remains completely obscure.

The present results demonstrate that in S. pneumoniae, the two component regulatory system, VncR/S is part of a signal transduction pathway most likely triggering different autolytic pathways. Overexpression of the histidine/kinase VncS led to an almost complete block of daughter cell separation, identical to an effect observed in a double knockout of the autolysins LytA and LytB. Furthermore, it could be demonstrated that VncR/S upregulates the transcription of a 27 amino acid peptide, P27 (SEQ ID NO:44), which presumably functions as a death effector. The peptide is cotranscribed with a putative transmembrane protein, which is part of an ABC-transporter, Vexp, that exports P27. This complex is located directly upstream of the two component system, VncR/S. Although the peptide is constitutively expressed at a low level, transcription is unregulated during late logarithmic stage when pneumococci are known to undergo spontaneous autolysis. This quorum sensing paradigm is consistent with a similar set of transporter, peptide and two component system that controls competence [Havarstein et al., Mol. Microbiol., 21:263–869 (1996); Pestova et al., Mol. Microbiol., 9:1037–1050 (1996)]. Sensing the peptide P27 by other pneumococci leads to initial growth inhibition and later on to cell death. These effects occur in part independently of the autolytic trigger pathway LytA, since the LytA defective strain, Lyt-4-4, experiences a similar biological effect, though to a lesser extent. Another important feature of the P27 peptide is illustrated by its interaction with the stringent response, the most powerful regulation of autolysis known in bacteria. A combination of a cell wall synthesis inhibiting antibiotic with the peptide relaxes the stringent response. An effect which has otherwise only been described for chloramphenicol [Kusser and Ishiguro, J. Bacteriol, 164:861–865 (1985)].

A key element of the biology of the peptide P27 is its integration into the signal transduction pathway initiated by the two component regulatory system VncR/S. During logarithmic phase, the autolytic systems are repressed by a stimulus, which promotes the phosphorylation activity of the histidine kinase. Release of this stimulus is considered to be cell density-dependent and most likely leads to a dephosphorylation of the response regulator VncR. It is reasonable to assume that the observed upregulation of transcription during late logarithmic stage of vexp3 and the cotranscribed p28, is due to the same signal. This assumption is supported by the observation that a mutant deficient in VncR demonstrates low level transcription and no clear upregulation of vexp3-p28 during late logarithmic stage.

The concurrence of cell death and lysis upon exposure to antibiotics targeting cell wall synthesis indicates that many bacteria, including pneumococci, are killed by triggering their major autolytic enzymes. However, it is known that in some bacteria killing occurs without accompanying autolysis [Handwerger and Tomasz, Revs. Infect. Dis., 7:368–386 (1985); Horne and Tomasz, Antimicrob. Agents Chemother, 11:888–896 (1977); McDowell and Lemanski, J. Bacteriol, 170:1783–1788 (1988)], suggesting that mechanisms other than cell lysis exist in bacteria for the killing effect of penicillin. It has long been assumed that penicillin and other such cell wall inhibitors act in pneumococcus through the triggering of the major autolytic amidase, LytA. Different findings suggest that only part of this killing is due to cell lysis by the aridase, indicating that other death pathways in S. pneumoniae exist. Exposing pneumococci to cyclic antibiotic pressures revealed mutants with a mutation in the uncharacterized cid gene, which were able to resist both lysis and killing induced by penicillin [Moreillon et al., Antimicrob. Agents Chemothe., 34:33–39 (1990); Moreillon and Tomasz, J. Infect. Dis., 157:1150–1157 (1988)], although they contained normal autolytic amidase and cell walls normally susceptible to digestion by amidase. These findings led to the conclusion that pneumococci have two different targets for penicillin: an autolysis-dependent and autolysis-independent killing mechanism [Moreillon et al., Antimicrob. Agents Chemothe., 34:33–39 (1990)]. However, even though the cid gene and the lytA gene are not related, triggering of the amidase activity in situ in growing bacteria was significantly reduced in Lyt$^+$Cid$^-$ cells, indicating that there ought to be a regulatory interaction between the cid gene and the amidase.

As disclosed herein several findings indicate that P27 functions as a signal capable (or perhaps even required) for the triggering of different death pathways in S. pneumoniae. First, P27 is able to stop growth and induce cell death in the LytA deficient, Cid positive strain, Lyt-4-4. Second, P27 potentiates the bactericidal effect of penicillin in antibiotic sensitive and LytA deficient bacteria. Third, although P27 is not sufficient in promoting cell death in starved bacteria alone, it is able to induce cell death in combination with an antibiotic such as penicillin.

A further indication of the involvement of P27 in pneumococcal cell death is the concurrence of the cell density-dependent upregulation of P27 and the suicidal activity during stationary phase. In addition, overexpression of the HK(VncS) in a non-tolerant background led to the induction of antibiotic tolerance, and to a complete lack of daughter cell separation. This indicates that VncS regulates at least one additional death pathway in pneumococcus. An assumption, which is supported by a recent publication demonstrating that a double knockout in LytA and LytB, a newly discovered pneumococcal murein hydrolase, leads to an almost complete block of cell separation [Garcia et al., *Mol. Microbiol.*, 31:1275–1277 (1999)]. Although a LytB deficient mutant did not lead to an antibiotic tolerant phenotype, its proposed function as a glucoaminidase [Garcia et al., *Mol. Microbiol.*, 31:1275–1277 (1999)] suggests a role in cell division and autolysis.

Bacteria and fungi sometimes use cationic peptides like lantibiotics and bacteriocins as selective antibiotics [Kolter and Moreno, *Annu. Rev. Microbiol.*, 46:141–165 (1992)]. The mode of action of cationic peptides is not receptor mediated, but rather self-promoted [Gough et al., *Infect. Immun.*, 64:4922–4927 (1996); Piers et al., *Antimicrob. Agents Chemother*, 38:2311–2116 (1994)]. Cationic peptides have two distinguishing features. They have a net positive charge at neutral pH of at least +2 by virtue of their content of the basic amino acids, arginine and lysine, and a distinct three dimensional structure [R.E.W. Hancock, *Lancet*, 349:418–422 (1997)]. Despite the fact that the peptide P27 has a net charge of +4 at neutral pH, and an alpha helical structure, it also has properties that are different from the members of this group. For example, the peptide P27 had no MIC normally observed in cationic peptides, but rather demonstrated a dose dependent inhibitory effect on growth. The mode of action and selectivity of cationic peptides is determined by their interaction with bacterial cell membranes. This implies a relatively wide range of activity and a non-receptor mediated effect. However, P27 does not inhibit growth of the histidine/phosphatase vncS mutant suggesting VncS might act as a receptor.

Taken together, the data in the present study provide important evidence that the two component system VncR/S is the beginning of a signal transduction pathway involved in regulating different death pathways in *S. pneumoniae*. One of the death effectors seems to be a peptide encoded by the open reading frame between vex3 and vncR (see FIG. 13) which is also regulated by the two component system VncS/R. As shown in the above Example, P27 is one such peptide. In a quorum sensing dependent manner, transcription of P27 appears to be activated.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all base sizes or amino acid sizes, and all molecular weight or molecular mass values, given for nucleic acids or polypeptides are approximate, and are provided for description. Various publications are cited herein, the disclosures of which are incorporated by reference in their entireties.

What is claimed is:

1. A method of identifying an agent that is capable of inhibiting the growth of or killing a bacterial cell comprising:

(a) contacting the agent with a bacterial cell, wherein the bacterial cell has been selected to have a defective His-Asp phosphorelay pathway; and (b) determining whether the cell is killed or its growth is inhibited; wherein an agent is identified as capable of killing or inhibiting the growth of a bacterial cell if it kills or inhibits the growth of the bacterial cell.

2. The method of claim 1 wherein the bacterial cell is a vancomycin tolerant cell.

3. The method of claim 2 wherein the His-Asp phosphorelay pathway lacks a functional sensor histidine kinase having a wild type amino acid sequence of SEQ ID NO:14.

4. The method of claim 3 wherein the bacterial cell is not killed by a peptide having the amino acid sequence of SEQ ID NO:2.

5. The method of claim 2 wherein the His-Asp phosphorelay pathway lacks a functional response regulator having a wild type amino acid sequence of SEQ ID NO:16.

6. The method of claim 5 wherein the bacterial cell is not killed by a peptide having the amino acid sequence of SEQ ID NO:2.

7. The method of claim 1 wherein the bacterial cell is not killed by a peptide having the amino acid sequence of SEQ ID NO:2.

8. The method of claim 1 wherein the bacterial cell is a pneumococcal cell.

* * * * *

SEQUENCE LISTING

<160> NUMBER OF SEQ ID NOS: 76

<210> SEQ ID NO 1
<211> LENGTH: 75
<212> TYPE: DNA
<213> ORGANISM: Streptococcus pneumoniae

<400> SEQUENCE: 1

```
atgagaaagg aatttcacaa cgttttatct agtggtcagt tgcttgcaga caaaaggcca  60
gcaagagact ataat                                                    75
```

<210> SEQ ID NO 2
<211> LENGTH: 25
<212> TYPE: PRT
<213> ORGANISM: Streptococcus pneumoniae

<400> SEQUENCE: 2

```
Met Arg Lys Glu Phe His Asn Val Leu Ser Ser Gly Gln Leu Leu Ala
  1               5                  10                  15
Asp Lys Arg Pro Ala Arg Asp Tyr Asn
            20                  25
```

<210> SEQ ID NO 3
<211> LENGTH: 75
<212> TYPE: DNA
<213> ORGANISM: Artificial Sequence
<220> FEATURE:
<223> OTHER INFORMATION: Description of Artificial Sequence: Encodes modified Streptococcus Pneumonia peptide -continued

```
<400> SEQUENCE: 3
atgagaaagg aatttcacaa cgttttatct gctggtcagt tgcttgcaga caaaggcca  60
     gcaagagact ataat                                                  75

<210> SEQ ID NO 4
<211> LENGTH: 25
<212> TYPE: PRT
<213> ORGANISM: Artificial Sequence
<220> FEATURE:
<223> OTHER INFORMATION: Description of Artificial Sequence: Modified
      Streptococcus Pneumonia peptide

<400> SEQUENCE: 4

Met Arg Lys Glu Phe His Asn Val Leu Ser Ala Gly Gln Leu Leu Ala
      1               5                  10                  15
     Asp Lys Arg Pro Ala Arg Asp Tyr Asn
                 20                  25

<210> SEQ ID NO 5
<211> LENGTH: 75
<212> TYPE: DNA
<213> ORGANISM: Artificial Sequence
<220> FEATURE:
<223> OTHER INFORMATION: Description of Artificial Sequence: Encodes
      modified Streptococcus Pneumonia peptide

<400> SEQUENCE: 5
atgagaaagg aatttcacaa cgttttatct agtggtcagt tgcttgcaga caaaggcca  60
     gcaagagacg ctaat                                                  75

<210> SEQ ID NO 6
<211> LENGTH: 25
<212> TYPE: PRT
<213> ORGANISM: Artificial Sequence
<220> FEATURE:
<223> OTHER INFORMATION: Description of Artificial Sequence: Modified
      Streptococcus Pneumonia peptide

<400> SEQUENCE: 6

Met Arg Lys Glu Phe His Asn Val Leu Ser Ser Gly Gln Leu Leu Ala
      1               5                  10                  15
     Asp Lys Arg Pro Ala Arg Asp Ala Asn
                 20                  25

<210> SEQ ID NO 7
<211> LENGTH: 42
<212> TYPE: DNA
<213> ORGANISM: Streptococcus pneumoniae

<400> SEQUENCE: 7
atgagaaagg aatttcacaa cgttttatct agtggtcagt tg                    42

<210> SEQ ID NO 8
<211> LENGTH: 14
<212> TYPE: PRT
<213> ORGANISM: Streptococcus pneumoniae

<400> SEQUENCE: 8

Met Arg Lys Glu Phe His Asn Val Leu Ser Ser Gly Gln Leu
      1               5                  10

<210> SEQ ID NO 9
<211> LENGTH: 33
<212> TYPE: DNA
<213> ORGANISM: Streptococcus pneumoniae
```

-continued

<400> SEQUENCE: 9

```
cttgcagaca aaaggccagc aagagactat aat                                 33
```

<210> SEQ ID NO 10
<211> LENGTH: 11
<212> TYPE: PRT
<213> ORGANISM: Streptococcus pneumoniae

<400> SEQUENCE: 10

```
Leu Ala Asp Lys Arg Pro Ala Arg Asp Tyr Asn
 1               5                  10
```

<210> SEQ ID NO 11
<211> LENGTH: 84
<212> TYPE: DNA
<213> ORGANISM: Streptococcus pneumoniae

<400> SEQUENCE: 11

```
atggaattta tgagaaagga atttcacaac gttttatcta gtggtcagtt gcttgcagac   60
aaaaggccag caagagacta taat                                          84
```

<210> SEQ ID NO 12
<211> LENGTH: 28
<212> TYPE: PRT
<213> ORGANISM: Streptococcus pneumoniae

<400> SEQUENCE: 12

```
Met Glu Phe Met Arg Lys Glu Phe His Asn Val Leu Ser Ser Gly Gln
 1               5                  10                  15
Leu Leu Ala Asp Lys Arg Pro Ala Arg Asp Tyr Asn
                20                  25
```

<210> SEQ ID NO 13
<211> LENGTH: 1329
<212> TYPE: DNA
<213> ORGANISM: Streptococcus pneumoniae

<400> SEQUENCE: 13

```
atgaaacgaa caggtttatt tgcaaagata tttatctata ccttctcgat atttagtgtt   60
ctggttatct gccttcattt agctatttat tttcttttc cttcgactta tctgagtcat  120
cgtcaggaaa ccattggtca aaggcaaca gccattgccc agtccctaga agggaaagat  180
aggcagagta tcgagcaagt gttagacttg tattcccaga ctagtgtat caaggggacc  240
gtcaaaggtg agatgaccga ggacaagtta gaagtcaagg acagtcttcc tctggacaca  300
gaccgccaga caacctctct ctttattgag gagcgcgagg tgaaaacgca agacggtggt  360
actatgattc tccagttcct agcttccatg gatttacaaa aggaagcgga gcaaatcagt  420
ctccagtttc ttccctatac cttgctggcc tccttctga tttccctttt ggtggcctac  480
atctacgctc ggactattgt tgcaccgatt ttggaaatca agcgggtgac ccgtcggatg  540
atggacctgg attcccaagt gcgattgcgc gtggattcta aggatgagat aggtaatctc  600
aaggaacaaa tcaatagcct ctaccagcat ctcttgactg ttattgcgga cttgcatgaa  660
aagaatgaag ccattctcca gctggagaag atgaaggtcg aattcctacg aggagcttct  720
catgaattga aaacaccgct ggctagtttg aaaatcctaa tcgaaaatat gagagagaat  780
atcggtcgtt ataaggatag agaccagtat ctgggagttg ccttggggat tgtggatgaa  840
ctcaatcacc atgttctgca gatactttcc ctctcttctg tgcaggaatt gcgagatgat  900
agggaaacaa ttgacctcct ccagatgacg caaaatctgg tcaaagatta tgccttgcta  960
gccaaggaga gagctcca gatagacaat agtttgaccc atcagcaggc ttatctaaac 1020
ccatcagtta tgaagttgat tctttctaat ctcatcagca atgccattaa gcactctgtt 1080
ccaggtggct tagttcgaat tggagaaaga gaagagaac ttttatcga aatagctgt  1140
agctcagagg aacaagaaaa actagcccag tctttttctg acaatgccag tcgcaaggtc 1200
aaggggtctg gtatgggct ctttgtggtt aagagtctat tagaacatga aaaattagct 1260
tatcgtttcg agatggagga gaatagttta accttcttta tagatttttcc aaaagtcgtc 1320
caagactag                                                         1329
```

<210> SEQ ID NO 14
<211> LENGTH: 442
<212> TYPE: PRT
<213> ORGANISM: Streptococcus pneumoniae

```
<400> SEQUENCE: 14

Met Lys Arg Thr Gly Leu Phe Ala Lys Ile Phe Ile Tyr Thr Phe Ser
     1               5                  10                  15
    Ile Phe Ser Val Leu Val Ile Cys Leu His Leu Ala Ile Tyr Phe Leu
                    20                  25                  30
    Phe Pro Ser Thr Tyr Leu Ser His Arg Gln Glu Thr Ile Gly Gln Lys
                35                  40                  45
    Ala Thr Ala Ile Ala Gln Ser Leu Glu Gly Lys Asp Arg Gln Ser Ile
             50                  55                  60
    Glu Gln Val Leu Asp Leu Tyr Ser Gln Thr Ser Asp Ile Lys Gly Thr
     65                  70                  75                  80
    Val Lys Gly Glu Met Thr Glu Asp Lys Leu Glu Val Lys Asp Ser Leu
                    85                  90                  95
    Pro Leu Asp Thr Asp Arg Gln Thr Thr Ser Leu Phe Ile Glu Glu Arg
                100                 105                 110
    Glu Val Lys Thr Gln Asp Gly Gly Thr Met Ile Leu Gln Phe Leu Ala
                115                 120                 125
    Ser Met Asp Leu Gln Lys Glu Ala Glu Gln Ile Ser Leu Gln Phe Leu
    130                 135                 140
    Pro Tyr Thr Leu Leu Ala Ser Phe Leu Ile Ser Leu Leu Val Ala Tyr
    145                 150                 155                 160
    Ile Tyr Ala Arg Thr Ile Val Ala Pro Ile Leu Glu Ile Lys Arg Val
                    165                 170                 175
    Thr Arg Arg Met Met Asp Leu Asp Ser Gln Val Arg Leu Arg Val Asp
                    180                 185                 190
    Ser Lys Asp Glu Ile Gly Asn Leu Lys Glu Gln Ile Asn Ser Leu Tyr
                195                 200                 205
    Gln His Leu Leu Thr Val Ile Ala Asp Leu His Glu Lys Asn Glu Ala
    210                 215                 220
    Ile Leu Gln Leu Glu Lys Met Lys Val Glu Phe Leu Arg Gly Ala Ser
    225                 230                 235                 240
    His Glu Leu Lys Thr Pro Leu Ala Ser Leu Lys Ile Leu Ile Glu Asn
                    245                 250                 255
    Met Arg Glu Asn Ile Gly Arg Tyr Lys Asp Arg Asp Gln Tyr Leu Gly
                    260                 265                 270
    Val Ala Leu Gly Ile Val Asp Glu Leu Asn His His Val Leu Gln Ile
                275                 280                 285
    Leu Ser Leu Ser Ser Val Gln Glu Leu Arg Asp Asp Arg Glu Thr Ile
    290                 295                 300
    Asp Leu Leu Gln Met Thr Gln Asn Leu Val Lys Asp Tyr Ala Leu Leu
    305                 310                 315                 320
    Ala Lys Glu Arg Glu Leu Gln Ile Asp Asn Ser Leu Thr His Gln Gln
                    325                 330                 335
    Ala Tyr Leu Asn Pro Ser Val Met Lys Leu Ile Leu Ser Asn Leu Ile
                    340                 345                 350
    Ser Asn Ala Ile Lys His Ser Val Pro Gly Gly Leu Val Arg Ile Gly
                355                 360                 365
    Glu Arg Glu Gly Glu Leu Phe Ile Glu Asn Ser Cys Ser Ser Glu Glu
    370                 375                 380
    Gln Glu Lys Leu Ala Gln Ser Phe Ser Asp Asn Ala Ser Arg Lys Val
    385                 390                 395                 400
    Lys Gly Ser Gly Met Gly Leu Phe Val Val Lys Ser Leu Leu Glu His
                    405                 410                 415
    Glu Lys Leu Ala Tyr Arg Phe Glu Met Glu Glu Asn Ser Leu Thr Phe
                    420                 425                 430
    Phe Ile Asp Phe Pro Lys Val Val Gln Asp
                    435                 440

<210> SEQ ID NO 15
<211> LENGTH: 657
<212> TYPE: DNA
<213> ORGANISM: Streptococcus pneumoniae

<400> SEQUENCE: 15
atgaaaattt taattgtaga agatgaagag atgatccgtg aggggggtcag tgattatttg    60
    acggattgtg gctatgaaac tattgaggca gcggacggtc aggaagctct ggagcaattt   120
    tctagctatg aggtggccct ggttttactg gatatccaga tgcccaagct caacggctta   180
    gaagtcctag ctgagattcg taaaaccagt caggttcctg tcttgatgtt gacagctttt   240
    caagatgagg aatacaagat gagtgccttt gcctctttgg cagatggcta tctgaaaaaa   300
    ccttttctcc tctcccttt aaaagtgagg gtggacgcga ttttcaagcg ctactacgat   360
    acaggacgaa tcttttctta caaggatacc aaggtggaca ttgaaagcta cagtgcaagc   420
    ctcgcaggtc aagaagtgcc tatcaatgcc aaagagttgg aaattctgga ctatctagtg   480
    aaaaatgaag gccgggcctt gactcgatct cagattatcg atgccgtctg gaaagcgaca   540
    gatgaggttc cctttgaccg tgttattgat gtttatatca aggaattgcg gaaaaagcta   600
    gacttggatt gtatcctcac tgtgcgcaat gttggttata aattggagcg aaaatga      657
```

<210> SEQ ID NO 16
<211> LENGTH: 218
<212> TYPE: PRT
<213> ORGANISM: Streptococcus pneumoniae

<400> SEQUENCE: 16

```
Met Lys Ile Leu Ile Val Glu Asp Glu Glu Met Ile Arg Glu Gly Val
  1               5                  10                  15
Ser Asp Tyr Leu Thr Asp Cys Gly Tyr Glu Thr Ile Glu Ala Ala Asp
             20                  25                  30
Gly Gln Glu Ala Leu Glu Gln Phe Ser Ser Tyr Glu Val Ala Leu Val
         35                  40                  45
Leu Leu Asp Ile Gln Met Pro Lys Leu Asn Gly Leu Glu Val Leu Ala
 50                  55                  60
Glu Ile Arg Lys Thr Ser Gln Val Pro Val Leu Met Leu Thr Ala Phe
 65                  70                  75                  80
Gln Asp Glu Glu Tyr Lys Met Ser Ala Phe Ala Ser Leu Ala Asp Gly
                 85                  90                  95
Tyr Leu Glu Lys Pro Phe Ser Leu Ser Leu Lys Val Arg Val Arg Asp
             100                 105                 110
Ala Ile Phe Lys Arg Tyr Tyr Asp Thr Gly Arg Ile Phe Ser Tyr Lys
         115                 120                 125
Asp Thr Lys Val Asp Phe Glu Ser Tyr Ser Ala Ser Leu Ala Gly Gln
     130                 135                 140
Glu Val Pro Ile Asn Ala Lys Glu Leu Glu Ile Leu Asp Tyr Leu Val
145                 150                 155                 160
Lys Asn Glu Gly Arg Ala Leu Thr Arg Ser Gln Ile Ile Asp Ala Val
                165                 170                 175
Trp Lys Ala Thr Asp Glu Val Pro Phe Asp Arg Val Ile Asp Val Tyr
            180                 185                 190
Ile Lys Glu Leu Arg Lys Lys Leu Asp Leu Asp Cys Ile Leu Thr Val
        195                 200                 205
Arg Asn Val Gly Tyr Lys Leu Glu Arg Lys
    210                 215
```

<210> SEQ ID NO 17
<211> LENGTH: 648
<212> TYPE: DNA
<213> ORGANISM: Streptococcus pneumoniae

<400> SEQUENCE: 17

```
atgactttat tacaattaca agatgttacc taccgttata agaatactgc tgaagcagtc   60
ctatatcaga tcaattataa ttttgaaccc ggaaaatttt acagtattat tggggagtca  120
ggagcaggaa aatccacact cttgtcccta cttgctggtc tagatagtcc tgttgaaggt  180
tctatccttt ttcaaggaga ggatattcgt aagaagggct attcttacca tcgcatgcac  240
catatttccc tggtctttca aaattataac ttgatagatt atctttctcc gctggaaaat  300
atccgattgg tcaacaaaaa ggcaagcaag aatacacttc ttgagcttgg tttggatgaa  360
agccagatca agcggaatgt tctccagtta tcaggtggtc aacagcaacg tgttgccatt  420
gctcgcagtt tggtctcaga agctccagtt attctagctg atgagccaac aggaaatctg  480
gatcctaaaa ctgctggaga tattgtcgaa ctactcaaat cacttgccca gaaaacaggt  540
aaatgtgtga ttgtcgtaac tcacagtaaa gaagtggcac aagcgtcaga tattacactt  600
gaattaaagg ataagaaact gactgaaacg cgcaatacta gtaaataa                648
```

<210> SEQ ID NO 18
<211> LENGTH: 215
<212> TYPE: PRT
<213> ORGANISM: Streptococcus pneumoniae

<400> SEQUENCE: 18

```
Met Thr Leu Leu Gln Leu Gln Asp Val Thr Tyr Arg Tyr Lys Asn Thr
  1               5                  10                  15
Ala Glu Ala Val Leu Tyr Gln Ile Asn Tyr Asn Phe Glu Pro Gly Lys
             20                  25                  30
Phe Tyr Ser Ile Ile Gly Glu Ser Gly Ala Gly Lys Ser Thr Leu Leu
         35                  40                  45
Ser Leu Leu Ala Gly Leu Asp Ser Pro Val Glu Gly Ser Ile Leu Phe
 50                  55                  60
Gln Gly Glu Asp Ile Arg Lys Lys Gly Tyr Ser Tyr His Arg Met His
 65                  70                  75                  80
His Ile Ser Leu Val Phe Gln Asn Tyr Asn Leu Ile Asp Tyr Leu Ser
                 85                  90                  95
Pro Leu Glu Asn Ile Arg Leu Val Asn Lys Lys Ala Ser Lys Asn Thr
             100                 105                 110
```

-continued

```
        Leu Leu Glu Leu Gly Leu Asp Glu Ser Gln Ile Lys Arg Asn Val Leu
                    115                 120                 125
        Gln Leu Ser Gly Gly Gln Gln Arg Val Ala Ile Ala Arg Ser Leu
                130                 135                 140
        Val Ser Glu Ala Pro Val Ile Leu Ala Asp Glu Pro Thr Gly Asn Leu
        145                 150                 155                 160
        Asp Pro Lys Thr Ala Gly Asp Ile Val Glu Leu Leu Lys Ser Leu Ala
                        165                 170                 175
        Gln Lys Thr Gly Lys Cys Val Ile Val Val Thr His Ser Lys Glu Val
                    180                 185                 190
        Ala Gln Ala Ser Asp Ile Thr Leu Glu Leu Lys Asp Lys Lys Leu Thr
                195                 200                 205
        Glu Thr Arg Asn Thr Ser Lys
        210                 215
```

<210> SEQ ID NO 19
<211> LENGTH: 1380
<212> TYPE: DNA
<213> ORGANISM: Streptococcus pneumoniae

<400> SEQUENCE: 19

```
        atgttacaca acgcatttgc ctatgttaca aggaagtttt tcaaatcgat tgtcatcttc   60
        ctgattattc tcctcatggc gagcttgagt ttggtcggct tgtcaatcaa gggagctact  120
        gccaaggctt ctcaggagac ctttaaaaat atcaccaata gcttctccat gcaaatcaat  180
        cgtcgcgtca accaaggaac gcctcgtggt gctgggaata tcaagggtga agacatcaaa  240
        aaaatcaccg aaaacaaggc cattgagtct tatgtcaaac gatcaacgc tatcggagat  300
        ttgactggat atgacctgat tgaaacgcca gaaaccaaga agaatctcac tgctgatcgt  360
        gccaagcgtt ttggaagtag cttgatgatt acaggtgtca atgactcctc taaagaagac  420
        aagtttgtct ctggttctta taaactagtc gaaggagagc acttaaccaa cgacgacaag  480
        gataaaatcc tcttgcacaa ggacttggca gccaaacacg gctggaaagt aggggacaag  540
        gttaaactgg actctaatat ctacgatgca gataatgaaa aaggagccaa ggaaacagtt  600
        gaagtgacaa tcaagggact ctttgatggt cataataagt cagcagtaac ctactcacaa  660
        gaactttacg aaaacacagc tattacagac attcacactg ctgcaaaact ttatggatac  720
        acagaagaca cagccatta tgggacgaca accttctttg taacagcaga caagaacttg  780
        gatgatgtta tgaaagagtt gaatggcatc agtggtatca actggaagag ctacacactc  840
        gtcaagagct cctctaacta cccagctctt gagcaatcta tctctggtat gtacaagatg  900
        gccaacctcc tcttctgggg tagcttgagc ttctcagttc tcctccttgc cctcttgctc  960
        agcctttgga tcaacgcccg tcgcaaggaa gtgggaattc tcctctctat cggcctcaag 1020
        caggcaagta tcttgggtca attcatcacc gaatctatct tgattgctat ccctgctcta 1080
        gtttctgctt acttcctagc taattacact gcccgtgcaa ttggaaacac tgtccttgcc 1140
        aatgtgactt caggtgttgc caaacaggct agtaaggcgg ctcaagcctc taaccttggt 1200
        ggtggtgcag aagtagatgg ctttagcaag accttgtcga gcctagacat tccattcag  1260
        acatcagact ttatcatcat ttttgtcctt gccttggttc tagtggttct cgttatggcg 1320
        cttgcttcaa gcaatctcct tagaaaacaa ccaaaagagc tcttgctgga tggtgaataa 1380
```

<210> SEQ ID NO 20
<211> LENGTH: 459
<212> TYPE: PRT
<213> ORGANISM: Streptococcus pneumoniae

<400> SEQUENCE: 20

```
        Met Leu His Asn Ala Phe Ala Tyr Val Thr Arg Lys Phe Phe Lys Ser
        1               5                  10                  15
        Ile Val Ile Phe Leu Ile Ile Leu Leu Met Ala Ser Leu Ser Leu Val
                    20                  25                  30
        Gly Leu Ser Ile Lys Gly Ala Thr Ala Lys Ala Ser Gln Glu Thr Phe
                35                  40                  45
        Lys Asn Ile Thr Asn Ser Phe Ser Met Gln Ile Asn Arg Arg Val Asn
        50                  55                  60
        Gln Gly Thr Pro Arg Gly Ala Gly Asn Ile Lys Gly Glu Asp Ile Lys
        65                  70                  75                  80
        Lys Ile Thr Glu Asn Lys Ala Ile Glu Ser Tyr Val Lys Arg Ile Asn
                        85                  90                  95
        Ala Ile Gly Asp Leu Thr Gly Tyr Asp Leu Ile Glu Thr Pro Glu Thr
                    100                 105                 110
        Lys Lys Asn Leu Thr Ala Asp Arg Ala Lys Arg Phe Gly Ser Ser Leu
                115                 120                 125
        Met Ile Thr Gly Val Asn Asp Ser Ser Lys Glu Asp Lys Phe Val Ser
        130                 135                 140
        Gly Ser Tyr Lys Leu Val Glu Gly Glu His Leu Thr Asn Asp Asp Lys
        145                 150                 155                 160
        Asp Lys Ile Leu Leu His Lys Asp Leu Ala Ala Lys His Gly Trp Lys
                        165                 170                 175
        Val Gly Asp Lys Val Lys Leu Asp Ser Asn Ile Tyr Asp Ala Asp Asn
                    180                 185                 190
```

-continued

```
        Glu Lys Gly Ala Lys Glu Thr Val Glu Val Thr Ile Lys Gly Leu Phe
                    195                 200                 205
        Asp Gly His Asn Lys Ser Ala Val Thr Tyr Ser Gln Glu Leu Tyr Glu
            210                 215                 220
        Asn Thr Ala Ile Thr Asp Ile His Thr Ala Ala Lys Leu Tyr Gly Tyr
        225                 230                 235                 240
        Thr Glu Asp Thr Ala Ile Tyr Gly Asp Ala Thr Phe Val Thr Ala
                        245                 250                 255
        Asp Lys Asn Leu Asp Asp Val Met Lys Glu Leu Asn Gly Ile Ser Gly
                    260                 265                 270
        Ile Asn Trp Lys Ser Tyr Thr Leu Val Lys Ser Ser Asn Tyr Pro
                275                 280                 285
        Ala Leu Glu Gln Ser Ile Ser Gly Met Tyr Lys Met Ala Asn Leu Leu
            290                 295                 300
        Phe Trp Gly Ser Leu Ser Phe Ser Val Leu Leu Ala Leu Leu Leu
        305                 310                 315                 320
        Ser Leu Trp Ile Asn Ala Arg Arg Lys Glu Val Gly Ile Leu Leu Ser
                        325                 330                 335
        Ile Gly Leu Lys Gln Ala Ser Ile Leu Gly Gln Phe Ile Thr Glu Ser
                    340                 345                 350
        Ile Leu Ile Ala Ile Pro Ala Leu Val Ser Ala Tyr Phe Leu Ala Asn
                355                 360                 365
        Tyr Thr Ala Arg Ala Ile Gly Asn Thr Val Leu Ala Asn Val Thr Ser
        370                 375                 380
        Gly Val Ala Lys Gln Ala Ser Lys Ala Ala Gln Ala Ser Asn Leu Gly
                        385                 390                 395                 400
        Gly Gly Ala Glu Val Asp Gly Phe Ser Lys Thr Leu Ser Ser Leu Asp
                    405                 410                 415
        Ile Ser Ile Gln Thr Ser Asp Phe Ile Ile Ile Phe Val Leu Ala Leu
                420                 425                 430
        Val Leu Val Val Leu Val Met Ala Leu Ala Ser Ser Asn Leu Leu Arg
            435                 440                 445
        Lys Gln Pro Lys Glu Leu Leu Leu Asp Gly Glu
            450                 455
```

<210> SEQ ID NO 21
<211> LENGTH: 1278
<212> TYPE: DNA
<213> ORGANISM: Streptococcus pneumoniae

<400> SEQUENCE: 21

```
atgaatccaa tccaaagatc ttgggcttat gtcagcagaa agcgactgag aagttttatt   60
ttatttctga tttttattggt cttattggcc ggaatttcag cctgtttgac tctgatgaag  120
tccaacaaaa cagtagaaag caatctttat aaatcactca atacatcttt ttctattaag  180
aagatagaga atggtcagac attcaagttg tcagacctag catctgtaag caagattaag  240
gggctggaaa atgtctctcc tgaacttgag acggtcgcaa actaaaagaa caaggaagca  300
gtgactggcg agcagagcgt ggagcgtgat gatttatcag ctgcagacaa taacttggtt  360
agcttaacgg ctcttgagga ttcatccaag gatgtaacct ttaccagttc ggcttttcaat  420
ctaaaagaag gcgacacct tcaaaaaggg gattccaaga aaatcettat ccacgaagaa  480
ttggctaaga agaacggtct ttcgcttcat gacaagattg gcttggatgc tggtcagtct  540
gaatctggaa aaggacaaac agtagagttt gagattatcg gcatcttttc tggtaaaaaa  600
caagagaaat tcacaggctt gtcttctgac ttcagtgaaa atcaagtctt tacagactat  660
gaaagtagcc aaaacccttt gggcaatagt gaagctcaag tcagtgcagc acgcttctat  720
gtagaaaatc ctaaggaaat ggacggactc atgaagcagg tagaaaactt ggccttggaa  780
aatcaaggct accaagtcga aaaggaaaac aaggcttttg aacaaatcaa agactcagtt  840
gcaactttcc aaaccttcct gaccatcttc ctttatggga tgttgatagc aggagctgga  900
gccttaattc tggttttgtc tctctggttg agagaacggg tctatgaagt ggggatttta  960
cttgcacttg aaaaggcaa gagctcgatc ttcctacaat ctgttttaga ggtagttttg 1020
gtatctcttg gagctttgct tccagcattt gttgcaggaa acgcaatcac aacttaccta 1080
ctccaaactc tactagcaag tggagatcag gcaagcttac aagatacact agccaaagca 1140
agcagtttat caactagcat cttatctttt gcagaatcct atgttttct agttctgctt 1200
agttgcttat ctgtagccct tgtttccta ttcttattta gaaaatcacc gaagaaatt 1260
ttatcatcta ttagttaa                                               1278
```

<210> SEQ ID NO 22
<211> LENGTH: 425
<212> TYPE: PRT
<213> ORGANISM: Streptococcus pneumoniae

<400> SEQUENCE: 22

```
        Met Asn Pro Ile Gln Arg Ser Trp Ala Tyr Val Ser Arg Lys Arg Leu
        1               5                   10                  15
        Arg Ser Phe Ile Leu Phe Leu Ile Leu Leu Val Leu Leu Ala Gly Ile
                    20                  25                  30
```

```
           Ser Ala Cys Leu Thr Leu Met Lys Ser Asn Lys Thr Val Glu Ser Asn
                       35                  40                  45
           Leu Tyr Lys Ser Leu Asn Thr Ser Phe Ser Ile Lys Ile Glu Asn
               50                  55                  60
           Gly Gln Thr Phe Lys Leu Ser Asp Leu Ala Ser Val Ser Lys Ile Lys
           65                  70                  75                  80
           Gly Leu Glu Asn Val Ser Pro Glu Leu Thr Val Ala Lys Leu Lys
                           85                  90                  95
           Asp Lys Glu Ala Val Thr Gly Glu Gln Ser Val Glu Arg Asp Leu
                       100                 105                 110
           Ser Ala Ala Asp Asn Asn Leu Val Ser Leu Thr Ala Leu Glu Asp Ser
                       115                 120                 125
           Ser Lys Asp Val Thr Phe Thr Ser Ser Ala Phe Asn Leu Lys Glu Gly
                       130                 135                 140
           Arg His Leu Gln Lys Gly Asp Ser Lys Lys Ile Leu Ile His Glu Glu
           145                 150                 155                 160
           Leu Ala Lys Lys Asn Gly Leu Ser Leu His Asp Lys Ile Gly Leu Asp
                           165                 170                 175
           Ala Gly Gln Ser Glu Ser Gly Lys Gly Gln Thr Val Glu Phe Glu Ile
                       180                 185                 190
           Ile Gly Ile Phe Ser Gly Lys Lys Gln Glu Lys Phe Thr Gly Leu Ser
                       195                 200                 205
           Ser Asp Phe Ser Glu Asn Gln Val Phe Thr Asp Tyr Glu Ser Ser Gln
                       210                 215                 220
           Thr Leu Leu Gly Asn Ser Glu Ala Gln Val Ser Ala Ala Arg Phe Tyr
           225                 230                 235                 240
           Val Glu Asn Pro Lys Glu Met Asp Gly Leu Met Lys Gln Val Glu Asn
                           245                 250                 255
           Leu Ala Leu Glu Asn Gln Gly Tyr Gln Val Glu Lys Glu Asn Lys Ala
                       260                 265                 270
           Phe Glu Gln Ile Lys Asp Ser Val Ala Thr Phe Gln Thr Phe Leu Thr
                       275                 280                 285
           Ile Phe Leu Tyr Gly Met Leu Ile Ala Gly Ala Gly Ala Leu Ile Leu
                       290                 295                 300
           Val Leu Ser Leu Trp Leu Arg Glu Arg Val Tyr Glu Val Gly Ile Leu
           305                 310                 315                 320
           Leu Ala Leu Gly Lys Gly Lys Ser Ile Phe Leu Gln Phe Cys Leu
                       325                 330                 335
           Glu Val Val Leu Val Ser Leu Gly Ala Leu Leu Pro Ala Phe Val Ala
                       340                 345                 350
           Gly Asn Ala Ile Thr Thr Tyr Leu Leu Gln Thr Leu Leu Ala Ser Gly
                       355                 360                 365
           Asp Gln Ala Ser Leu Gln Asp Thr Leu Ala Lys Ala Ser Ser Leu Ser
                       370                 375                 380
           Thr Ser Ile Leu Ser Phe Ala Glu Ser Tyr Val Phe Leu Val Leu Leu
           385                 390                 395                 400
           Ser Cys Leu Ser Val Ala Leu Cys Phe Leu Phe Leu Phe Arg Lys Ser
                           405                 410                 415
           Pro Lys Glu Ile Leu Ser Ser Ile Ser
                       420                 425

<210> SEQ ID NO 23
<211> LENGTH: 1407
<212> TYPE: DNA
<213> ORGANISM: Streptococcus pneumoniae

<400> SEQUENCE: 23
atgccgaacg gcacgtatgg tggtgtgaga ggggctagag attatcccct actcgatatt    60
           ttttttttcgt atttcataaa tatttcatat ttgggtttta taatagtctt acaaatatgg   120
           aggtgacaaa tgaatccaat ccaaagatct tgggcttatg tcagcagaaa gcgactgaga   180
           agtttatttt tatttctgat tttattggtc ttattggccg gaatttcagc ctgtttgact   240
           ctgatgaagt ccaacaaaac agtagaaagc aatctttata atcactcaa tacatctttt    300
           tctattaaga agatagagaa tggtcagaca ttcaagttgt cagacctagc atctgtaagc   360
           aagattaagg ggctggaaaa tgtctctcct gaacttgaga cggtcgcaaa actaaaagac   420
           aaggaagcag tgactggcga gcagagcgtg gagcgtgatg atttatcagc tgcagacaat   480
           aacttggtta gcttaacggc tcttgaggat tcatccaagg atgtaacctt accagttcg    540
           gctttcaatc taaaagaagg gcgacacctt caaaagggg attccaagaa aatccttatc   600
           cacgaagaat tggctaagaa gaacggtctc tcgcttcatg acaagattgg cttggatgct   660
           ggtcagtctg aatctggaaa aggacaaaca gtagagtttg agattatcgg catcttttct   720
           ggtaaaaaac aagagaaatt cacaggcttg tcttctgact cagtgaaaa tcaagtctt    780
           acagactatg aaagtagcca aacccttttg gcaatagtg aagctcaagt cagtgcagca   840
           cgcttctatg tagaaaatcc taaggaaatg gacggactca tgaagcaggt cgaaaacttg   900
           gccttggaaa atcaaggcta ccaagtcgaa aaggaaaaca aggcttttga acaaatcaaa   960
           gactcagttg caactttcca aaccttcctg accatcttcc tttatgggat gttgatagca  1020
           ggagctggag ccttaattct ggttttgtct ctctggttga gaaacgggc tatgaagtg   1080
           gggattttac ttgcacttgg aaaaggcaag agctcgatct tcctacaatt ctgtttagag  1140
           gtagttttgg tatctcttgg agcttttgctt ccagcatttg ttgcaggaaa cgcaatcaca  1200
```

```
        acttacctac tccaaactct actagcaagt ggagatcagg caagcttaca agatacacta   1260
        gccaaagcaa gcagtttatc aactagcatc ttatcttttg cagaatccta tgtttttcta   1320
        gttctgctta gttgcttatc tgtagccctt tgtttcctat tcttatttag aaaatcaccg   1380
        aaagaaattt tatcatctat tagttaa                                       1407
```

<210> SEQ ID NO 24
<211> LENGTH: 425
<212> TYPE: PRT
<213> ORGANISM: Streptococcus pneumoniae

<400> SEQUENCE: 24

```
Met Asn Pro Ile Gln Arg Ser Trp Ala Tyr Val Ser Arg Lys Arg Leu
  1               5                  10                  15
Arg Ser Phe Ile Leu Phe Leu Ile Leu Val Leu Leu Ala Gly Ile
             20                  25                  30
Ser Ala Cys Leu Thr Leu Met Lys Ser Asn Lys Thr Val Glu Ser Asn
         35                  40                  45
Leu Tyr Lys Ser Leu Asn Thr Ser Phe Ser Ile Lys Ile Glu Asn
     50                  55                  60
Gly Gln Thr Phe Lys Leu Ser Asp Leu Ala Ser Val Ser Lys Ile Lys
 65                  70                  75                  80
Gly Leu Glu Asn Val Ser Pro Glu Leu Glu Thr Val Ala Lys Leu Lys
                 85                  90                  95
Asp Lys Glu Ala Val Thr Gly Glu Gln Ser Val Glu Arg Asp Asp Leu
            100                 105                 110
Ser Ala Ala Asp Asn Asn Leu Val Ser Leu Thr Ala Leu Glu Asp Ser
        115                 120                 125
Ser Lys Asp Val Thr Phe Thr Ser Ser Ala Phe Asn Leu Lys Glu Gly
    130                 135                 140
Arg His Leu Gln Lys Gly Asp Ser Lys Lys Ile Leu Ile His Glu Glu
145                 150                 155                 160
Leu Ala Lys Lys Asn Gly Leu Ser Leu His Asp Lys Ile Gly Leu Asp
                165                 170                 175
Ala Gly Gln Ser Glu Ser Gly Lys Gly Gln Thr Val Glu Phe Glu Ile
            180                 185                 190
Ile Gly Ile Phe Ser Gly Lys Lys Gln Glu Lys Phe Thr Gly Leu Ser
        195                 200                 205
Ser Asp Phe Ser Glu Asn Gln Val Phe Thr Asp Tyr Glu Ser Ser Gln
    210                 215                 220
Thr Leu Leu Gly Asn Ser Glu Ala Gln Val Ser Ala Ala Arg Phe Tyr
225                 230                 235                 240
Val Glu Asn Pro Lys Glu Met Asp Gly Leu Met Lys Gln Val Glu Asn
                245                 250                 255
Leu Ala Leu Glu Asn Gln Gly Tyr Gln Val Glu Lys Glu Asn Lys Ala
            260                 265                 270
Phe Glu Gln Ile Lys Asp Ser Val Ala Thr Phe Gln Thr Phe Leu Thr
        275                 280                 285
Ile Phe Leu Tyr Gly Met Leu Ile Ala Gly Ala Gly Ala Leu Ile Leu
    290                 295                 300
Val Leu Ser Leu Trp Leu Arg Glu Arg Val Tyr Glu Val Gly Ile Leu
305                 310                 315                 320
Leu Ala Leu Gly Lys Gly Lys Ser Ile Phe Leu Gln Phe Cys Leu
                325                 330                 335
Glu Val Val Leu Val Ser Leu Gly Ala Leu Leu Pro Ala Phe Val Ala
            340                 345                 350
Gly Asn Ala Ile Thr Thr Tyr Leu Leu Gln Thr Leu Leu Ala Ser Gly
        355                 360                 365
Asp Gln Ala Ser Leu Gln Asp Thr Leu Ala Lys Ala Ser Ser Leu Ser
    370                 375                 380
Thr Ser Ile Leu Ser Phe Ala Glu Ser Tyr Val Phe Leu Val Leu Leu
385                 390                 395                 400
Ser Cys Leu Ser Val Ala Leu Cys Phe Leu Phe Leu Phe Arg Lys Ser
                405                 410                 415
Pro Lys Glu Ile Leu Ser Ser Ile Ser
            420                 425
```

<210> SEQ ID NO 25
<211> LENGTH: 8900
<212> TYPE: DNA
<213> ORGANISM: Streptococcus pneumoniae

<400> SEQUENCE: 25

```
        gataagtttg tagcagctat ggatgaagat tttaatgctg ccaacggtat cacagttgtc   60
        tttgaaatgg ccaaatggat caactcaggg aactatgatg caagtgtcaa gcaagctctt   120
        gcagatatgt tagaaatttt tggaattgtc tttgttgagg aagttttgga tgcagagatt   180
```

-continued

```
gaagacttga ttcaaaaacg ccaagaggcg cgtgccaatc gtgactttgc gacagcagac 240
caaatccgtg accaattggt tactcaagga attaagctcc ttgataccaa ggatggagtg 300
aggtggacac gtgattgatg tcaatctcat taacggcagt gcgctagcct ttgaggggga 360
tgcggtgtat tctatgtata ttcgccgtca cctcatcctc aaaggtatga ccaaacccaa 420
taaactccat caagaagcaa ctaagtacgt gtcagccaag gctcaggctc gcctgattgc 480
tctcatgttg gaggagcagg tcctaacgga aaaagaagaa gaaatctaca acgtggccg 540
caataccaat agccacacaa aggctaaaaa tgcagatgtc gtgacttatc gtatgtccac 600
gggatttgaa gcggttatgg gctatctcca tatgactgag aatctggaac gtcttgagag 660
tttggtttca tggtgcatcc aaaaagtgga gggctagaac atgagggcaa aagaactaca 720
agactggttt cctgaggctc ggatttcaga ccaaccagta gagaagagg gctatctcac 780
gctcccttta gcttctcagc agtggatttt gctggaggaa gctgggctca ttgccgcgtga 840
aaagcagttg gttgcccttt tgacccagca ggagcaggct cgttcgctaa acccttggta 900
ttcctatctg gttgagggca agggacaggc accgcaagtt tttaaaaaga ttcagttggt 960
ttattgccat ctttcttatt ttcagcagga aaatctggct tcttggctag atatgatgcg 1020
gactctttt ccgaattgtc agacagtgct acaggtcgga gctcaggatt atgtttttcgt 1080
gcttcaacaa gacaaataca cttctgtaag agatatttta agtgatacga ttgaagcggt 1140
tgagtatgac tttgacttc gtctttctat catgtgggt caggtttggt ctcagacggg 1200
acatcaagcc ctatcagact taatcaaagc tgagcgggat ttgttcaaga catggtggcg 1260
tcagggtcac caaggtgttc atacttttc tcagctctat ctttggagta tgggagaaag 1320
actcgtggac ttgaagccaa tcaaggaatg tctacaccag atgattttttg atcaagatca 1380
gattcaggaa atcattctct ctctttggga aaatagtgct gttctcacta aaacagccca 1440
gcaactctat ctgcaccgca attctctcca atacaagatt gataaatggg aagagttgac 1500
agggcttcag ttgaaagagt tgaccgacct gaccttgtgt tatcaattga ttttaggttc 1560
tttgtcaact atagttggtt tgtaaaagaag ttaatatttg aggaagagga ttgccatctt 1620
ctccatttt atgtgcagag ttatagtggc ttgatgctgg gaaagtacac tgtgactgct 1680
aaaacattcc tagaagctgc tttgatttcc ctaatctatt tatgcaaatt ttatgttatt 1740
ttactataac agttgttgct aagccaaata atagtgggga agttcattta gacgtaagca 1800
ttgaagataa tcagggaggt agtgggtata atttcagttc tgttttcaagt agctcacaaa 1860
cagctaaata tgaaggaact gtttataata acaattcatc attatatata acgattgata 1920
aaacgtctga tgcaacagct cttttgaaat taaagttgaa taatgttgat aatcaacctg 1980
ctactgaagt tcctagttca ggaattactg taaaattaaa tgctaaagat aatgctggaa 2040
actggacaag tgcttcgaat aaaaaagaag taacagtaaa aattgtttct gctaaaccga 2100
catatccaga caaaatctta gtgaaaaatc ctgataatat aaaagataca gaaaaaatgc 2160
cattattgaa aaattgaaag aggcaaataa aaatcatcca gcaggagctc caacctttgc 2220
taaaggtgaa ggagagcatg caaatgatat tgtagcaact tattcagatg gtacaactta 2280
ttatgtaccg ttaaatgatg tgacaaaata tgcgaggtag tggctgtacc actcacttat 2340
tcacctcccc gtgatttgta gtagtgatag gtttctcac tattattata aaacaaaata 2400
aagatcacaa cacttttttca ttctgtgttg tgccttgagt gaacgaaag gaatgaatta 2460
taaatatgaa aagtatagtc actagcatag atgagcgctt gcgtactcgc ctacgagtga 2520
ttatctggaa gcaatggaag aagaaatcga gacgattatg gggattgctt aagttagggg 2580
ttcctaaatg gatagcagat aaggtatctg gctggggcga ccactatcaa ttatagtaaa 2640
atgaaataag aataggacga attgttcagg acagtcaaat cgatttctaa caatattta 2700
gaagtagagg tgtactattc tagtttcaat ctactatagt agctcagaag tcggtactta 2760
aacgtgctat atcaaaacca gtccttgaaa aacgtggact ggttcgtgt ttggattatt 2820
accttgaacg acatgcgtta aaagttagtt gaaccgccgt atgccgaacg gcacgtatgg 2880
tggtgtgaga ggggctagag attatcccct actcgatatt tttttttcgt atttcataaa 2940
tatttcatat ttgggttta taatagtctt acaaatatgg aggtgacaaa tgaatccaat 3000
ccaaagatct tgggcttatg tcagcagaaa gcgactgaga agttttattt tatttctgat 3060
tttattggtc ttattggccg gaatttcagc ctgttttgact ctgatgaagt ccaacaaaac 3120
agtagaaagc aatctttata aatcactcaa tacatctttt tctattaaga agatagagaa 3180
tggtcagaca ttcaagttgt cagaccagc atctgtaagc aagattaagg ggctggaaaa 3240
tgtctctcct gaacttgaga cggtcgcaaa actaaaagac aaggaagcag tgactggcga 3300
gcagagcgtg gagcgtgatg attttatcagc tgcagacaat aacttggtta gcttaacgca 3360
tcttgaggat tcatccaagg atgtaacctt taccagttcg gctttcaatc taaaagaagg 3420
gcgacacctt caaaaggggg attccaagaa aatccttatc cacgaagaat tggctaagaa 3480
gaacggtctt tcgcttcatg acaagattgg cttggatgct ggtcagtctg aatctggaaa 3540
aggacaaaca gtagagtttg agattatcga catcttttct ggtaaaaaac aagagaaatt 3600
cacaggcttg tcttctgact tcagtgaaaa tcaagtcttt acagactatg aaagtagcca 3660
aaccctttg ggcaatagtg aagctcaagt cagtgcagca cgcttctatg tagaaaatcc 3720
taaggaaatg gacggactca tgaagcaggt agaaaacttg gccttggaaa atcaaggcta 3780
ccaagtcgaa aaggaaaaca aggcttttga acaaatcaaa gactcagttg caactttcaa 3840
aaccttcctg accatcttcc tttatgggat gttgatagca ggagctggag ccttaattct 3900
ggttttgtct ctctggttga gagaacgggt ctatgaagtg gggatttttac ttgcacttgg 3960
aaaaggcaag agctcgatct tcctacaatt ctgtttagag gtagttttgg tatctcttgg 4020
agctttgctt ccagcatttt ttgcaggaaa cgcaaatcaca acttacctac tccaaactct 4080
actagcaagt ggagatcagg caagcttaca agatacacta gccaaagcaa gcagtttatc 4140
aactagcatc ttatctttg cagaatccta tgtttttcta gttctgctta gttgcttatc 4200
tgtagccctt tgtttcctat tcttatttag aaaatcaccg aaagaaattt tatcatctat 4260
tagttaagaa ggagaaatca tgactttatt acaattacaa gatgttacct accgttataa 4320
gaatactgct gaagcagtcc tatatcgat caattataat tttgaacccg gaaaatttta 4380
cagtattatt ggggagtcag gagcaggaaa atccacactc ttgtcccctac ttgctggtct 4440
agatagtcct gttgaaggtt ctatccttt tcaaggagag gatattcgta gaagggcta 4500
ttcttaccat cgcatgcacc atatttccct ggtctttcaa aattataact tgatagatta 4560
tcttttctccg ctggaaaata tccgattggt caacaaaaag gcaagcaaga atacacttct 4620
tgagcttggt ttggatgaaa gccagatcaa gcggaatgtt ctccagttat caggtggtca 4680
acagcaacgt gttgccattg ctcgcagttt ggtctcagaa gctccagtta ttctagctga 4740
tgagccaaca ggaaatctgg atccaaaaac tgctggagat attgtcgaac tactcaaatc 4800
acttgcccag aaaacaggta aatgtgtgat tgtcgtaact cacagtaaag aagtggcaca 4860
agcgtcagat attacacttg aattaaagga taagaaactg actgaaacgc gcaatactag 4920
```

```
taaataattt gagcttattt taatagaatg attaaaacaa aatctagaaa gggaatctat   4980
gttacacaac gcatttgcct atgttacaag gaagttttc aaatcgattg tcatcttcct   5040
gattattctc ctcatggcga gcttgagttt ggtcggcttg tcaatcaagg gagctactgc   5100
caagcttct caggagacct ttaaaaatat caccaatagc ttctccatgc aaatcaatcg   5160
tcgcgtcaac caaggaacgc ctcgtggtgc tgggaatatc aagggtgaag acatcaaaaa   5220
aatcaccgaa aacaaggcca ttgagtctta tgtcaaacgt atcaacgcta tcggagattt   5280
gactggatat gacctgattg aaacgccaga aaccaagaag aatctcactg ctgatcgtgc   5340
caagcgtttt ggaagtagct tgatgattac aggtgtcaat gactcctcta agaagacaa   5400
gtttgtctct ggttcttata aactagtcga aggagagcac ttaaccaacg acgacaagga   5460
taaaatcctc ttgcacaagg acttggcagc caaacacggc tggaaagtag gggacaaggt   5520
taaactggac tctaatatct acgatcagaa taatgaaaaa ggagccaagg aaacagttga   5580
agtgacaatc aagggactct tgatggtca taataagtca gcagtaacct actcacaaga   5640
actttacgaa aacacagcta ttacagacat tcacactgct gcaaaacttt atggatacac   5700
agaagacaca gccatttatg gggacgcaac cttctttgta acagcagaca agaacttgga   5760
tgatgttatg aaagagttga atggcatcag tggtatcaac tggaagagct acacactcgt   5820
caagagctcc tctaactacc agctcttga gcaatctatc tctggtatgt acaagatggc   5880
caacctcctc ttctggggta gcttgagctt ctcagttctc ctccttgccc tcttgctcag   5940
cctttggatc aacgcccgtc gcaaggaagt gggaattctc ctctctatcg gcctcaagca   6000
ggcaagtatc ttgggtcaat tcatcaccga atctatcttg attgctatcc ctgctctagt   6060
ttctgcttac ttcctagcta attacactgc ccgtgcaatt ggaaacactg tccttgccaa   6120
tgtgacttca ggtgttgcca acaggctag taaggcgct caagcctcta accttggtgg   6180
tggtgcagaa gtagatggct ttagcaagac cttgtcgagc ctagacattt ccattcagac   6240
atcagacttt atcatcattt ttgtccttgc cttggttcta gtggttctcg ttatggcgct   6300
tgcttcaagc aatctcctta gaaaacaacc aaaagagctc ttgctggatg gtaataaat   6360
ttgaaaaat gagtctagaa taaagattgc atcttgtgtt tctattcaag aatagtgat   6420
aggaatggct atttaacaat tcaaaataaa tccgaaagca gtggtgaaaa tcattgcttt   6480
cagttgcttt cttttgtactt tagtgcttaa atataatata ctaaagttat ggaatttatg   6540
agaaaggaat ttcacaacgt tttatctagt ggtcagttgc ttgcagacaa aaggccagca   6600
agagactata atagaaaata gggtaggtat ttattctaag aaaaataaaa aatagagagc   6660
agttaaagta tgaaattttt aattgtagaa gatgaagaga tgatccgtga gggggtcagt   6720
gattatttga cggattgtgg ctatgaaact attgaggcag cggacggtca ggaagctctg   6780
gagcaattt ctagctatga ggtggccctg gttttactgg atatccagat gcccaagctc   6840
aacggcttag aagtcctagc tgagattcgt aaaaccagtc aggttcctgt cttgatgttg   6900
acagctttc aagatgagga atacaagatg agtgcctttg cctctttggc agatggctat   6960
ctggaaaaac ctttctccct ctccctttta aaagtgaggg tggacgcgat tttcaagcgc   7020
tactacgata caggacgaat cttttcttac aaggatacca aggtggactt tgaaagctac   7080
agtgcaagcc tcgcaggtca agaagtgcct atcaatgcca aagagttgga aattctggac   7140
tatctagtga aaaatgaagg ccgggccttg actcgatctc agattatcga tgccgtctgg   7200
aaagcgacag atgaggttcc ctttgaccgt gttattgatg tttatatcaa ggaattgcgg   7260
aaaaagctag acttggattg tatcctcact gtgcgcaatg ttggttataa attggagcga   7320
aaatgaaacg aacaggttta tttgcaaaga tatttatcta taccttctcg atatttagtg   7380
ttctggttat ctgccttcat ttagctattt attttcttt tccttcgact tatctgagtc   7440
atcgtcagga aaccattggt caaaaggcaa cagccattgc ccagtcccta gaagggaaag   7500
ataggcagag tatcgagcaa gtgttagact tgtattccca gactagtgat atcaagggga   7560
ccgtcaaagg tgagatgacc gaggacaagt tagaagtcaa ggacagtctt cctctggaca   7620
cagaccgcca gacaacctct ctctttattg aggagcgcga ggtgaaaacg caagacgtg   7680
gtactatgat tctccagttt ctagcttcca tggatttaca aaaggaagcg gagcaaatca   7740
gtctccagtt tctttcctat accttgctgg cctcctttct gatttccctt ttggtggcct   7800
acatctacgc tcggactatt gttgcaccga ttttggaaat caagcgggtg acccgtcgga   7860
tgatggacct ggattcccaa gtgcgattgc gcgtggattc taaggatgag ataggtaatc   7920
tcaaggaaca aatcaatagc ctctaccaga atctccttgac tgttattgcg gacttgcatg   7980
aaaagaatga agccattctc cagctggaga agatgaaggt cgaattccta cgaggagctt   8040
ctcatgaatt gaaaacaccg ctggctagtt tgaaaatcct aatcgaaaat atgagagaga   8100
atatcggtcg ttataaggat agagaccagt atctgggagt tgcctttggg attgtggatg   8160
aactcaatca ccatgttctg cagatacttt ccctctcttc tgtgcaggaa ttgcgagatg   8220
ataggggaaac aattgacctc ctccagatga cgcaaaatct ggtcaaagat tatgccttgc   8280
tagccaagga aagagactgc cagatagaca atagtttgac ccatcagcag gcttatctaa   8340
acccatcagt tatgaagttg attctttcta atctcatcag caatgccatt aagcactctg   8400
ttccaggtgg cttagttcga attggagaaa gagaaggaga acttttttatc gaaaatagct   8460
gtagctcaga ggaacaagaa aaactagccc agtctttttc tgacaatgcc agtcgcaagg   8520
tcaaggggtc tggtatgggg ctctttgtgg ttaagagtct attagaacat gaaaaattag   8580
cttatcgttt cgagatggag gagaatagtt taaccttctt tatagatttt ccaaaagtcg   8640
tccaagacta gggagagaaa gggtttacat agatgcagtt agaagaaaat caatcgaaac   8700
tgcgggaaaa actagatttt tttggcaaaa gtgataaaa tgaacaatgt aaatgggatg   8760
acccataaaa atatacagga ggcctgataa aatggcaatc gtttcagcag aaaaaatttgt   8820
ccaagcagcc cgtgacaacg gttatgcagt tggtggattt aacacaaaca accttgagtg   8880
gactcaagct atcttgcgcg                                              8900
```

<210> SEQ ID NO 26
<211> LENGTH: 25
<212> TYPE: PRT
<213> ORGAnISM: Methanococcus jannaschii

```
<400> SEQUENCE: 26

Asn Arg Lys Val Phe Ile Val Val Leu Ser Met Leu Leu Leu Ala
    1               5                   10                  15
    Met Glu Arg Pro Trp Cys Ser Leu Val
                20                  25

<210> SEQ ID NO 27
<211> LENGTH: 25
<212> TYPE: PRT
<213> ORGANISM: Haemophilus influenzae

<400> SEQUENCE: 27

Ser Ser Leu Leu Asp Gly Val Lys Ile Ala Ser Gly Asn Leu Leu Ala
    1               5                   10                  15
    Ser Thr Lys Pro Ser Gly Asn Phe Asn
                20                  25

<210> SEQ ID NO 28
<211> LENGTH: 25
<212> TYPE: PRT
<213> ORGANISM: Haemophilus influenzae

<400> SEQUENCE: 28

Ser Arg Lys Arg Phe His Gln Ile Leu Met Gln Gly Met Lys Leu Ala
    1               5                   10                  15
    Tyr Arg Ile Tyr Arg Ser Ser His Asp
                20                  25

<210> SEQ ID NO 29
<211> LENGTH: 25
<212> TYPE: PRT
<213> ORGANISM: Haemophilus influenzae

<400> SEQUENCE: 29

Arg Ser Asp Lys Phe His Ser Thr Ile Val Leu Ser Ser Val Leu Ala
    1               5                   10                  15
    Asp Lys Lys Thr Pro Arg Cys Cys His
                20                  25

<210> SEQ ID NO 30
<211> LENGTH: 25
<212> TYPE: PRT
<213> ORGANISM: Archaeoglobus fulgidus

<400> SEQUENCE: 30

His Val Glu Glu Leu His His Val Glu Ser Leu Ala Leu Leu Ser
    1               5                   10                  15
    Asp Lys Val Leu Cys Arg Asn Ser Tyr
                20                  25

<210> SEQ ID NO 31
<211> LENGTH: 25
<212> TYPE: PRT
<213> ORGANISM: Archaeoglobus fulgidus

<400> SEQUENCE: 31

Thr Gly Arg Glu Ala Arg Arg Ile Ile Ser Ala Gly Glu Ile Leu Val
    1               5                   10                  15
    Asp Gly Val Val Arg Lys Asp Tyr Lys
                20                  25

<210> SEQ ID NO 32
<211> LENGTH: 25
<212> TYPE: PRT
<213> ORGANISM: Archaeoglobus fulgidus
```

```
<400> SEQUENCE: 32

Arg Cys Leu Arg Arg Asp Ser Leu Phe Ser Ser Gly Cys Leu Leu Ala
       1               5                  10                  15
     Gly Glu Glu Pro Ser Arg Arg Ser Cys
                 20                  25

<210> SEQ ID NO 33
<211> LENGTH: 25
<212> TYPE: PRT
<213> ORGANISM: Borrelia burgdorferi

<400> SEQUENCE: 33

Val Leu Arg Thr His Gly Thr Val Leu Ser Ala Lys Gln Leu Ile Asn
       1               5                  10                  15
     Ala Lys Asn Pro Ser Arg Tyr Phe Gly
                 20                  25

<210> SEQ ID NO 34
<211> LENGTH: 20
<212> TYPE: PRT
<213> ORGANISM: Synechocystis sp.

<400> SEQUENCE: 34

Leu Lys Glu Glu Phe Glu Lys Phe Arg Ser Ala Gly Glu Lys Leu Leu
       1               5                  10                  15
     Asp Phe Arg Pro
                 20

<210> SEQ ID NO 35
<211> LENGTH: 12
<212> TYPE: PRT
<213> ORGANISM: Synechocystis sp.

<400> SEQUENCE: 35

Phe Gly Asn Gln Leu Ser Ile Gly Gln Leu Ile Ala
       1               5                  10

<210> SEQ ID NO 36
<211> LENGTH: 25
<212> TYPE: PRT
<213> ORGANISM: Artificial Sequence
<220> FEATURE:
<223> OTHER INFORMATION: Description of Artificial Sequence: Modified
      Streptococcus Pneumonia peptide
<220> FEATURE:
<221> NAME/KEY: VARIANT
<222> LOCATION: (24)
<223> OTHER INFORMATION: It can be any amino acid at this position.

<400> SEQUENCE: 36

Met Arg Lys Glu Phe His Asn Val Leu Ser Ser Gly Gln Leu Leu Ala
       1               5                  10                  15
     Asp Lys Arg Pro Ala Arg Asp Xaa Asn
                 20                  25

<210> SEQ ID NO 37
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 37
aatgagtcta gaataaagat tgc                                        23

<210> SEQ ID NO 38
<211> LENGTH: 21
```

```
<212> TYPE: DNA
<213> ORGANISM: Artificial Sequence
<220> FEATURE:
<223> OTHER INFORMATION: Description of Artificial Sequence: Primer

<400> SEQUENCE: 38
tcttagaata aatacctacc c                                        21

<210> SEQ ID NO 39
<211> LENGTH: 23
<212> TYPE: PRT
<213> ORGANISM: Artificial Sequence
<220> FEATURE:
<223> OTHER INFORMATION: Description of Artificial Sequence: Modified
      Streptococcus Pneumonia peptide
<220> FEATURE:
<221> NAME/KEY: VARIANT
<222> LOCATION: (6)..(11)
<223> OTHER INFORMATION: They can be any amino acid.
<220> FEATURE:
<221> NAME/KEY: VARIANT
<222> LOCATION: (15)
<223> OTHER INFORMATION: It can be any amino acid.
<220> FEATURE:
<221> NAME/KEY: VARIANT
<222> LOCATION: (20)
<223> OTHER INFORMATION: It can be any amino acid.

<400> SEQUENCE: 39

Arg Lys Glu Phe His Xaa Xaa Xaa Xaa Xaa Xaa Gln Leu Leu Xaa Asp
    1               5                   10                  15
    Lys Arg Pro Xaa Arg Asp Tyr
                20

<210> SEQ ID NO 40
<211> LENGTH: 8
<212> TYPE: PRT
<213> ORGANISM: Streptococcus pneumoniae

<400> SEQUENCE: 40

Asp Lys Arg Pro Ala Arg Asp Tyr
    1               5

<210> SEQ ID NO 41
<211> LENGTH: 7
<212> TYPE: PRT
<213> ORGANISM: Streptococcus pneumoniae

<400> SEQUENCE: 41

Arg Lys Glu Phe His Asn Val
    1               5

<210> SEQ ID NO 42
<211> LENGTH: 7
<212> TYPE: PRT
<213> ORGANISM: Streptococcus pneumoniae

<400> SEQUENCE: 42

Leu Ser Ser Gly Gln Leu Leu
    1               5

<210> SEQ ID NO 43
<211> LENGTH: 25
<212> TYPE: PRT
<213> ORGANISM: Artificial Sequence
<220> FEATURE:
<223> OTHER INFORMATION: Description of Artificial Sequence: Modified
      Streptococcus Pneumonia peptide
```

```
<220> FEATURE:
<221> NAME/KEY: VARIANT
<222> LOCATION: (2)..(6)
<223> OTHER INFORMATION: They can be any amino acid.
<220> FEATURE:
<221> NAME/KEY: VARIANT
<222> LOCATION: (11)
<223> OTHER INFORMATION: It can be any amino acid.
<220> FEATURE:
<221> NAME/KEY: VARIANT
<222> LOCATION: (13)..(15)
<223> OTHER INFORMATION: They can be any amino acid.
<220> FEATURE:
<221> NAME/KEY: VARIANT
<222> LOCATION: (17)..(20)
<223> OTHER INFORMATION: They can be any amino acid.
<220> FEATURE:
<221> NAME/KEY: VARIANT
<222> LOCATION: (22)..(24)
<223> OTHER INFORMATION: They can be any amino acid.

<400> SEQUENCE: 43

Met Xaa Xaa Xaa Xaa Xaa Asn Val Leu Ser Xaa Gly Xaa Xaa Xaa Ala
      1               5                  10                  15
     Xaa Xaa Xaa Xaa Ala Xaa Xaa Xaa Asn
                  20                  25

<210> SEQ ID NO 44
<211> LENGTH: 27
<212> TYPE: PRT
<213> ORGANISM: Streptococcus pneumoniae

<400> SEQUENCE: 44

Met Arg Lys Glu Phe His Asn Val Leu Ser Ser Gly Gln Leu Leu Ala
      1               5                  10                  15
     Asp Lys Arg Pro Ala Arg Asp Tyr Asn Arg Lys
                  20                  25

<210> SEQ ID NO 45
<211> LENGTH: 312
<212> TYPE: DNA
<213> ORGANISM: Streptococcus pneumoniae

<400> SEQUENCE: 45
aatttgaaaa aatgagtcta gaataaagat tgcatcttgt gtttctattc aagaatagtg     60
     gataggaatg gctatttaac aattcaaaat aaatccgaaa gcagtggtga aaatcattgc    120
     tttcagttgc tttctttgta ctttagtgct taaatataat atactaaagt tatggaattt    180
     atgagaaagg aatttcacaa cgttttatct agtggtcagt tgcttgcaga caaaaggcca    240
     gcaagagact ataatagaaa atagggtagg tatttattct aagaaaaata aaaaatagag    300
     agcagttaaa gt                                                       312

<210> SEQ ID NO 46
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 46
aatgagtcta gaataaagat tgc                                            23

<210> SEQ ID NO 47
<211> LENGTH: 27
<212> TYPE: PRT
<213> ORGANISM: Artificial Sequence
<220> FEATURE:
<223> OTHER INFORMATION: Description of Artificial Sequence: Modified
      Streptococcus Pneumonia peptide
```

```
<400> SEQUENCE: 47

Met Arg Lys Glu Phe His Asn Val Leu Ser Ala Gly Gln Leu Leu Ala
      1               5                  10                  15
    Asp Lys Arg Pro Ala Arg Asp Tyr Asn Arg Lys
                 20                  25

<210> SEQ ID NO 48
<211> LENGTH: 30
<212> TYPE: PRT
<213> ORGANISM: Streptococcus pneumoniae

<400> SEQUENCE: 48

Met Glu Phe Met Arg Lys Glu Phe His Asn Val Leu Ser Ser Gly Gln
      1               5                  10                  15
    Leu Leu Ala Asp Lys Arg Pro Ala Arg Asp Tyr Asn Arg Lys
                 20                  25                  30

<210> SEQ ID NO 49
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 49
acgaagaatt cgctaagaag aacggt                                      26

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 50
attaaggatc cagctatcaa                                             20

<210> SEQ ID NO 51
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 51
atcaagggat ccactgccaa ggc                                         23

<210> SEQ ID NO 52
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 52
agaggagaat tcccacttcc ttgcg                                       25

<210> SEQ ID NO 53
<211> LENGTH: 81
<212> TYPE: DNA
<213> ORGANISM: Streptococcus pneumoniae

<400> SEQUENCE: 53
atgagaaagg aatttcacaa cgttttatct agtggtcagt tgcttgcaga caaaggcca  60
    gcaagagact aaatagaaa a                                            81
```

```
<210> SEQ ID NO 54
<211> LENGTH: 90
<212> TYPE: DNA
<213> ORGANISM: Streptococcus pneumoniae

<400> SEQUENCE: 54 atgaattta tgagaaagga atttcacaac gttttatcta gtggtcagtt gcttgcagac   60
    aaaaggccag caagagacta taatagaaaa                                    90

<210> SEQ ID NO 55
<211> LENGTH: 5
<212> TYPE: PRT
<213> ORGANISM: Artificial Sequence
<220> FEATURE:
<223> OTHER INFORMATION: Description of Artificial Sequence: Consensus
<220> FEATURE:
<221> NAME/KEY: PEPTIDE
<222> LOCATION: (1)
<223> OTHER INFORMATION: Xaa can be Leu or Tyr
<220> FEATURE:
<221> NAME/KEY: PEPTIDE
<222> LOCATION: (5)
<223> OTHER INFORMATION: Xaa can be Gln or Met

<400> SEQUENCE: 55

Xaa Ser Gly Gly Xaa
     1               5

<210> SEQ ID NO 56
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 56
acgaagaatt cgctaagaag aacggt                                        26

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 57
attaaggatc cagctatcaa                                               20

<210> SEQ ID NO 58
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 58
atcaagggat ccactgccaa ggc                                           23

<210> SEQ ID NO 59
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 59
agaggagaat tcccacttcc ttgcg                                         25
```

```
<210> SEQ ID NO 60
<211> LENGTH: 27
<212> TYPE: PRT
<213> ORGANISM: Streptococcus Pneumoniae
<220> FEATURE:
<223> OTHER INFORMATION: Description of Artificial Sequence: Synthetic
      amino acids

<400> SEQUENCE: 60

Met Arg Lys Glu Phe His Asn Val Leu Ser Ser Asp Gln Leu Leu Thr
    1               5                   10                  15
    Asp Lys Arg Pro Ala Arg Asp Tyr Asn Arg Lys
                20                  25

<210> SEQ ID NO 61
<211> LENGTH: 25
<212> TYPE: PRT
<213> ORGANISM: Streptococcus Pneumoniae
<220> FEATURE:
<223> OTHER INFORMATION: Description of Artificial Sequence: Synthetic
      amino acids

<400> SEQUENCE: 61

Met Arg Lys Glu Phe His Asn Val Leu Ser Ser Asp Gln Leu Leu Thr
    1               5                   10                  15
    Asp Lys Arg Pro Ala Arg Asp Tyr Asn
                20                  25

<210> SEQ ID NO 62
<211> LENGTH: 33
<212> TYPE: PRT
<213> ORGANISM: Artificial Sequence
<220> FEATURE:
<223> OTHER INFORMATION: Description of Artificial Sequence: Synthetic
      amino acids

<400> SEQUENCE: 62

Gln Asn Tyr Asn Leu Ile Asp Tyr Leu Ser Pro Leu Glu Asn Ile Arg
    1               5                   10                  15
    Leu Val Asn Lys Lys Ala Ser Lys Asn Thr Leu Leu Glu Leu Gly Leu
                20                  25                  30
    Asp

<210> SEQ ID NO 63
<211> LENGTH: 33
<212> TYPE: PRT
<213> ORGANISM: Artificial Sequence
<220> FEATURE:
<223> OTHER INFORMATION: Description of Artificial Sequence: Synthetic
      amino acids

<400> SEQUENCE: 63

Gln Asn Tyr Asn Leu Ile Asp Tyr Leu Ser Pro Leu Glu Asn Ile Gln
    1               5                   10                  15
    Leu Val Asn Lys Lys Ala Ser Lys Asp Thr Leu Leu Glu Leu Gly Leu
                20                  25                  30
    Asp

<210> SEQ ID NO 64
<211> LENGTH: 215
<212> TYPE: PRT
<213> ORGANISM: Streptococcus Pneumoniae

<400> SEQUENCE: 64

Met Thr Leu Leu Gln Leu Gln Asp Val Thr Tyr Arg Tyr Lys Asn Thr
    1               5                   10                  15
    Ala Glu Ala Val Leu Tyr Gln Ile Asn Tyr Asn Phe Glu Pro Gly Lys
                20                  25                  30
    Phe Tyr Ser Ile Ile Gly Glu Ser Gly Ala Gly Lys Ser Thr Leu Leu
                35                  40                  45
```

-continued

```
           Ser Leu Leu Ala Gly Leu Asp Ser Pro Val Glu Gly Ser Ile Leu Phe
               50                  55                  60
           Gln Gly Glu Asp Ile Arg Lys Gly Tyr Ser Tyr His Arg Met His
            65                  70                  75                  80
           His Ile Ser Leu Val Phe Gln Asn Tyr Asn Leu Ile Asp Tyr Leu Ser
                           85                  90                  95
           Pro Leu Glu Asn Ile Gln Leu Val Asn Lys Ala Ser Lys Asp Thr
                       100                 105                 110
           Leu Leu Glu Leu Gly Leu Asp Glu Ser Gln Ile Lys Arg Asn Val Leu
                       115                 120                 125
           Gln Leu Ser Gly Gly Gln Gln Arg Val Ala Ile Ala Arg Ser Leu
                       130                 135                 140
           Val Ser Glu Ala Pro Val Ile Leu Ala Asp Glu Pro Thr Gly Asn Leu
           145                 150                 155                 160
           Asp Pro Lys Thr Ala Gly Asp Ile Val Glu Leu Leu Lys Ser Leu Ala
                           165                 170                 175
           Gln Lys Thr Gly Lys Cys Val Ile Val Thr His Ser Lys Glu Val
                       180                 185                 190
           Ala Gln Ala Ser Asp Ile Thr Leu Glu Leu Lys Asp Lys Lys Leu Thr
                       195                 200                 205
           Glu Thr Arg Asn Thr Ser Lys
                       210                 215

<210> SEQ ID NO 65
<211> LENGTH: 84
<212> TYPE: DNA
<213> ORGANISM: Streptococcus Pneumoniae

<400> SEQUENCE: 65
atgagaaagg aatttcacaa cgttttatct agtggtcagt tgcttgcaga caaaaggcca    60
    gcaagagact ataatagaaa atag                                            84

<210> SEQ ID NO 66
<211> LENGTH: 84
<212> TYPE: DNA
<213> ORGANISM: Streptococcus pneumoniae

<400> SEQUENCE: 66
atgagaaagg aatttcacaa cgttttatct agtgatcagt tgcttacaga caaaaggcca    60
    gcaagagact ataatagaaa atag                                            84

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 67
ctgctgaagc agtcctatat                                                 20

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 68
ttcgacaata tctccagcag                                                 20

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: Primer
```

```
<400> SEQUENCE: 69
gagctcttgc tggatggtga                                           20

<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 70
cctcacggat catctcttca                                           20

<210> SEQ ID NO 71
<211> LENGTH: 675
<212> TYPE: DNA
<213> ORGANISM: Streptococcus pneumoniae

<400> SEQUENCE: 71
atgactttat tacaattaca agatgttacc taccgttata agaatactgc tgaagcagtc   60
    ccatataaga atactgctga agcagtccta tatcagatca attataattt tgaacccgga  120
    aaattttaca gtattattgg ggagtcagga gcaggaaaat ccacactctt gtccctactt  180
    gctggtctag atagtcctgt tgaaggttct atcctttttc aaggagagga tattcgtaag  240
    aagggctatt cttaccatcg catgcaccat atttccctgg tctttcaaaa ttataacttg  300
    atagattatc tttctccgct ggaaaatatc cgattggtca acaaaaaggc aagcaaggat  360
    acacttcttg agcttggttt ggatgaaagt cagatcaagc ggaatgttct ccagttatca  420
    ggtggtcaac agcaacgtgt tgccattgct cgcagttgtc tctcagaagc tccagttatt  480
    ctagctgatg agccaacagg aaatctggat cctaaaactg ctggagatat tgtcgaacta  540
    ctcaaatcac ttgcccagaa aacaggtaaa tgtgtgattg tcgtaactca cagtaaagaa  600
    gtggcacaag cgtcagatat tacacttgaa ttaaaggata agaaactgac tgaaacgcgc  660
    aatactagta aataa                                                 675

<210> SEQ ID NO 72
<211> LENGTH: 224
<212> TYPE: PRT
<213> ORGANISM: Streptococcus pneumoniae

<400> SEQUENCE: 72

Met Thr Leu Leu Gln Leu Gln Asp Val Thr Tyr Arg Tyr Lys Asn Thr
    1               5                   10                  15
    Ala Glu Ala Val Pro Tyr Lys Asn Thr Ala Glu Ala Val Leu Tyr Gln
                    20                  25                  30
    Ile Asn Tyr Asn Phe Glu Pro Gly Lys Phe Tyr Ser Ile Ile Gly Glu
                35                  40                  45
    Ser Gly Ala Gly Lys Ser Thr Leu Leu Ser Leu Leu Ala Gly Leu Asp
        50                  55                  60
    Ser Pro Val Glu Gly Ser Ile Leu Phe Gln Gly Glu Asp Ile Arg Lys
    65                  70                  75                  80
    Lys Gly Tyr Ser Tyr His Arg Met His His Ile Ser Leu Val Phe Gln
                    85                  90                  95
    Asn Tyr Asn Leu Ile Asp Tyr Leu Ser Pro Leu Glu Asn Ile Arg Leu
                100                 105                 110
    Val Asn Lys Lys Ala Ser Lys Asp Thr Leu Leu Glu Leu Gly Leu Asp
                115                 120                 125
    Glu Ser Gln Ile Lys Arg Asn Val Leu Gln Leu Ser Gly Gly Gln Gln
            130                 135                 140
    Gln Arg Val Ala Ile Ala Arg Ser Leu Val Ser Glu Ala Pro Val Ile
    145                 150                 155                 160
    Leu Ala Asp Glu Pro Thr Gly Asn Leu Asp Pro Lys Thr Ala Gly Asp
                    165                 170                 175
    Ile Val Glu Leu Leu Lys Ser Leu Ala Gln Lys Thr Gly Lys Cys Val
                180                 185                 190
    Ile Val Val Thr His Ser Lys Glu Val Ala Gln Ala Ser Asp Ile Thr
                195                 200                 205
    Leu Glu Leu Lys Asp Lys Lys Leu Thr Glu Thr Arg Asn Thr Ser Lys
        210                 215                 220

<210> SEQ ID NO 73
<211> LENGTH: 675
<212> TYPE: DNA
<213> ORGANISM: Streptococcus pneumoniae
```

-continued

<400> SEQUENCE: 73

```
atgactttat tacaattaca agatgttacc taccgttata agaatactgc tgaagcagtc    60
ccatataaga atactgctga agcagtccta tatcagatca attataattt tgaacccgga   120
aaattttaca gtattattgg ggagtcagga gcaggaaaat ccacactctt gtccctactt   180
gctggtctag atagtcctgt tgaaggttct atccttttc aaggagagga tattcgtaag    240
aaggctatt cttaccatcg catgcaccat atttccctgg tctttcaaaa ttataacttg    300
atagattatc tttctccgct ggaaaatatc cgattggtca acaaaaaggc aagcaaggat   360
acacttcttg agcttggttt ggatgaaagt cagatcaagc ggaatgttct ccagttatca   420
ggtggtcaac agcaacgtgt tgccattgct cgcagtttgg tctcagaagc tccagttatt   480
ctagctgatg agccaacagg aaatctggat cctaaaactg ctggagatat tgtcgaacta   540
ctcaaatcac ttgcccagaa aacaggtaaa tgtgtgattg tcgtaactca cagtaaagaa   600
gtggcacaag cgtcagatat tacacttgaa ttaaaggata agaaactgac tgaaacgcgc   660
aatactagta aataa                                                    675
```

<210> SEQ ID NO 74
<211> LENGTH: 224
<212> TYPE: PRT
<213> ORGANISM: Streptococcus pneumoniae

<400> SEQUENCE: 74

```
Met Thr Leu Leu Gln Leu Gln Asp Val Thr Tyr Arg Tyr Lys Asn Thr
 1               5                  10                  15
Ala Glu Ala Val Pro Tyr Lys Asn Thr Ala Glu Ala Val Leu Tyr Gln
            20                  25                  30
Ile Asn Tyr Asn Phe Glu Pro Gly Lys Phe Tyr Ser Ile Ile Gly Glu
        35                  40                  45
Ser Gly Ala Gly Lys Ser Thr Leu Leu Ser Leu Leu Ala Gly Leu Asp
    50                  55                  60
Ser Pro Val Glu Gly Ser Ile Leu Phe Gln Gly Asp Ile Arg Lys
65                  70                  75                  80
Lys Gly Tyr Ser Tyr His Arg Met His His Ile Ser Leu Val Phe Gln
                85                  90                  95
Asn Tyr Asn Leu Ile Asp Tyr Leu Ser Pro Leu Glu Asn Ile Arg Leu
            100                 105                 110
Val Asn Lys Lys Ala Ser Lys Asp Thr Leu Leu Glu Leu Gly Leu Asp
        115                 120                 125
Glu Ser Gln Ile Lys Arg Asn Val Leu Gln Leu Ser Gly Gly Gln Gln
    130                 135                 140
Gln Arg Val Ala Ile Ala Arg Ser Leu Val Ser Glu Ala Pro Val Ile
145                 150                 155                 160
Leu Ala Asp Glu Pro Thr Gly Asn Leu Asp Pro Lys Thr Ala Gly Asp
                165                 170                 175
Ile Val Glu Leu Leu Lys Ser Leu Ala Gln Lys Thr Gly Lys Cys Val
            180                 185                 190
Ile Val Val Thr His Ser Lys Glu Val Ala Gln Ala Ser Asp Ile Thr
        195                 200                 205
Leu Glu Leu Lys Asp Lys Lys Leu Thr Glu Thr Arg Asn Thr Ser Lys
    210                 215                 220
```

<210> SEQ ID NO 75
<211> LENGTH: 1281
<212> TYPE: DNA
<213> ORGANISM: Streptococcus pneumoniae

<400> SEQUENCE: 75

```
atgaatccaa tccaaagatc ttgggcttat gtcagcagaa agcgactgag aagttttatt    60
ttatttctga tttttattggt cttattggcc ggaatttcag cctgtttgac tctgatgaag   120
tccaacaaaa cagtagaaag caatctttat aaatcactca atacatcttt ttctattaag   180
aagatagaga atggtcagac attcaagttg tcagacctag catctgtaag caagattaag   240
gggctggaaa atgtctctcc tgaacttgag acggtcgcaa aactaaaaga caaggaagca   300
gtgactggcg agcagagcgt ggagcgtgat gatttatcag ctgcagacaa taacttggtt   360
agcttaacgg ctcttgagga ttcatccaag gatgtaacct ttaccagttc ggcttttcaat   420
ctaaaagaag ggcgacacct tcaaaagggg gattccaaga aaatcctat ccacgaagaa    480
gaattggcta agaagaacgg tctttcgctt catgacaaga ttggcttgga tgctggtcag   540
tctgaatctg gaaaaggaca aacagtagag tttgagatta ttggcatctt ttctggtaaa   600
aaacaagaga attcacagg cttgtcttct gacttcagtg aaaatcaagt ctttacagac   660
tatgaaagta gccaaaccct ttgggcaat agtgaagctc aagtcagtgc agcacgcttc   720
tatgtagaaa atcctaagga aatggacgga ctcatgaagc aggtagaaaa cttggccttg   780
gaaaatcaag gctaccaagt cgaaaaggaa aacaaggctt ttgaacaaat caaagactaa   840
gttgcaactt tccaaacctt cctgaccatc ttcctttatg ggatgttgat agcaggagct   900
ggagccttaa ttctggtttt gtctctctgg ttgagagaac gggtctatga agtgggattt   960
ttacttgcac ttggaaaagg caagagctcg atcttcctac aattctgttt agaggtagtt  1020
ttggtatctc ttggagcttt gcttccagca tttgttgcag aaacgcaatc acaacttac   1080
ctactccaaa ctctactagc aagtggagat caggcaagct acaagatac actagccaaa  1140
```

```
             gcaagcagtt tatcaactag catcttatct tttgcagaat cctatgtttt tctagttctg 1200
             cttagttgct tatctgtagc cctttgtttc ctattcttat ttagaaaatc accgaaagaa 1260
             attttatcat ctattagtta a                                          1281
```

<210> SEQ ID NO 76
<211> LENGTH: 224
<212> TYPE: PRT
<213> ORGANISM: Streptococcus pneumoniae

<400> SEQUENCE: 76

```
     Met Thr Leu Leu Gln Leu Gln Asp Val Thr Tyr Arg Tyr Lys Asn Thr
     1               5                   10                  15
     Ala Glu Ala Val Pro Tyr Lys Asn Thr Ala Glu Ala Val Leu Tyr Gln
                     20                  25                  30
     Ile Asn Tyr Asn Phe Glu Pro Gly Lys Phe Tyr Ser Ile Ile Gly Glu
                 35                  40                  45
     Ser Gly Ala Gly Lys Ser Thr Leu Leu Ser Leu Leu Ala Gly Leu Asp
             50                  55                  60
     Ser Pro Val Glu Gly Ser Ile Leu Phe Gln Gly Glu Asp Ile Arg Lys
     65                  70                  75                  80
     Lys Gly Tyr Ser Tyr His Arg Met His His Ile Ser Leu Val Phe Gln
                     85                  90                  95
     Asn Tyr Asn Leu Ile Asp Tyr Leu Ser Pro Leu Glu Asn Ile Arg Leu
                 100                 105                 110
     Val Asn Lys Lys Ala Ser Lys Asp Thr Leu Leu Glu Leu Gly Leu Asp
                 115                 120                 125
     Glu Ser Gln Ile Lys Arg Asn Val Leu Gln Leu Ser Gly Gly Gln Gln
     130                 135                 140
     Gln Arg Val Ala Ile Ala Arg Ser Leu Val Ser Glu Ala Pro Val Ile
     145                 150                 155                 160
     Leu Ala Asp Glu Pro Thr Gly Asn Leu Asp Pro Lys Thr Ala Gly Asp
                     165                 170                 175
     Ile Val Glu Leu Leu Lys Ser Leu Ala Gln Lys Thr Gly Lys Cys Val
                 180                 185                 190
     Ile Val Val Thr His Ser Lys Glu Val Ala Gln Ala Ser Asp Ile Thr
                 195                 200                 205
     Leu Glu Leu Lys Asp Lys Lys Leu Thr Glu Thr Arg Asn Thr Ser Lys
             210                 215                 220
```